US012611316B2

(12) United States Patent
Frenkel

(10) Patent No.: US 12,611,316 B2
(45) Date of Patent: Apr. 28, 2026

(54) INTERVERTEBRAL MEMBERS AND METHODS OF USING A BONE REINFORCING COMPOSITION FOR RETAINING THE INTERVERTEBRAL MEMBERS

(71) Applicant: FutureSpine Inc., Naples, FL (US)

(72) Inventor: Mark Frenkel, Naples, FL (US)

(73) Assignee: FutureSpine Inc., Naples, FL (US)

( * ) Notice: Subject to any disclaimer, the term of this patent is extended or adjusted under 35 U.S.C. 154(b) by 0 days.

(21) Appl. No.: 19/278,532

(22) Filed: Jul. 23, 2025

(65) Prior Publication Data

US 2026/0026944 A1     Jan. 29, 2026

Related U.S. Application Data

(60) Provisional application No. 63/827,769, filed on Jun. 20, 2025, provisional application No. 63/727,639, (Continued)

(51) Int. Cl.
*A61F 2/46* (2006.01)
*A61B 17/88* (2006.01)
(Continued)

(52) U.S. Cl.
CPC ........ *A61F 2/4601* (2013.01); *A61B 17/8841* (2013.01); *A61F 2/2846* (2013.01);
(Continued)

(58) Field of Classification Search
CPC ...... A61F 2/4601; A61F 2/2846; A61F 2/442; A61F 2002/285; A61F 2002/30062;
(Continued)

(56) References Cited

U.S. PATENT DOCUMENTS 5,236,460 A     8/1993   Barber
5,972,031 A     10/1999  Biedermann et al.
(Continued)

FOREIGN PATENT DOCUMENTS

CN          215228771       12/2021
EP          2419030 B1      1/2017
(Continued)

OTHER PUBLICATIONS

International Search Report and Written Opinion received for International Application No. PCT/US2025/030465, mailed Jul. 16, 2025 (13 pages).

(Continued)

*Primary Examiner* — Eduardo C Robert
*Assistant Examiner* — Tara Rose E Carter
(74) *Attorney, Agent, or Firm* — Perkins Coie LLP

(57) ABSTRACT

A method for dispensing a bone reinforcement composition into an intervertebral spacer and at least one adjacent vertebra can help retain the implant in situ. A cannula guide is inserted into a first vertebra guided by a live imaging system. A curved directional composition delivery cannula is inserted through a tubular body of the guide; then positioning the delivery cannula along a desired path, positioning an end using a curved end as a steering mechanism. The delivery cannula passes through a first vertebra, into the intervertebral spacer, and optionally into a second vertebra. A volume of reinforcement composition is dispensed using cyclical steps of incrementally withdrawing the delivery cannula and dispensing of the reinforcement composition until the path is filled with reinforcement composition stabilizing the respective vertebrae and/or interbody devices relative to each other. In an alternate arrangement, the cannula is inserted through a guide integrated into the spacer.

36 Claims, 58 Drawing Sheets

Related U.S. Application Data filed on Dec. 3, 2024, provisional application No. 63/674,778, filed on Jul. 23, 2024.

(51) Int. Cl.
| | |
|---|---|
| *A61F 2/28* | (2006.01) |
| *A61F 2/30* | (2006.01) |
| *A61F 2/44* | (2006.01) |

(52) U.S. Cl.
CPC ........ *A61F 2/442* (2013.01); *A61F 2002/285* (2013.01); *A61F 2002/30062* (2013.01); *A61F 2002/30317* (2013.01); *A61F 2002/3092* (2013.01); *A61F 2002/4631* (2013.01)

(58) Field of Classification Search
CPC .... A61F 2002/30317; A61F 2002/3092; A61F 2002/4631; A61B 17/8805; A61B 17/8811; A61B 17/3472; A61B 17/8822; A61B 17/8833
See application file for complete search history.

(56) References Cited

U.S. PATENT DOCUMENTS

| | | | |
|---|---|---|---|
| 6,056,749 A * | 5/2000 | Kuslich | A61F 2/4611 |
| | | | 606/279 |
| 6,113,638 A | 9/2000 | Williams et al. | |
| 6,447,543 B1 | 9/2002 | Studer et al. | |
| 6,558,423 B1 | 5/2003 | Michelson | |
| 6,582,467 B1 | 6/2003 | Teitelbaum et al. | |
| 6,776,798 B2 | 8/2004 | Camino et al. | |
| 7,285,134 B2 | 10/2007 | Berry et al. | |
| 7,670,359 B2 | 3/2010 | Yundt | |
| 7,749,268 B2 | 7/2010 | Trieu | |
| 8,313,528 B1 | 11/2012 | Wensel | |
| 8,328,872 B2 | 12/2012 | Duffield et al. | |
| 8,551,175 B1 | 10/2013 | Wensel | |
| 8,574,273 B2 | 11/2013 | Russell et al. | |
| 8,979,926 B2 | 3/2015 | Quinn et al. | |
| 9,248,028 B2 | 2/2016 | Gamache | |
| 9,265,548 B2 | 2/2016 | Jones et al. | |
| 9,387,088 B2 * | 7/2016 | Roche | A61B 17/7097 |
| 9,402,740 B1 | 8/2016 | Donaldson | |
| 9,402,741 B1 | 8/2016 | Donaldson | |
| 9,408,715 B2 | 8/2016 | Donner et al. | |
| 9,517,144 B2 | 12/2016 | Mcatamney et al. | |
| 9,730,804 B2 | 8/2017 | Cowan et al. | |
| 9,877,842 B2 | 1/2018 | Chataigner et al. | |
| 9,925,056 B2 | 3/2018 | Donner et al. | |
| 9,949,836 B2 | 4/2018 | Quinn et al. | |
| 10,105,236 B2 | 10/2018 | Donner et al. | |
| 10,159,582 B2 | 12/2018 | Gamache | |
| 10,398,565 B2 | 9/2019 | Bender et al. | |
| 10,716,680 B2 | 7/2020 | Schmura et al. | |
| 10,806,592 B2 | 10/2020 | Donner et al. | |
| 10,813,773 B2 | 10/2020 | Gamache | |
| 11,253,373 B2 | 2/2022 | Bender et al. | |
| 11,318,026 B2 | 5/2022 | Oh | |
| 11,617,654 B2 | 4/2023 | Donner et al. | |
| 12,102,543 B2 | 10/2024 | Berger et al. | |
| 12,121,452 B2 | 10/2024 | Donner et al. | |
| 12,201,532 B2 | 1/2025 | Oh | |
| 12,357,467 B2 | 7/2025 | Schmura et al. | |
| 2002/0120240 A1 * | 8/2002 | Bagga | A61B 17/8819 |
| | | | 606/93 |
| 2005/0049707 A1 * | 3/2005 | Ferree | A61B 17/8811 |
| | | | 623/908 |
| 2005/0137707 A1 | 6/2005 | Malek | |
| 2005/0154460 A1 * | 7/2005 | Yundt | A61F 2/4455 |
| | | | 623/17.11 |
| 2006/0173542 A1 | 8/2006 | Shikinami | |
| 2006/0241632 A1 * | 10/2006 | Sherman | A61F 2/4425 |
| | | | 606/86 R |
| 2007/0213824 A1 * | 9/2007 | Trieu | A61B 17/7061 |
| | | | 623/17.11 |
| 2007/0276377 A1 | 11/2007 | Yundt | |
| 2008/0058931 A1 | 3/2008 | White et al. | |
| 2008/0281428 A1 | 11/2008 | Meyers et al. | |
| 2009/0149959 A1 | 6/2009 | Conner et al. | |
| 2009/0204158 A1 | 8/2009 | Sweeney | |
| 2009/0248163 A1 | 10/2009 | King et al. | |
| 2011/0004307 A1 * | 1/2011 | Ahn | A61F 2/4455 |
| | | | 606/279 |
| 2011/0022173 A1 | 1/2011 | Melkent et al. | |
| 2011/0022176 A1 | 1/2011 | Zucherman et al. | |
| 2011/0077741 A1 | 3/2011 | Heinz | |
| 2011/0178599 A1 | 7/2011 | Brett | |
| 2011/0230970 A1 * | 9/2011 | Lynn | A61F 2/4601 |
| | | | 623/17.16 |
| 2012/0109303 A1 | 5/2012 | Capote | |
| 2012/0232599 A1 | 9/2012 | Schoenly et al. | |
| 2013/0079879 A1 | 3/2013 | Suh | |
| 2014/0236299 A1 | 8/2014 | Roeder et al. | |
| 2014/0324172 A1 | 10/2014 | Haines | |
| 2016/0206441 A1 | 7/2016 | Matsumoto et al. | |
| 2018/0263785 A1 * | 9/2018 | Vishnubhotla | A61F 2/447 |
| 2018/0303622 A1 | 10/2018 | Laurence et al. | |
| 2021/0401587 A1 | 12/2021 | Zakelj | |
| 2023/0094575 A1 | 3/2023 | Bird et al. | |
| 2023/0320866 A1 | 10/2023 | Hutton et al. | |
| 2025/0288337 A1 | 9/2025 | Frenkel et al. | |

FOREIGN PATENT DOCUMENTS

| | | | | | |
|---|---|---|---|---|---|
| EP | 2558036 | B1 | 8/2017 | | |
| EP | 2822511 | B1 | 5/2019 | | |
| EP | 2579821 | B1 | 2/2020 | | |
| EP | 4262636 | A1 | 10/2023 | | |
| EP | 4413957 | | 8/2024 | | |
| WO | WO-2021188465 | A1 * | 9/2021 | | A61F 2/447 |
| WO | 2022251746 | | 12/2022 | | |

OTHER PUBLICATIONS

International Search Report and Written Opinion mailed Dec. 30, 2025 for counterpart International Application No. PCT/US2025/038911 (15 pages).

\* cited by examiner

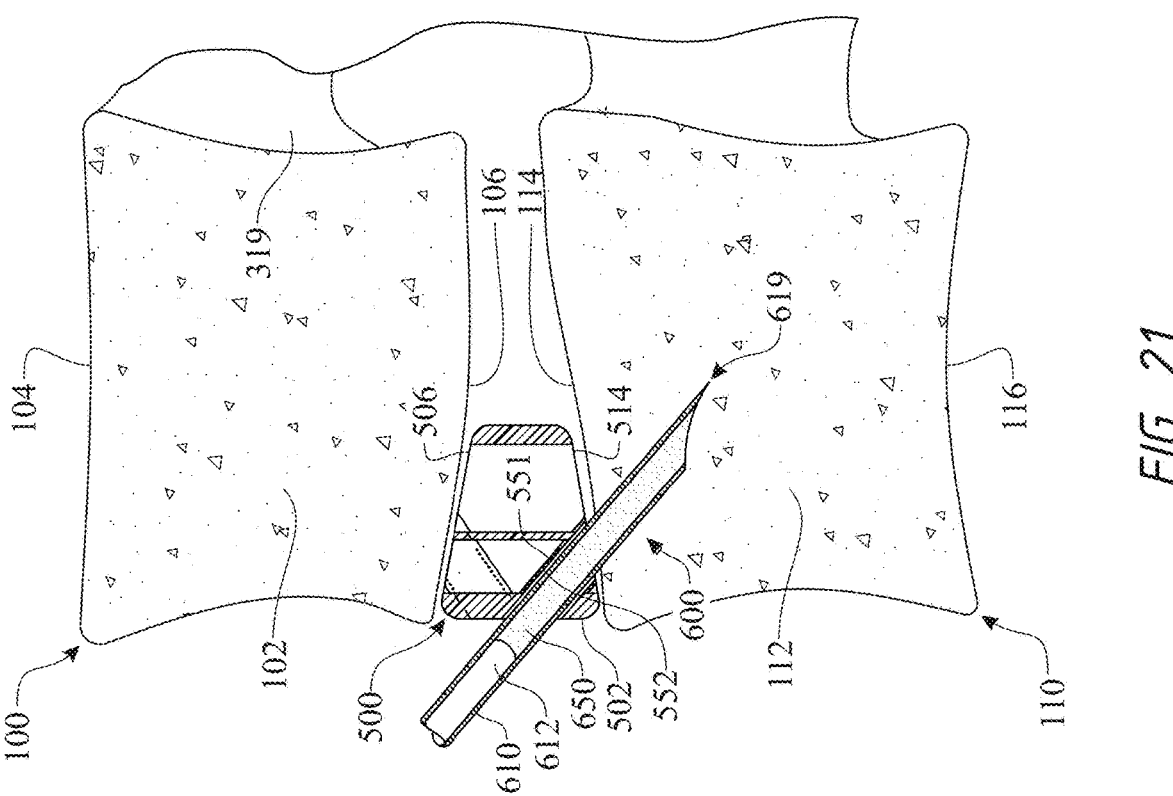
*FIG. 21*

3620

3620

3620

3620

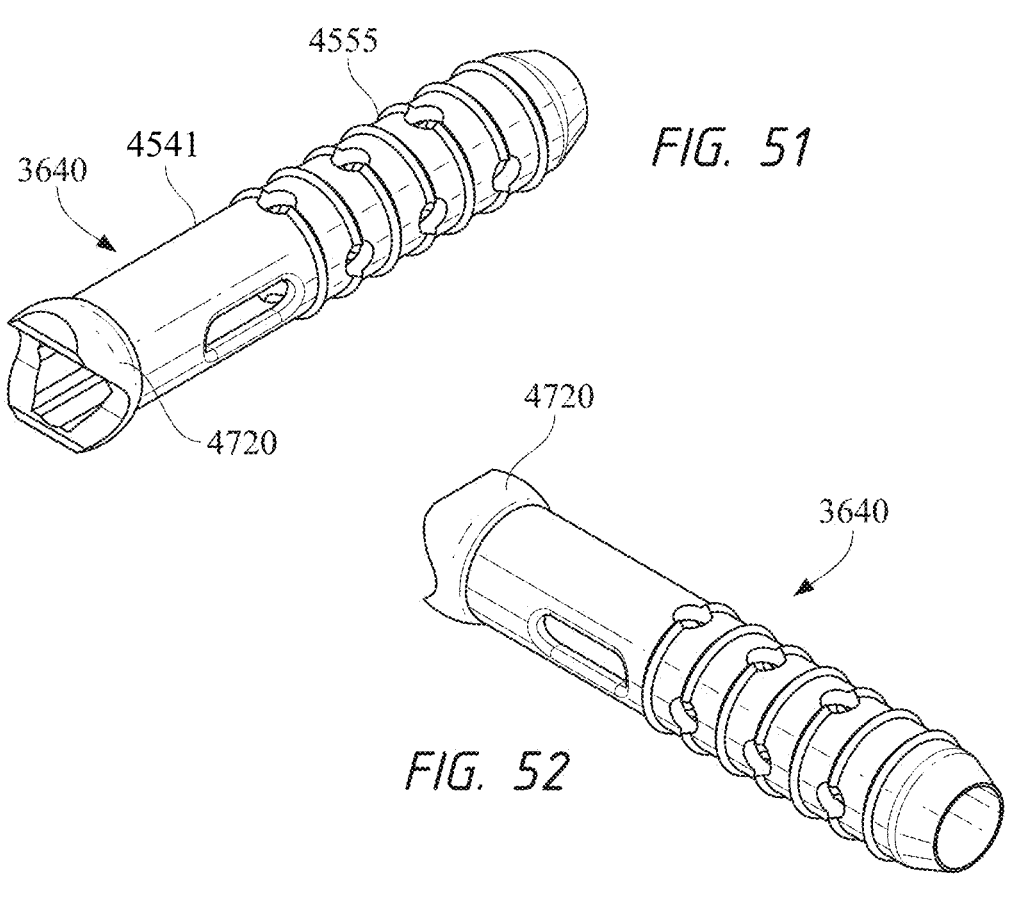
*FIG. 51*
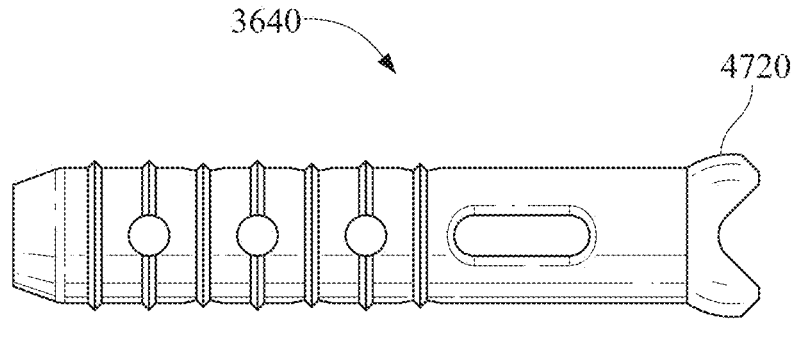
*FIG. 52*
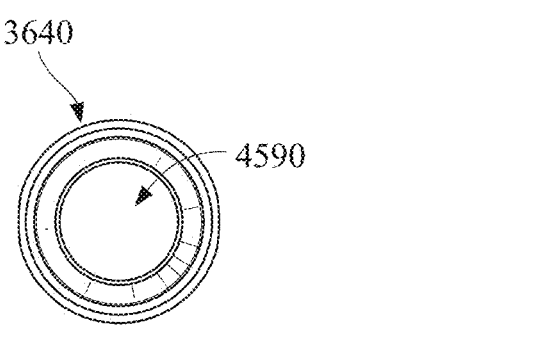
*FIG. 53*
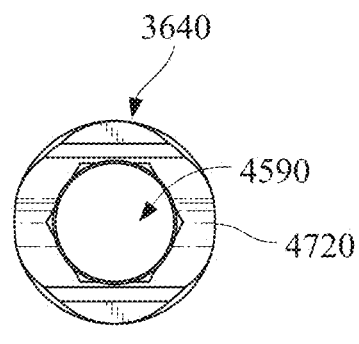
*FIG. 54*                    *FIG. 55*

7060

6420

7070

7090

7050

7050

7110

7090

7090

7220

7050

7230

7200

72

7230

72

INTERVERTEBRAL MEMBERS AND METHODS OF USING A BONE REINFORCING COMPOSITION FOR RETAINING THE INTERVERTEBRAL MEMBERS

CROSS-REFERENCE TO RELATED APPLICATIONS

The present application claims the priority benefit of U.S. provisional patent application No. 63/674,778, filed Jul. 23, 2024; U.S. provisional patent application No. 63/727,639, filed Dec. 3, 2024; and U.S. provisional patent application No. 63/827,769, filed Jun. 20, 2025, all of which are incorporated herein by reference in their entireties.

TECHNICAL FIELD

The present disclosure generally relates to a system of dispensing bone reinforcing material into vertebrae during a surgical procedure. More specifically, the system includes an intervertebral member and an access cannula to access one vertebra or a pair of vertebrae. The cannula can be moved through the vertebra in a direction substantially perpendicular to a transverse plane (parallel to the spinal column) or another suitable direction. The cannula can be used to deliver bone reinforcing material (bone cement, bone graft, etc.) is injected into the vertebrae.

BACKGROUND

Degenerative disc disease describes the gradual failure of the disc to perform its function often resulting in reduced range of motion and back pain. Degenerative disc disease can be attributed to aging, overloading of the spine, and genetic factors. The disc is an avascular structure, which makes it susceptible to damage and inability for reliable regeneration. This explains the wide prevalence of degenerative disc disease.

Physiologically, the disc acts as a shock absorber between adjacent vertebrae. The disc also plays a role in maintaining spinal alignment and facilitating range of motion. Degeneration and collapse of the intervertebral disc cause stress across the facet joint, impingement on neural structures, and strain on paraspinal muscles from loss of alignment. Degenerative disc disease can occur at any point across the spine; however it is most common in the cervical and lumbar regions causing neck and back pain, respectively. Although disabling, the majority of patients experience gradual resolution of symptoms without need for surgical intervention.

There are two common procedures for addressing a degenerative disc between two adjacent vertebrae. One procedure is to fuse the adjacent vertebrae. A second procedure is to insert an artificial disc between the adjacent vertebrae.

In spinal fusion surgery there are several different anatomic approaches to the spine. Some of these include posterior, lateral, or anterior approaches where the surgeon accesses the disc space directly. In inter-body fusion procedures, a portion of the disc space is cleared out and an inter-body device is inserted in its place. In addition, patients with osteopenia or osteoporosis have an increased risk of vertebral body fracture and graft subsidence and so vertebroplasty is occasionally performed in conjunction with the procedure. This can be done through fenestrated pedicle screws which act as a cannula through which to pass bone cement, or by placing a trocar directly into the vertebral body.

In the lumbar spine specifically, it is commonplace for the surgeon to also place pedicle screws from a posterior approach to increase stability of the construct. If the interbody is placed from an anterior or lateral approach, the posterior approach of the pedicle screws adds one or more additional incisions and makes the postoperative recovery more difficult for the patient. These pedicle screws add mechanical strength to the construct and help to hold the vertebrae stable relative to each other in order for the patient to grow bone connecting them and complete the fusion procedure.

Introduction of pedicle screws or other mechanical retention implements can introduce a number of potential issues. Initially, the mechanical retention implements introduce a potential source for infection. The use of mechanical retention implements can cause dural lesions and irritation of nerve roots resulting in revision surgeries. Other potential issues related to the use of mechanical retention implements include vascular injury, cerebrospinal fluid leak, visceral injury, pedicle fracture, screw migration, screw loosening, nerve injury, among other potential issues. The utilization of mechanical retention implements can cause localized pain, commonly described as a burning, sharp, aching, or radiating pain.

SUMMARY

The present disclosure generally relates to intervertebral members and methods of stabilizing bone and/or intervertebral members relative to each other using an injectable substance. More specifically, using a structural compound injected between two or more vertebrae and/or interbody implants in order to stabilize them. In some embodiments, the implant is an interbody device, an intervertebral cage (e.g., non-expandable cage, expandable cage), a corpectomy implant (e.g., single or multi-level corpectomy implant), an artificial disc, a cervical implant, a lumbar implant, fusion implant systems, non-fusion implant systems, or the like.

In some embodiments, a method of employing a bone reinforcing material to retain an intervertebral spacer in position between two adjacent vertebrae. The method can include the steps of placing the intervertebral spacer in position between two adjacent vertebrae. A cannula is inserted (a) through one vertebra of the two adjacent vertebrae and at least penetrating into the intervertebral spacer and/or (b) through the intervertebral spacer and at least penetrating one vertebra of the two adjacent vertebrae. A volume of a bone reinforcement composition is dispensed through the cannula. The cannula is withdrawn while dispensing the volume of a bone reinforcement composition from the cannula during the withdrawing process into each of the respective one vertebra of the two adjacent vertebrae and the intervertebral space. A volume of a bone reinforcement composition is dispensed into at least one of the respective adjacent intervertebral member and vertebrae. The cannula is then removed.

In a second aspect, the method further comprising a step of the bone reinforcement composition setting, wherein the set bone reinforcement composition anchors the intervertebral spacer in situ between the two adjacent vertebrae.

In another aspect, the bone reinforcement composition is defined as a family of materials that consist of a powder phase and a liquid phase which, after mixing, forms a plastic paste which has the ability to self-set once implanted in the body.

In another aspect, the bone reinforcement composition is a bone cement.

In another aspect, the bone reinforcement composition is a reabsorbable structural compound.

In another aspect, the bone reinforcement composition is a bone graft material.

In another aspect, the bone cement is also known as polymethyl methacrylate (PMMA).

In yet another aspect, the apparatus associated with the method is an interbody device comprising at least one integral bone delivery guide feature configured to allow the introduction of a bone cement composition along a respective trajectory.

In yet another aspect, the bone reinforcement composition retains the intervertebral spacer allowing natural fusion between the two adjacent vertebrae.

In yet another aspect, the bone reinforcement composition can limit, suppress, or eliminate any reliance on the bone reinforcement composition for retaining the intervertebral spacer in situ between the two adjacent vertebrae.

In yet another aspect, the method includes a step of inserting a cannula through one vertebra of the two adjacent vertebrae and at least penetrating into the intervertebral spacer.

In yet another aspect, the method includes a step of inserting a cannula through the intervertebral spacer and penetrating one vertebra of the two adjacent vertebrae.

In yet another aspect, the apparatus associated with the method is an interbody device comprising a plurality of integral bone delivery guide features that allow introduction of a bone cement composition along multiple trajectories.

In yet another aspect, the method includes a step of inserting a cannula through the intervertebral spacer and penetrating a second vertebra of the two adjacent vertebrae.

In yet another aspect, the method further comprising a step of inserting a cannula guide instrument into the position for dispensing the bone reinforcement composition and passing a cannula through the cannula guide instrument for dispensing the bone reinforcement composition therethrough.

In yet another aspect, the method further comprising a step of inserting a cannula guide instrument into the position for dispensing the bone reinforcement composition and passing a cannula through the cannula guide instrument for dispensing the bone reinforcement composition therethrough, wherein the cannula guide instrument is linear.

In yet another aspect, the method further comprising a step of inserting a cannula guide instrument into the position for dispensing the bone reinforcement composition and passing a cannula through the cannula guide instrument for dispensing the bone reinforcement composition therethrough, wherein the cannula guide instrument includes a section having an arch.

In yet another aspect, the cannula guide instrument remains implanted with the interbody device.

In some embodiments, a method of injecting a bone reinforcing material into a vertebra, the method comprising steps of:

inserting a cannula guide instrument into a vertebra;

inserting a curved directional composition delivery cannula instrument through the cannula guide instrument and into a vertebra;

continuing insertion of the curved directional composition delivery cannula instrument through the cannula guide instrument using a curved distal end of the curved directional composition delivery cannula instrument to guide the end through the vertebra and into an adjacent intervertebral member, wherein a direction of a path of the curved directional composition delivery cannula instrument is controlled by rotating the curved directional composition delivery cannula instrument and applying an insertion force thereto;

withdrawing the curved directional composition delivery cannula instrument a small distance; and dispensing a volume of a bone reinforcement composition into at least one of the respective adjacent intervertebral member and vertebrae covering the small distance.

In a second aspect, the cannula guide instrument includes a linear tubular element.

In another aspect, the cannula guide instrument includes a linear tubular element, wherein the linear tubular element is of a sufficient strength to penetrate bone.

In yet another aspect, the cannula guide instrument includes a linear tubular element extending from an instrument handle, wherein the instrument handle further comprising a passageway that is continuous with an interior passageway of the linear tubular element.

In yet another aspect, the cannula guide instrument includes a linear tubular element extending from an instrument handle, wherein the instrument handle is of a sufficient strength to endure multiple strikes from a mallet.

In yet another aspect, the cannula guide instrument includes a linear tubular element extending from an instrument handle. The instrument handle has a sufficient strength to endure multiple strikes from a mallet, the instrument handle further comprising a passageway that is continuous with an interior passageway of the linear tubular element.

In yet another aspect, the cannula guide instrument includes a linear tubular element extending from an instrument handle. The engagement interface is formed between the linear tubular element and the instrument handle is of a sufficient strength to endure multiple strikes from a mallet.

In yet another aspect, the curved directional composition delivery cannula instrument includes a flexible, curved tubular element.

In yet another aspect, the curved directional composition delivery cannula instrument includes a flexible, curved tubular element extending from an instrument handle.

In yet another aspect, the curved directional composition delivery cannula instrument includes a flexible, curved tubular element extending from an instrument handle. The instrument handle has a sufficient strength to endure multiple strikes from a mallet.

In yet another aspect, the curved directional composition delivery cannula instrument includes a flexible, curved tubular element extending from an instrument handle. The instrument handle has a sufficient strength to endure multiple strikes from a mallet, the instrument handle further comprising a passageway that is continuous with an interior passageway of the flexible, curved tubular element.

In yet another aspect, the curved directional composition delivery cannula instrument includes a flexible, curved tubular element extending from an instrument handle. The engagement interface is formed between the flexible, curved tubular element and the instrument handle is of a sufficient strength to endure multiple strikes from a mallet.

In yet another aspect, the curved directional composition delivery cannula instrument includes a flexible, curved tubular element. The flexible, curved tubular element has a sufficient strength to penetrate bone when partially supported by the cannula guide instrument.

In yet another aspect, the curved directional composition delivery cannula instrument includes a flexible, curved tubular element. The flexible, curved tubular element has a sufficient strength to penetrate bone.

In yet another aspect, the curved directional composition delivery cannula instrument includes an interface for mechanical coupling with a cement delivery system.

In yet another aspect, the instrument handle of the curved directional composition delivery cannula instrument includes an interface for mechanical coupling with a cement delivery system.

In yet another aspect, the interface for mechanical coupling with a cement delivery system is a threaded coupling.

In yet another aspect, the interface for mechanical coupling with a cement delivery system is a twist and lock coupling.

In yet another aspect, a location of the cannula guide instrument is guided by real time imaging equipment.

In yet another aspect, a location of the cannula guide instrument is guided by real time non-invasive imaging equipment.

In yet another aspect, a location of the cannula guide instrument is guided by real time non-invasive high definition imaging equipment.

In yet another aspect, a location of the cannula guide instrument is guided by real time non-invasive extreme definition imaging equipment.

In yet another aspect, a location of the cannula guide instrument is guided by real time non-invasive imaging equipment enabling imaging of an interior of a living being.

In yet another aspect, a location of the cannula guide instrument is guided by real time imaging equipment, wherein the real time imaging equipment employs an X-Ray.

In another aspect, a location of the cannula guide instrument is guided by real time imaging equipment, wherein the real time imaging equipment employs X-Ray imaging.

In another aspect, a location of the cannula guide instrument is guided by real time imaging equipment, wherein the real time imaging equipment includes a fluoroscope.

In another aspect, a location of the cannula guide instrument is guided by real time imaging equipment, wherein the real time imaging equipment includes an ultrasound imaging system.

In another aspect, a location of the cannula guide instrument is guided by real time imaging equipment, wherein the real time imaging equipment includes a sonogram imaging system.

In another aspect, a location of the cannula guide instrument is guided by real time imaging equipment, wherein the real time imaging equipment includes an echograph imaging system.

In another aspect, a location of the cannula guide instrument is guided by real time imaging equipment, wherein the real time imaging equipment includes a surgical navigation system.

In another aspect, the bone reinforcement composition is a cement.

In yet another aspect, the bone reinforcement composition is a bone cement.

In yet another aspect, the bone reinforcement composition is a nonstructural material that promotes bone growth.

In yet another aspect, the bone reinforcement composition is a structural material that promotes bone growth.

In yet another aspect, the bone reinforcement composition is a bone cement, wherein the bone cement is a two part mixture that is combined shortly prior to injection.

In yet another aspect, the mixed bone reinforcement composition is placed into a delivery system cartridge.

In yet another aspect, the bone reinforcement composition is a hydraulic cement.

In yet another aspect, the bone reinforcement composition is a hydraulic bone cement.

In yet another aspect, the bone reinforcement composition is a calcium phosphate bone cement.

In yet another aspect, the bone reinforcement composition is a bioactive glass impregnated calcium phosphate bone cement.

In yet another aspect, the bone reinforcement composition is a mesoporous bioactive glass impregnated calcium phosphate bone cement.

In yet another aspect, the bone reinforcement composition is an alginic acid calcium phosphate bone cement.

In yet another aspect, the bone reinforcement composition is an acrylic bone cement.

In yet another aspect, the bone reinforcement composition is a strontium containing hydroxyapatite bone cement.

In yet another aspect, the bone reinforcement composition is a zinc-based polyalkenoate bone cement.

In yet another aspect, the bone reinforcement composition is an Aluminum-free, zinc-based polyalkenoate bone cement.

In yet another aspect, the bone reinforcement composition is bone graft material.

In another aspect, the adjacent intervertebral member is a natural intervertebral disc.

In another aspect, the method further includes removing a natural intervertebral disc from between two adjacent vertebra and/or inserting a replacement intervertebral spacer between two adjacent vertebrae.

In another aspect, the adjacent intervertebral member is a manufactured intervertebral spacer.

In yet another aspect, the method further comprising a step of passing the curved directional composition delivery cannula instrument through the vertebra and into the intervertebral spacer.

In yet another aspect, the method further comprising a step of passing the curved directional composition delivery cannula instrument through the vertebra, continuing through the intervertebral spacer, and into the adjacent vertebrae.

In yet another aspect, the method further comprising a step of withdrawing the curved directional composition delivery cannula instrument from the intervertebral spacer in small increments and dispensing the bone reinforcing composition between steps of small incremental movements withdrawing the curved directional composition delivery cannula instrument.

In another embodiment, a method of employing a bone reinforcing material to retain an intervertebral spacer in position between two adjacent vertebrae, the method comprising steps of:

placing the intervertebral spacer in position between two adjacent vertebrae, the intervertebral spacer including at least one cannula guide directed towards a respective adjacent vertebra of the two adjacent vertebra;

inserting a cannula through one of the at least one cannula guide;

inserting the cannula into the respective adjacent vertebra of the two adjacent vertebra;

dispensing a volume of a bone reinforcement composition through the cannula;

withdrawing the cannula and dispensing the volume of a bone reinforcement composition from the cannula during the withdrawing process into each of the respective one vertebra of the two adjacent vertebrae and the intervertebral spacer; and dispensing a volume of a bone reinforcement composition into the respective adjacent vertebrae; and removing the cannula.

In yet another aspect, the method further comprising a step of mixing ingredients creating the bone reinforcement composition in a plastic paste state.

In yet another aspect, the step of withdrawing the cannula and dispensing the volume of a bone reinforcement composition is accomplished in repeating steps of withdrawing the cannula, stopping the withdrawal, and dispensing the volume of a bone reinforcement composition.

In yet another aspect, the step of withdrawing the cannula and dispensing the volume of a bone reinforcement composition is accomplished in repeating steps of withdrawing the cannula a short distance, stopping the withdrawal, and dispensing the volume of a bone reinforcement composition.

In yet another aspect, the intervertebral spacer comprising a first end wall, a second, opposite end wall, a first side wall and a second side wall.

In yet another aspect, the intervertebral spacer comprising a first end wall, a second, opposite end wall, a first side wall and a second side wall.

In yet another aspect, the intervertebral spacer comprising a first end wall, a second, opposite end wall, a first side wall, a second side wall and at least one traversing wall extending between the first side wall and the second side wall.

In yet another aspect, each at least one traversing wall extends substantially parallel to each of the first end wall and the second, opposite end wall.

In yet another aspect, each at least one traversing wall extends angularly between each of the first end wall and the second, opposite end wall.

In yet another aspect, the intervertebral spacer comprising a plurality of traversing wall members forming a matrix extending between the first end wall, the second, opposite end wall, the first side wall, and the second side wall.

In yet another aspect, the intervertebral spacer comprising a first end wall, a second, opposite end wall, a first side wall, a second side wall, a longitudinal wall extending between the first end wall and the second, opposite end wall, and at least one traversing wall extending between the first side wall and the longitudinal wall.

In yet another aspect, the intervertebral spacer comprising a first end wall, a second, opposite end wall, a first side wall, a second side wall, a top panel and a bottom panel.

In yet another aspect, the intervertebral spacer comprising a first end wall, a second, opposite second end wall, a first side wall, a second side wall, a top panel, a bottom panel, and at least one traversing wall extending between the first side wall and the second side wall.

In yet another aspect, the intervertebral spacer comprising a first end wall, a second, opposite end wall, a first side wall, a second side wall, a top panel, a bottom panel, a longitudinal wall extending between the first end wall and the second, opposite end wall, and at least one traversing wall extending between the first side wall and the longitudinal wall.

In yet another aspect, the intervertebral spacer comprising a first end wall, a second, opposite end wall, a first side wall, a second side wall, a top panel and a bottom panel, wherein at least one of the top panel and the bottom panel is porous.

In yet another aspect, the intervertebral spacer comprising a first end wall, a second, opposite end wall, a first side wall, a second side wall, a top panel and a bottom panel, wherein both the top panel and the bottom panel are porous.

In yet another aspect, the intervertebral spacer comprising a first end wall, a second, opposite end wall, a first side wall, and a second side wall, the first end wall, the second, opposite end wall, the first side wall, and the second side wall collectively form an enclosed spatial volume.

In yet another aspect, the intervertebral spacer comprising a first end wall, a second, opposite end wall, a first side wall, and a second side wall, the first end wall, the second, opposite end wall, the first side wall, and the second side wall collectively form an enclosed spatial volume for receiving a volume of a bone graft composition.

In yet another aspect, the intervertebral spacer comprising a first end wall, a second, opposite end wall, a first side wall, a second side wall, and a traversing wall extending between the first side wall and the second side wall, wherein one of the first end wall and the second, opposite end wall, along with the traversing wall, the first side wall, and the second side wall collectively form an enclosed spatial volume.

In yet another aspect, the intervertebral spacer comprising a first end wall, a second, opposite end wall, a first side wall, a second side wall, and a traversing wall extending between the first side wall and the second side wall, wherein one of the first end wall and the second, opposite end wall, along with the traversing wall, the first side wall, and the second side wall collectively form an enclosed spatial volume for receiving a volume of a bone graft composition.

In yet another aspect, the intervertebral spacer comprising a first end wall, a second, opposite end wall, a first side wall, a second side wall, a first traversing wall extending between the first side wall and the second side wall, and a second traversing wall extending between the first side wall and the second side wall, wherein the first traversing wall, the second traversing wall, the first side wall, and the second side wall collectively form an enclosed spatial volume.

In yet another aspect, the intervertebral spacer comprising a first end wall, a second, opposite end wall, a first side wall, a second side wall, a first traversing wall extending between the first side wall and the second side wall, and a second traversing wall extending between the first side wall and the second side wall, wherein the first traversing wall, the second traversing wall, the first side wall, and the second side wall collectively form an enclosed spatial volume for receiving a volume of a bone graft composition.

In yet another aspect, the intervertebral spacer comprising a first end wall, a second, opposite end wall, a first side wall, a second side wall, a longitudinal wall extending between the first end wall and the second, opposite end wall, wherein the first end wall, a second, opposite end wall, the longitudinal wall, and one of the first side wall and the second side wall collectively form an enclosed spatial volume.

In yet another aspect, the intervertebral spacer comprising a first end wall, a second, opposite end wall, a first side wall, a second side wall, and a longitudinal wall extending between the first end wall and the second, opposite end wall, wherein the first end wall, a second, opposite end wall, the longitudinal wall, and one of the first side wall and the second side wall collectively form an enclosed spatial volume for receiving a volume of a bone graft composition.

In yet another aspect, the intervertebral spacer comprising a first end wall, a second, opposite end wall, a first side wall, a second side wall, a longitudinal wall extending between the first end wall and the second, opposite end wall, and at least one traversing wall extending between one of the first side wall and the second side wall and the longitudinal wall, wherein the at least one traversing wall, the longitudinal wall, a respective one of the first end wall and a second, opposite end wall, and a respective one of the first side wall and the second side wall collectively form an enclosed spatial volume.

In yet another aspect, the intervertebral spacer comprising a first end wall, a second, opposite end wall, a first side wall, a second side wall, a longitudinal wall extending between the first end wall and the second, opposite end wall, and at least one traversing wall extending between one of the first side wall and the second side wall and the longitudinal wall, wherein the at least one traversing wall, the longitudinal wall, a respective one of the first end wall and a second, opposite end wall, and a respective one of the first side wall and the second side wall collectively form an enclosed spatial volume for receiving a volume of a bone graft composition.

In yet another aspect, the intervertebral spacer comprising a first end wall, a second, opposite end wall, a first side wall, a second side wall, a longitudinal wall extending between the first end wall and the second, opposite end wall, a first traversing wall extending between one of the first side wall and the second side wall and the longitudinal wall, and a second traversing wall extending between one of the first side wall and the second side wall and the longitudinal wall, wherein the first traversing wall, the second traversing wall, the longitudinal wall, and a respective one of the first side wall and the second side wall collectively form an enclosed spatial volume.

In yet another aspect, the intervertebral spacer comprising a first end wall, a second, opposite end wall, a first side wall, a second side wall, a longitudinal wall extending between the first end wall and the second, opposite end wall, a first traversing wall extending between one of the first side wall and the second side wall and the longitudinal wall, and a second traversing wall extending between one of the first side wall and the second side wall and the longitudinal wall, wherein the first traversing wall, the second traversing wall, the longitudinal wall, and a respective one of the first side wall and the second side wall collectively form an enclosed spatial volume for receiving a volume of a bone graft composition.

In yet another aspect, the orientation of any of the above described arrangements of the intervertebral spacer can be rotated 90 degrees where the traversing wall extends between the first end wall and the second end wall.

In yet another aspect, the orientation of any of the above described arrangements of the intervertebral spacer can be rotated 90 degrees where the longitudinal wall extends between the first side wall and the second side wall.

In yet another aspect, the orientation of any of the above described arrangements of the intervertebral spacer can be rotated 90 degrees from the orientations described above, wherein the traversing wall extends between the first end wall and the second end wall and the longitudinal wall extends between the first side wall and the second side wall.

In yet another aspect, the intervertebral spacer includes a first cannula guide directed towards a first respective adjacent vertebra of the two adjacent vertebrae and a second cannula guide directed towards a second, opposing adjacent vertebra of the two adjacent vertebrae.

In yet another aspect, the intervertebral spacer includes a first cannula guide directed towards the first respective adjacent vertebra of the two adjacent vertebrae and at least one second cannula guide directed towards the second, opposing adjacent vertebra of the two adjacent vertebrae.

In yet another aspect, the intervertebral spacer includes a first cannula guide directed towards the first respective adjacent vertebra of the two adjacent vertebrae in a first lateral direction and a second cannula guide directed towards the same first respective adjacent vertebra of the two adjacent vertebrae in a second lateral direction.

In yet another aspect, the intervertebral spacer includes a first cannula guide directed towards the first respective adjacent vertebra of the two adjacent vertebrae in a first lateral direction and a second cannula guide directed towards the same first respective adjacent vertebra of the two adjacent vertebrae in a second, different lateral direction.

In yet another aspect, the intervertebral spacer includes a first cannula guide directed towards the first respective adjacent vertebra of the two adjacent vertebrae in a first lateral direction towards a first side thereof and a second cannula guide directed towards the same first respective adjacent vertebra of the two adjacent vertebrae in a second lateral direction towards a second, opposite side thereof.

In yet another aspect, the intervertebral spacer includes a first cannula guide directed towards the first respective adjacent vertebra of the two adjacent vertebrae in a first lateral direction; a second cannula guide directed towards the same first respective adjacent vertebra of the two adjacent vertebrae in a second, different lateral direction; a third cannula guide directed towards the second, opposing respective adjacent vertebra of the two adjacent vertebrae in the first lateral direction; and a fourth cannula guide directed towards the same second, opposing respective adjacent vertebra of the two adjacent vertebrae in the second, different lateral direction.

In yet another aspect, the intervertebral spacer includes a first cannula guide directed towards the first respective adjacent vertebra of the two adjacent vertebrae in the first lateral direction; a second cannula guide directed towards the same first respective adjacent vertebra of the two adjacent vertebrae in a second, opposite lateral direction; a third cannula guide directed towards the second, opposing respective adjacent vertebra of the two adjacent vertebrae in the first lateral direction; and a fourth cannula guide directed towards the same second, opposing respective adjacent vertebra of the two adjacent vertebrae in a second, opposite lateral direction.

In yet another aspect, the intervertebral spacer includes a first cannula guide directed towards the first respective adjacent vertebra of the two adjacent vertebrae in a first lateral direction towards a first side thereof; a second cannula guide directed towards the same first respective adjacent vertebra of the two adjacent vertebrae in a second, lateral direction towards a second side thereof; a third cannula guide directed towards the second, opposing respective adjacent vertebra of the two adjacent vertebrae in the first lateral direction towards the first side thereof; and a fourth cannula guide directed towards the same second, opposing respective adjacent vertebra of the two adjacent vertebrae in a second, lateral direction towards the second, opposite side thereof.

In yet another aspect, intervertebral spacer includes a cement intercalation chamber and a graft chamber.

In yet another aspect, intervertebral spacer includes a cement intercalation chamber and a graft chamber, wherein the cement intercalation chamber and the graft chamber are isolated from one another.

In yet another aspect, intervertebral spacer includes a cement intercalation chamber and a graft chamber, wherein the cement intercalation chamber and the graft chamber are separated from one another by a common panel.

In yet another aspect, an initial guiding passageway guides the cannula to a desired target location.

In yet another aspect, an initial guiding passageway guides the cannula to a desired target location at an endplate of a respective vertebra.

In yet another aspect, an initial guiding passageway enables access for the cannula to at least two different passageways.

In yet another aspect, an initial guiding passageway enables access for the cannula to at least two different passageways to two distinct desired target locations.

In yet another aspect, an initial guiding passageway enables access for the cannula to at least two different passageways, wherein each of the at least two different passageways is provided to guide the cannula in a different direction.

In yet another aspect, an initial guiding passageway enables access for the cannula to at least two different passageways, wherein a shape of the cannula is provided to guide the cannula in a desired direction.

In yet another aspect, an initial guiding passageway enables access for the cannula to at least two different passageways, wherein a shape of the cannula is provided to guide the cannula in a desired direction towards a selected passageway of the at least two different passageways.

In yet another aspect, an initial guiding passageway enables access for the cannula to at least two different passageways, wherein a curved shape of the cannula is provided to guide the cannula in a desired direction towards a selected passageway of the at least two different passageways.

In yet another aspect, an initial guiding passageway enables access for the cannula to at least two different passageways, wherein a shape of the cannula guide instrument is provided to guide the cannula guide instrument in a desired direction towards a selected passageway of the at least two different passageways.

In yet another aspect, an initial guiding passageway enables access for the cannula to at least two different passageways, wherein a curved shape of the cannula guide instrument is provided to guide the cannula guide instrument in a desired direction towards a selected passageway of the at least two different passageways.

In yet another aspect, an initial guiding passageway includes a guide feature for directing the cannula to a selected passageway of the at least two different passageways provided to guide the cannula in a different direction.

In yet another aspect, an initial guiding passageway includes a guide feature for directing the non-linear cannula to a selected passageway of the at least two different passageways provided to guide the cannula in a different direction, wherein the non-linear shape of the cannula aids in guiding the cannula in a desired direction towards the selected passageway.

In yet another aspect, the intervertebral spacer includes a pair of end members, wherein the initial guiding passageway passes through one end member of the pair of end members.

In yet another aspect, the intervertebral spacer includes a pair of end members, wherein the initial guiding passageway passes through one end member of the pair of end members at a location proximate a center of the respective end member.

In yet another aspect, the intervertebral spacer includes a pair of end members, wherein the initial guiding passageway passes through one end member of the pair of end members at a location offset from the center of the respective end member in a lateral direction.

In yet another aspect, the intervertebral spacer includes a pair of end members, wherein the initial guiding passageway passes through one end member of the pair of end members at a location offset from the center of the respective end member in a normal direction.

In yet another aspect, the intervertebral spacer includes at least one cross member located between the pair of end members, a second passageway passing through one or more of the at least one cross member, the second passageway in alignment with the initial guiding passageway passing through the one end member of the pair of end members.

In yet another aspect, the intervertebral spacer includes at least one cross member located between the pair of end members, a second passageway passing through one or more of the at least one cross member, the second passageway in alignment with the initial guiding passageway passing through the one end member of the pair of end members, wherein the second passageway is oriented to guide the cannula towards and through an endplate of the respective vertebra. The cannula can be sufficiently rigid to pierce the endplate. In some embodiments, the cannula is delivered through a pre-formed hole in the endplate.

In yet another aspect, the intervertebral spacer includes at least one cross member located between the pair of end members, a second passageway passing through one or more of the at least one cross member, the second passageway in alignment with the initial guiding passageway passing through the one end member of the pair of end members, wherein the second passageway is oriented to guide the cannula towards an endplate of a first respective adjacent vertebra and a third passageway passing through the one or more of the at least one cross member, the third passageway in alignment with the initial guiding passageway passing through the one end member of the pair of end members, wherein the third passageway is oriented to guide the cannula towards an endplate of a second, opposite respective adjacent vertebra.

In yet another aspect, the intervertebral spacer includes at least one cross member located between the pair of end members, a second passageway passing through one or more of the at least one cross member, the second passageway in alignment with the initial guiding passageway passing through the one end member of the pair of end members, wherein the second passageway is oriented to guide the cannula towards a first location in the endplate of the first respective adjacent vertebra and a third passageway passing through the one or more of the at least one cross member, the third passageway in alignment with the initial guiding passageway passing through the one end member of the pair of end members, wherein the third passageway is oriented to guide the cannula towards a second location in the endplate of the same, first respective adjacent vertebra.

In yet another aspect, the intervertebral spacer includes at least one cross member located between the pair of end members, a second passageway passing through one or more of the at least one cross member, the second passageway in alignment with the initial guiding passageway passing through the one end member of the pair of end members, wherein the second passageway is oriented to guide the cannula towards a first location in the endplate of the first respective adjacent vertebra; third passageway passing through one or more of the at least one cross member, the third passageway in alignment with the initial guiding passageway passing through the one end member of the pair of end members, wherein the third passageway is oriented to guide the cannula towards a first location in the endplate of an opposing, second respective adjacent vertebra; a fourth passageway passing through the one or more of the at least one cross member, the fourth passageway in alignment with the initial guiding passageway passing through the one end member of the pair of end members, wherein the fourth passageway is oriented to guide the cannula towards a second location in the endplate of the first respective adjacent vertebra; and a fifth passageway passing through the one or more of the at least one cross member, the fifth passageway in alignment with the initial guiding passageway passing through the one end member of the pair of end members, wherein the fifth passageway is oriented to guide the cannula towards a second location in the endplate of the same, second respective adjacent vertebra.

In yet another aspect, at least one cannula guiding passageway is provided as a tubular member extending between one end wall and a second member.

In yet another aspect, the tubular member is perforated.

In yet another aspect, the tubular member is perforated for passage of the bone reinforcement composition.

In yet another aspect, the tubular member is perforated for passage of the bone reinforcement composition, wherein the perforations are in a direction towards a respective vertebra when the intervertebral spacer is inserted between adjacent vertebrae.

In yet another aspect, the tubular member is perforated for passage of the bone reinforcement composition, wherein the perforations are adjacent to and in a direction towards a respective vertebra when the intervertebral spacer is inserted between adjacent vertebrae.

In yet another aspect, the tubular member is perforated for passage of the bone graft composition.

In yet another aspect, the tubular member is perforated for passage of the bone reinforcement composition and bone graft composition.

In yet another aspect, at least one cannula guiding passageway is provided as a linear tubular member extending between one end wall and a second member.

In yet another aspect, at least one cannula guiding passageway is provided as an arched tubular member extending between one end wall and a second member.

In yet another aspect, at least one cannula guiding passageway is provided as a tubular member extending between one end wall and a second member, wherein the tubular member includes a linear segment.

In yet another aspect, at least one cannula guiding passageway is provided as a tubular member extending between one end wall and a second member, wherein the tubular member includes an arched segment.

In yet another aspect, at least one cannula guiding passageway is provided as a tubular member extending between one end wall and a second member, wherein the tubular member includes a linear segment and an arched segment.

In yet another aspect, at least one cannula guiding passageway is provided as a tubular member extending between one end wall and a traversing wall.

In yet another aspect, at least one cannula guiding passageway is provided as a tubular member extending between one end wall and an intermediate traversing wall located between a first end wall and a second, opposite end wall.

In yet another aspect, a first cannula guiding passageway is provided as a tubular member extending between one end wall and a second member, and a second cannula guiding passageway provided as a tubular member extending between the same end wall and the same second member.

In yet another aspect, a first cannula guiding passageway is provided as a tubular member extending between one end wall and a second member, the first cannula guiding passageway directed towards a first respective adjacent vertebra and a second cannula guiding passageway provided as a tubular member extending between the same end wall and the same second member, the second cannula guiding passageway directed towards the same, first respective adjacent vertebrae.

In yet another aspect, a first cannula guiding passageway is provided as a tubular member extending between one end wall and a second member, the first cannula guiding passageway directed towards a first respective adjacent vertebra and a second cannula guiding passageway provided as a tubular member extending between the same end wall and the same second member, the second cannula guiding passageway directed towards the second, opposing respective adjacent vertebrae.

In yet another aspect, a first cannula guiding passageway is provided as a tubular member extending between one end wall and a second member, and a second cannula guiding passageway provided as a tubular member extending between the same end wall and the same second member, wherein the second member is a traversing wall.

In yet another aspect, a first cannula guiding passageway is provided as a tubular member extending between one end wall and one of an upper panel and a lower panel.

In yet another aspect, a first cannula guiding passageway is provided as a tubular member extending between one end wall and the upper panel, and a second cannula guiding passageway provided as a tubular member extending between the same end wall and the upper panel.

In yet another aspect, a first cannula guiding passageway is provided as a tubular member extending between one end wall and the upper panel, and a second cannula guiding passageway provided as a tubular member extending between the same end wall and a lower panel.

In yet another aspect, a first cannula guiding passageway is provided as a tubular member extending between one end wall and the upper panel, the first cannula guiding passageway directed towards a first respective adjacent vertebra and a second cannula guiding passageway provided as a tubular member extending between the same end wall and the same upper panel, the second cannula guiding passageway directed towards the same, first respective adjacent vertebrae.

In yet another aspect, a first cannula guiding passageway is provided as a tubular member extending between one end wall and the upper panel, the first cannula guiding passageway directed towards the first respective adjacent vertebra and a second cannula guiding passageway provided as a tubular member extending between the same end wall and the lower panel, the second cannula guiding passageway directed towards the second, opposing respective adjacent vertebrae.

These and other aspects, features, and advantages of the present invention will become more readily apparent from the attached drawings and the detailed description of the preferred embodiments, which follow.

BRIEF DESCRIPTION OF THE DRAWINGS

The accompanying drawings illustrate various embodiments of systems, methods, and embodiments of various other aspects of the disclosure. Any person with ordinary skill in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another, and vice versa. Furthermore, elements may not be drawn to scale. Non-limiting and non-exhaustive descriptions are described with reference to the following drawings. The components in the figures are not necessarily to scale, emphasis instead being placed upon illustrating principles.

FIG. 21 presents a side sectioned elevation view of the exemplary intervertebral spacer originally introduced in FIG. 14 as installed between two adjacent vertebrae, the section being identified by section line 15-15 of FIG. 14, the illustration presenting a first exemplary step of inserting the cannula through an off-centered guide for dispensing bone reinforcing material to retain the exemplary intervertebral spacer in situ.

FIGS. 51-55 show an anchor in accordance with an embodiment of the technology.

Like reference numerals refer to like parts throughout the several views of the drawings.

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

The technology can include a delivery system configured to dispense one or more materials (e.g., a bone reinforcing material, medicant, etc.) into a first vertebra and preferably through a natural intervertebral disc or an intervertebral spacer, and into a second, adjacent vertebrae. A composition delivery system flow diagram 400, detailed in FIG. 13, and steps of FIGS. 13 and 74-76 for dispensing bone reinforcing material into tissue (e.g., vertebrae), with supporting drawings being presented in FIGS. 3 through 85.

Figure 1:
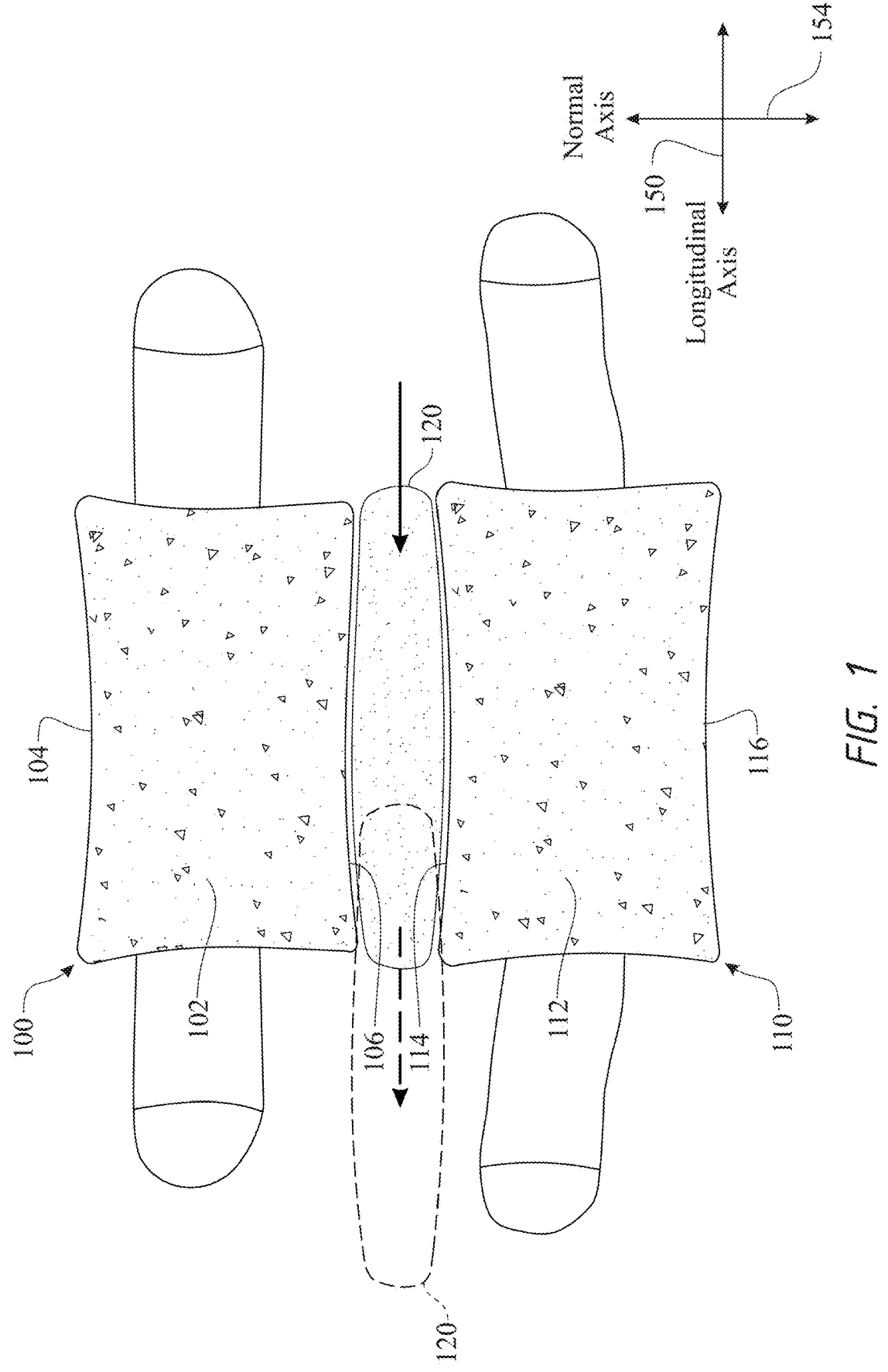
FIG. 1 presents a sectioned front elevation view of a step of removing an intervertebral disc from a space between two exemplary adjacent vertebrae.

FIG. 1 is a sectional front elevation view of a step of removing an intervertebral disc from a space between two exemplary adjacent vertebrae. An intervertebral joint comprises a first joint member 100 and a second joint member 110 having a natural intervertebral disc 120 provided therebetween. The exemplary first joint member 100 includes a first vertebra 102 having a first intervertebral disc contacting surface 104 on an upper surface and a second intervertebral disc contacting surface 106 on a lower surface. The exemplary second joint member 110 includes a second vertebra 112 having a first intervertebral disc contacting surface 114 on an upper surface and a second intervertebral disc contacting surface 116 on a lower surface. The second intervertebral disc contacting surface 106 of the first vertebrae 102 and the first intervertebral disc contacting surface 114 of the second vertebrae 112 face one another. The natural intervertebral disc 120 is located between the second intervertebral disc contacting surface 106 of the first vertebrae 102 and the first intervertebral disc contacting surface 114 of the second vertebrae 112.

Reference to an orientation of the first joint member 100 and the second joint member 110 can be provided by a longitudinal axis 150 and a normal axis 154 as illustrated. For future reference, orientations throughout include a longitudinal axis 150, a lateral axis 152, and a normal axis 154, where all three axes are introduced in FIG. 14.

The bone reinforcing composition delivery system flow diagram 400 initiates with a step of preparing the surgical site (block 410). This step can include common surgical preparations such as administration of anesthesia, placement of protective barriers, sterilization of the surgical site, creating an incision at the surgical site, and the like.

The procedure can optionally include a step of removing a defective natural intervertebral disc 120 from between facing vertebrae intervertebral disc contacting surfaces 106, 114 of adjacent vertebrae 102, 112, respectively of the joint 100, 110 (block 412), as illustrated in FIG. 1. The actual direction and method of the removal of the natural intervertebral disc 120 would be based upon the procedure.

Figure 2:
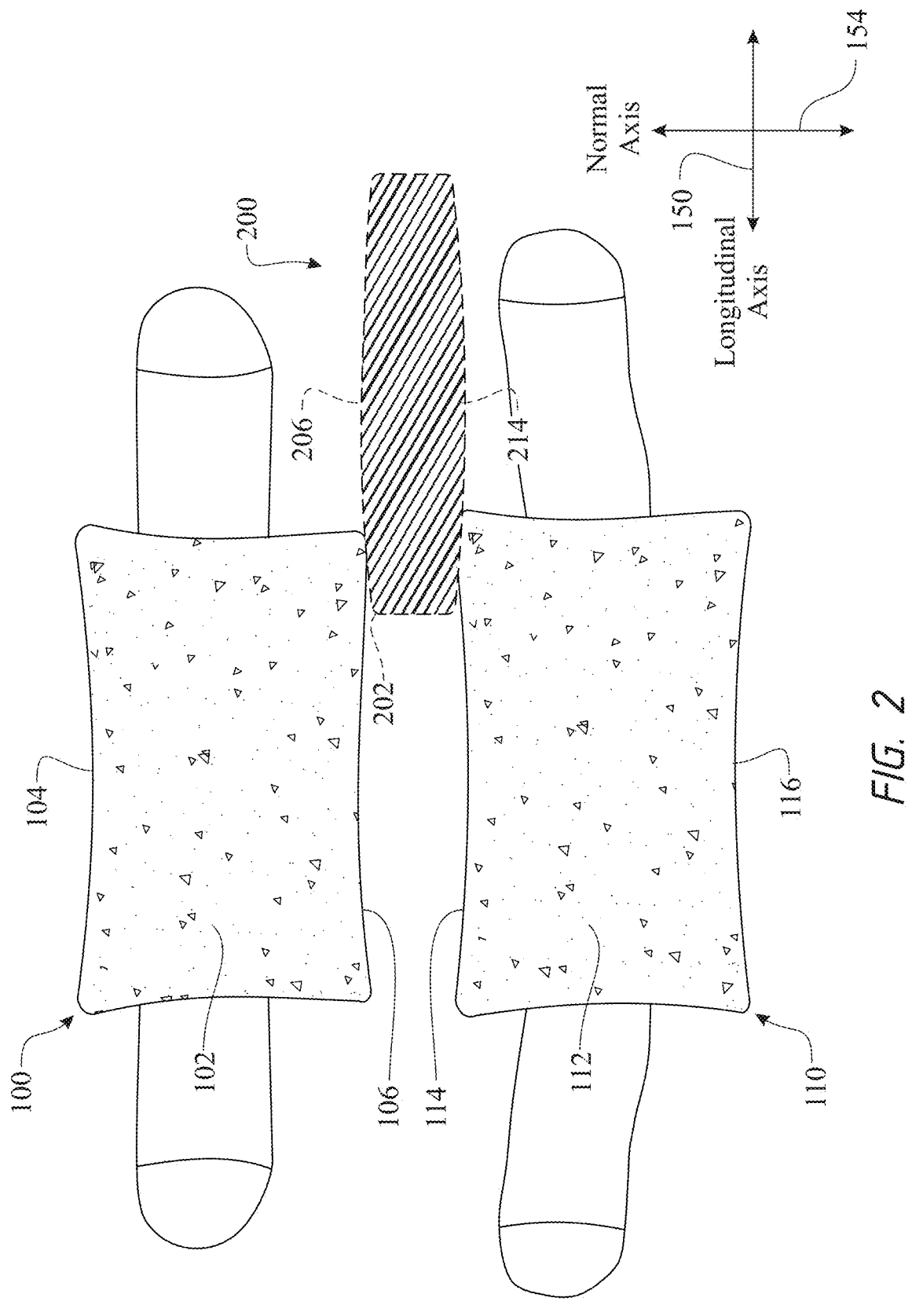
FIG. 2 presents a sectioned front elevation view of a step of inserting an intervertebral spacer into the space between the two exemplary adjacent vertebrae.

FIG. 2 shows an insertion of an intervertebral spacer into the space between the two exemplary adjacent vertebrae (block 414). A replacement intervertebral spacer body 202 of a selected replacement intervertebral spacer 200 is inserted between the adjacent vertebrae 102, 112 (block 420).

The replacement intervertebral spacer body 202 is representative of any suitable intervertebral body of any replacement intervertebral spacer 200. The replacement intervertebral spacer body 202 commonly includes an intervertebral spacer body upper vertebral contacting surface 206, designed to rest against the first vertebrae second intervertebral disc contacting surface 106 of the first vertebrae 102, an intervertebral spacer body lower vertebral contacting surface 214, designed to rest against the second vertebrae first intervertebral disc contacting surface 114 of the second vertebrae 112, and a pair of intervertebral spacer body side walls 208 extending between each respective elongated edges thereof. The replacement intervertebral spacer body 202 provides support to each of the first vertebrae 102 and the second vertebrae 112.

Alternatively, the natural intervertebral disc 120 can remain in place and the procedure can dispense the bone reinforcing composition into or through the natural intervertebral disc 120.

Figure 3:
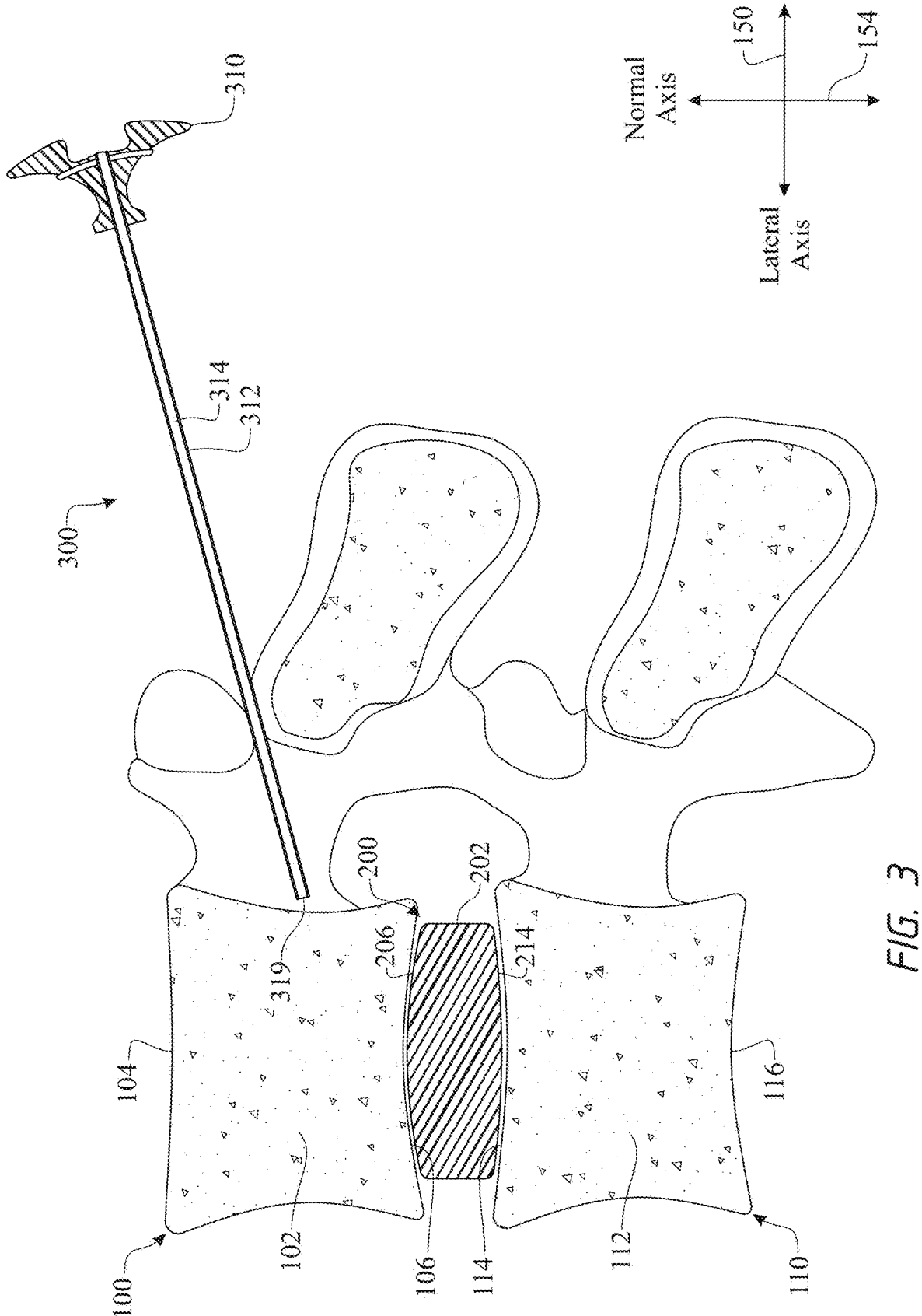
FIG. 3 presents a sectioned side elevation view introducing a cannula guide instrument being inserted into a first vertebra.
Figure 4:
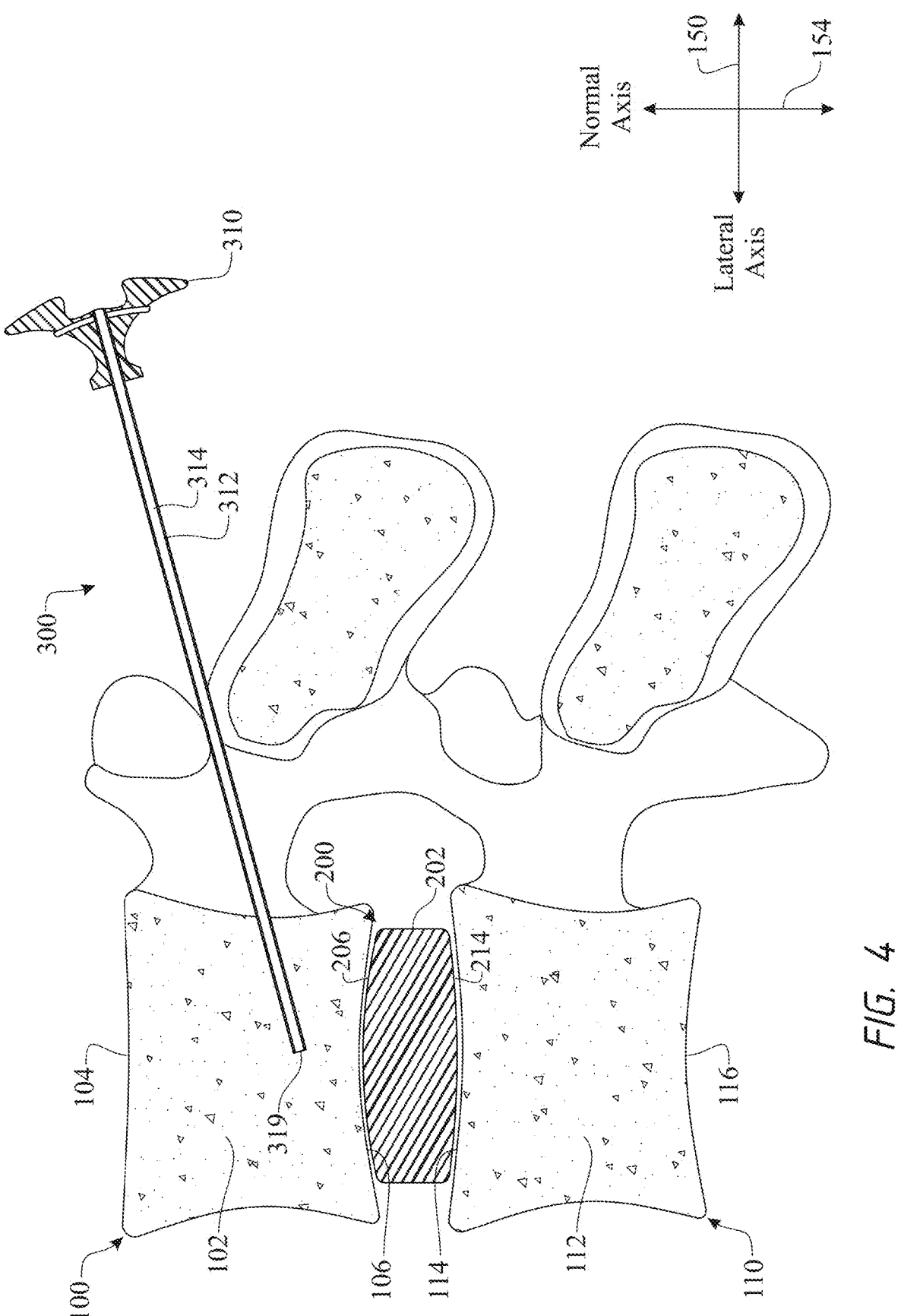
FIG. 4 presents a sectioned side elevation view of the cannula guide instrument originally introduced in FIG. 3, the cannula guide instrument being located within the first vertebra.

FIG. 3 is a side elevation view of a cannula guide instrument positioned for insertion into a first vertebra. FIG. 4 shows the cannula guide instrument with a distal end positioned within the first vertebra. Referring now to FIG. 3, the process employs a cannula guide instrument 300, a composition delivery cannula instrument 320 designed to pass through a cannula tubular guide instrument body interior passageway 314 of a cannula tubular guide instrument body 312 of the cannula guide instrument 300, and a bone reinforcement composition delivery system 350. The cannula guide instrument 300 includes a cannula tubular guide instrument body 312 extending from a cannula guide instrument handle 310. The cannula tubular guide instrument body 312 is tubular defining a cannula tubular guide instrument body interior passageway 314. The interface between the cannula guide instrument handle 310 and the cannula tubular guide instrument body 312 includes features to ensure that when the cannula guide instrument handle 310 is struck by a mallet (not shown but well understood by those skilled in the art), the force is transferred to the cannula tubular guide instrument body 312 without any slippage between the cannula guide instrument handle 310 and the cannula tubular guide instrument body 312.

Referring to FIGS. 3 and 4, the cannula tubular guide instrument body 312 is inserted into the first vertebrae 102 by holding the cannula guide instrument 300 at a desired location and angle, as illustrated in FIG. 4, and striking the cannula guide instrument handle 310 with the mallet or other similar instrument (block 420). The inserting location and orientation of the cannula tubular guide instrument body 312 can be monitored using a live imaging system, such as a fluoroscope (block 420). Alternatives to the fluoroscope can include an ultrasound imaging system, a sonogram imaging system, an echograph imaging system, or any other suitable live imaging system. Using the live imaging system enables the medical professional to determine and properly position the cannula tubular guide instrument body 312 for guiding the composition delivery cannula instrument 320 along a desired path and into a desired position.

Figure 5:
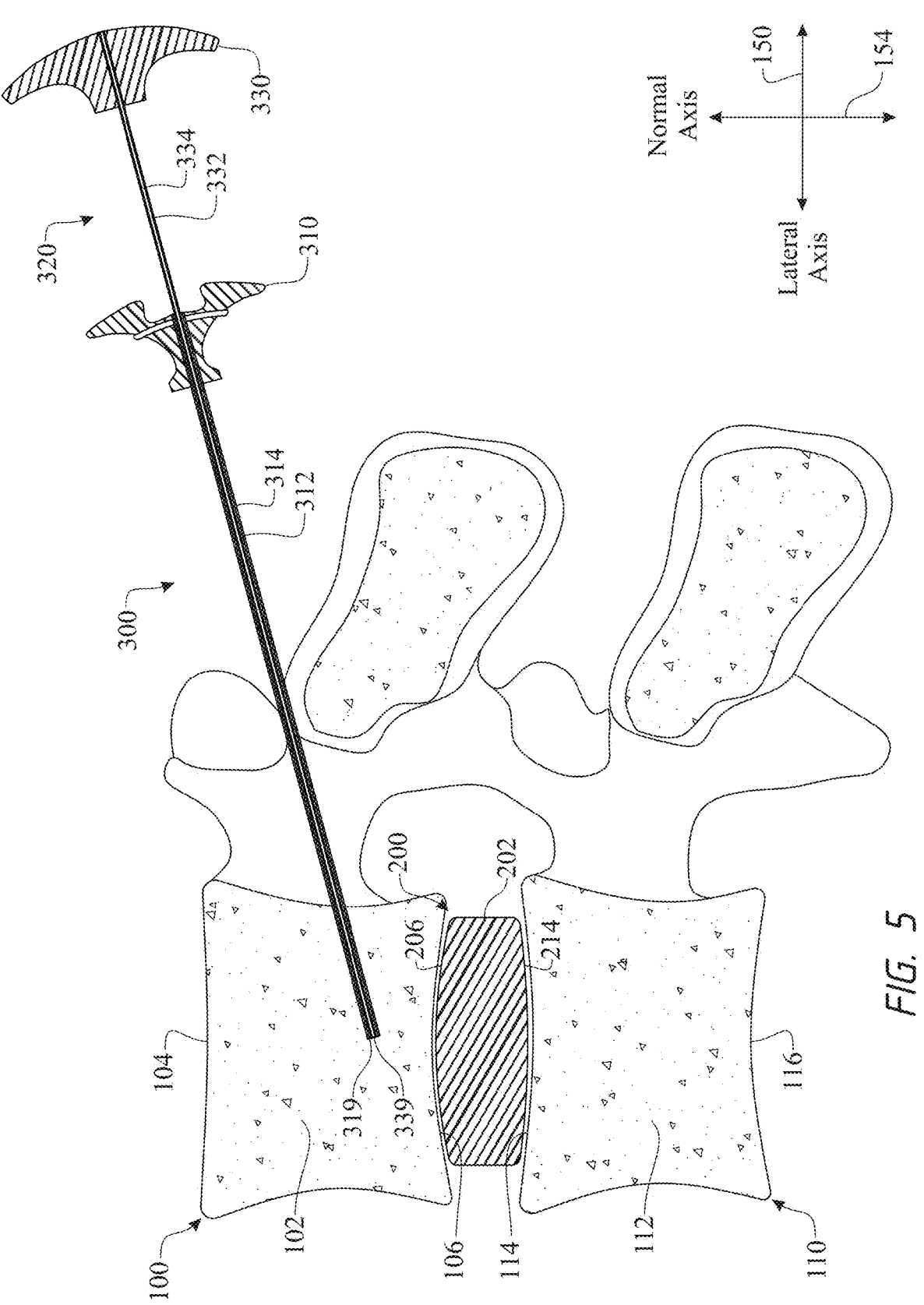
FIG. 5 presents a sectioned side elevation view introducing a directional composition delivery cannula instrument being inserted into the cannula guide instrument originally introduced in FIG. 3.

FIG. 5 shows the composition delivery cannula instrument being inserted into the cannula guide. Once the cannula guide instrument 300 is properly positioned, the composition delivery cannula body 332 of the composition delivery cannula instrument 320 is inserted into and slid through the cannula tubular guide instrument body interior passageway 314 of the cannula guide instrument 300 until a composition delivery cannula body distal end 339 of the composition delivery cannula body 332 reaches the cannula tubular guide instrument body distal end 319 of the cannula tubular guide instrument body 312 and contacts the bone of the first vertebrae 102, as illustrated in FIG. 5 (block 422).

Figure 6:
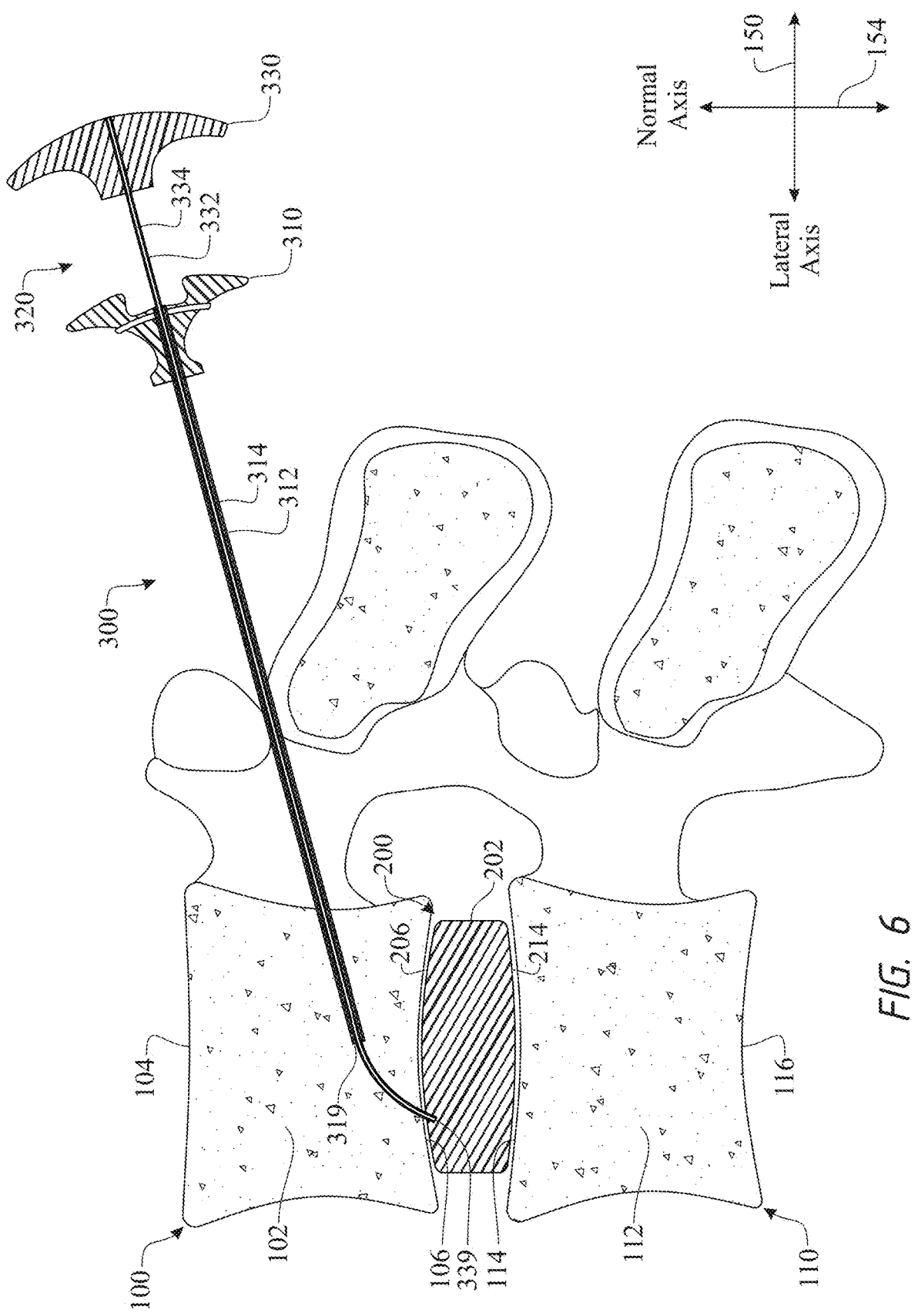
FIG. 6 presents a sectioned side elevation view illustrating the directional composition delivery cannula instrument originally introduced in FIG. 5.

A distal end of the composition delivery cannula body 332 is curved, as illustrated in FIGS. 6 through 10. FIG. 6 shows the composition delivery cannula instrument originally introduced in FIG. 5 partially inserted into the vertebra and continuing into the intervertebral spacer. The inserting direction of the directional composition delivery cannula instrument is determined by a rotation of the directional composition delivery cannula instrument in combination with a shape of a dispensing end portion of a body of the directional composition delivery cannula instrument, wherein a location of a dispensing end of the directional composition delivery cannula instrument is monitored by a non-invasive imaging system aiding the medical team is directing the insertion thereof. The curved section is flexible and straightens when located within the cannula tubular guide instrument body interior passageway 314 of the cannula guide instrument 300. It is preferred that the orientation of the curved portion of the composition delivery cannula body 332 be related to the orientation of the composition delivery cannula handle 330. In the illustrations, a plane defined by the curve of the composition delivery cannula body 332 is the same plane defined by a central plane of the composition delivery cannula handle 330. This can provide a reference of the orientation of the curved portion of the composition delivery cannula body 332 to the medical professional while the composition delivery cannula body 332 is concealed from view within the patient.

The medical professional can continue to insert the composition delivery cannula body 332 into the first vertebrae 102 by striking the composition delivery cannula handle 330 with a mallet or any other suitable instrument. The direction of travel of the composition delivery cannula body 332 is governed by rotating the composition delivery cannula handle 330 clockwise or counterclockwise to direct the curved portion of the composition delivery cannula body 332 accordingly. The actual location would be monitored by using the suitable real time imaging system previously used to assist in positioning of the cannula tubular guide instrument body 312 (block 424). The insertion of the composition delivery cannula body 332 continues until the composition delivery cannula body distal end 339 of the composition delivery cannula body 332 is at the desired location, as illustrated in FIG. 7.

At some point during the process, the bone reinforcement composition is prepared for insertion. The bone reinforcement composition is commonly a two-part or multi-part mixture. Commonly, one part of the bone reinforcement composition is a liquid and a second part of the bone reinforcement composition is a solid. The components of the bone reinforcement composition are placed within a mixing chamber and mixed in accordance with instructions provided by the manufacturer. Once mixed, the prepared bone reinforcement composition is commonly inserted into a composition delivery system cartridge.

Figure 7:
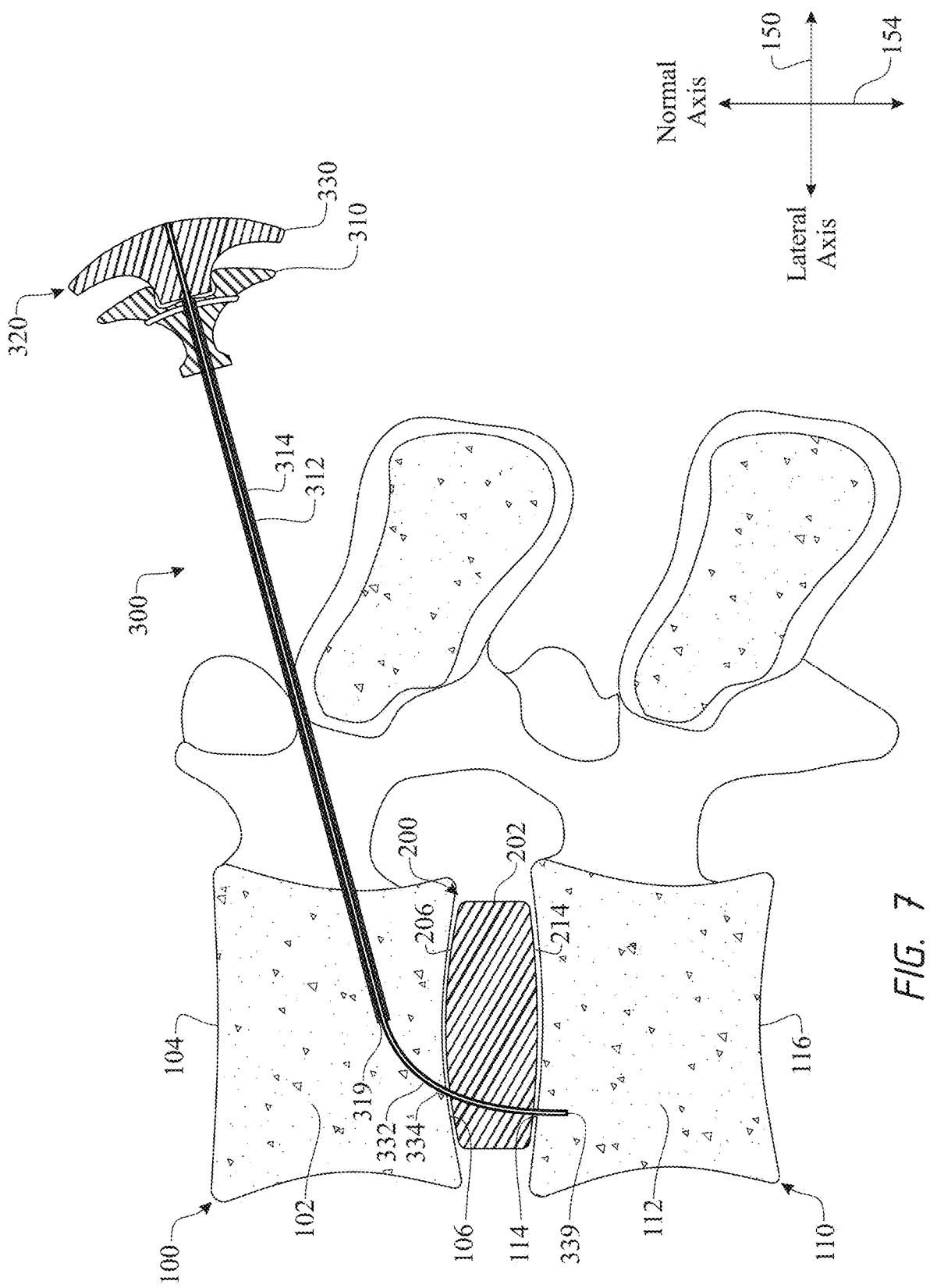
FIG. 7 presents a sectioned side elevation view illustrating the directional composition delivery cannula instrument originally introduced in FIG. 5 in a fully inserted position, wherein the dispensing end of the directional composition delivery cannula instrument passed through the first vertebra, the intervertebral spacer body, and into the adjacent vertebrae.

FIG. 7 is a side sectional elevation view illustrating the directional composition delivery cannula instrument originally introduced in FIG. 5 in a fully inserted position. The dispensing end of the directional composition delivery cannula instrument passed through the first vertebra, the intervertebral spacer body, and into the adjacent vertebrae. Once the composition delivery cannula body distal end 339 is properly located, the bone reinforcement composition delivery system 350 is connected to the composition delivery cannula handle 330 (block 430). The cartridge is commonly connected directly to the composition delivery cannula handle 330 and an end of a tube extending from a delivery gun is connected to the opposite end of the composition delivery system cartridge. The delivery gun precisely controls bone cement delivery up to 4 feet away from the radiation source and preferably includes a trigger that halts cement flow instantly.

A volume of delivered reinforcement composition 352 is dispensed into the track created within the bone of the vertebra 112, 102 through a composition delivery cannula body interior passageway 334 within the composition delivery cannula body 332. The process relies upon repeated cycles of withdrawing the composition delivery cannula body 332 over a short incremental distance, then dispensing an appropriate volume of the bone reinforcement material.

Figure 8:
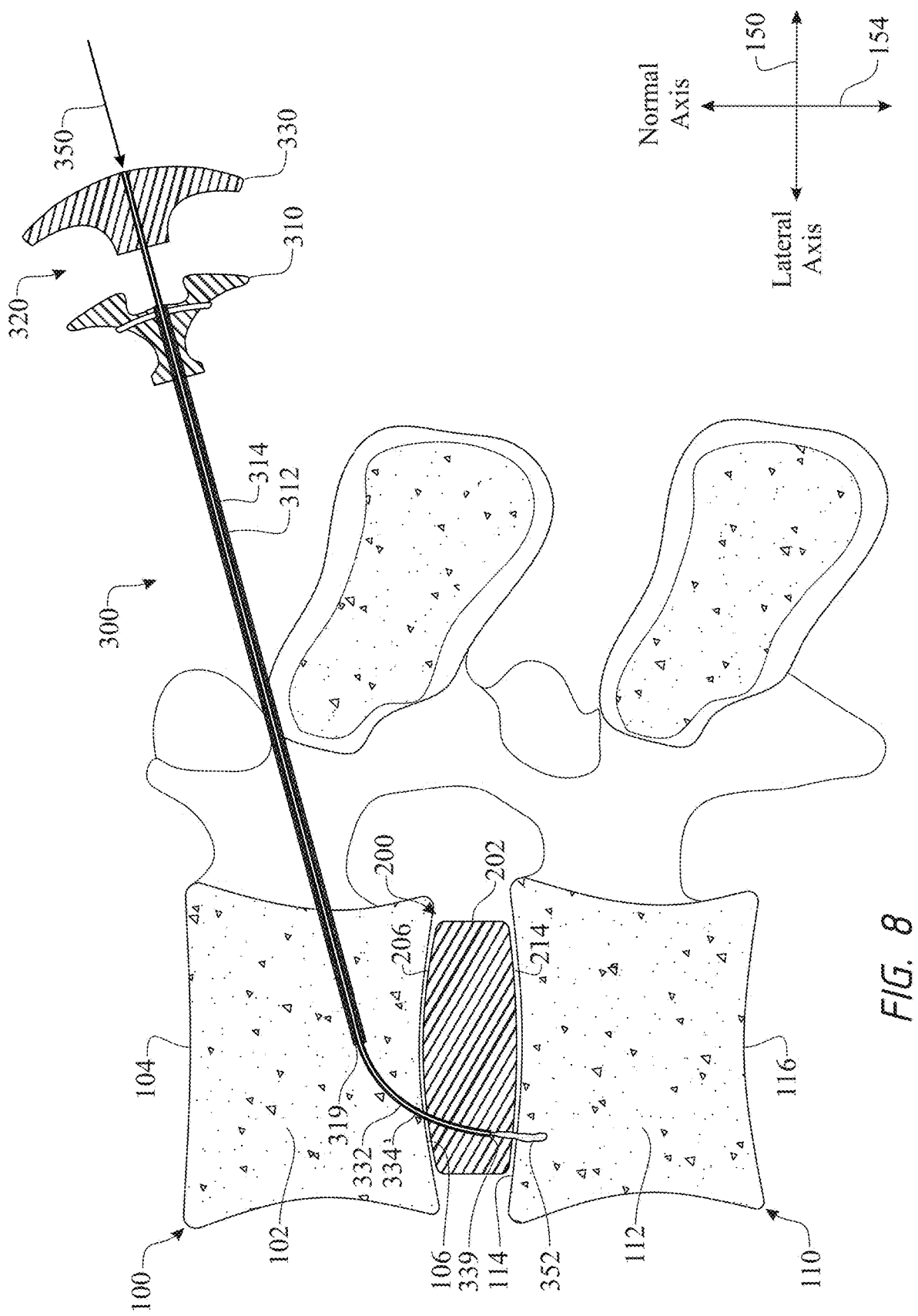
FIG. 8 presents a sectioned side elevation view illustrating the directional composition delivery cannula instrument originally introduced in FIG. 5 shown in a first incrementally withdrawn position and a volume of bone reinforcing material is being dispensed filling a track where the directional composition delivery cannula instrument has been withdrawn.
Figure 9:
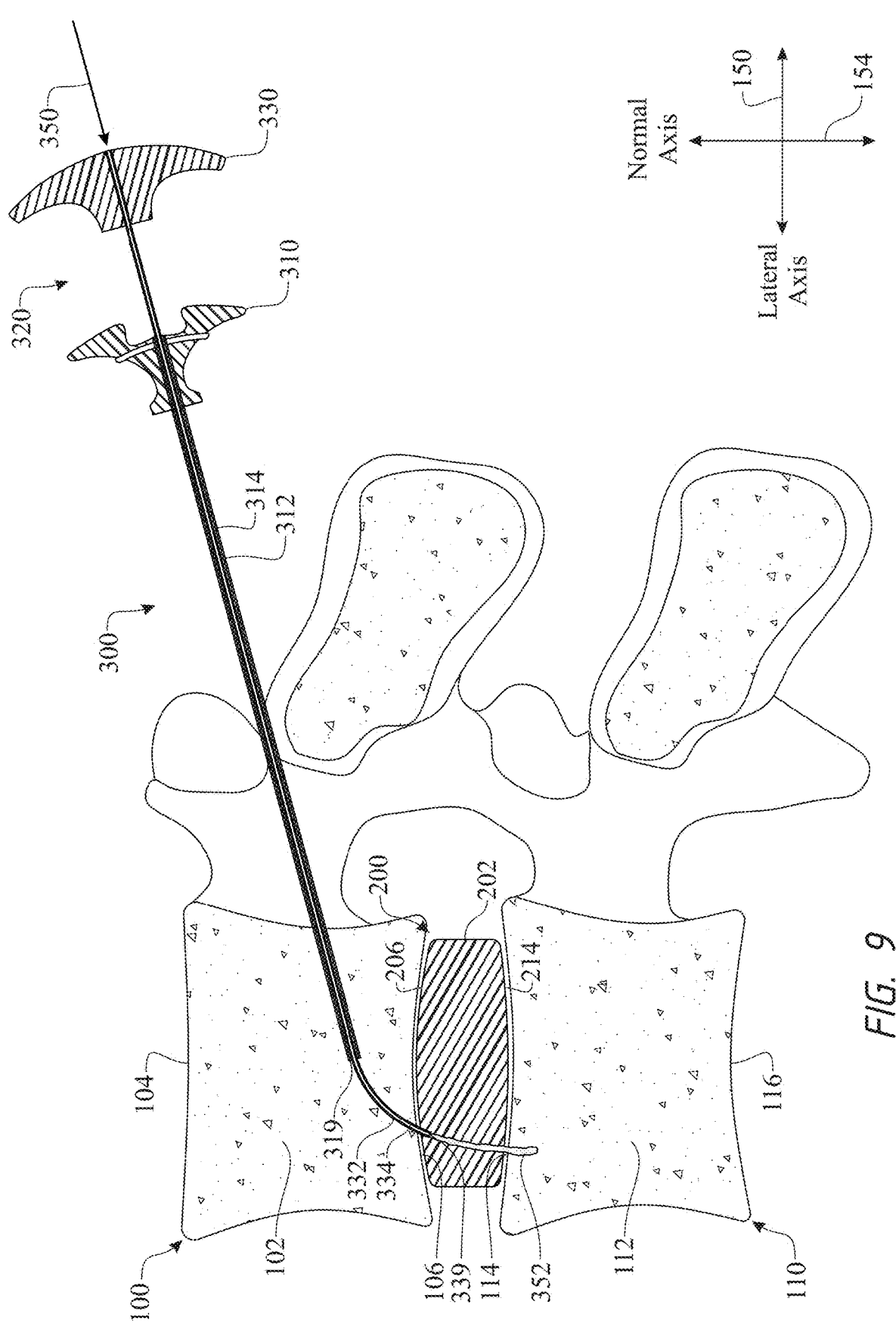
FIG. 9 presents a sectioned side elevation view illustrating the directional composition delivery cannula instrument originally introduced in FIG. 5 shown in a second incrementally withdrawn position and a volume of bone reinforcing material continues to be dispensed filling a track where the directional composition delivery cannula instrument has been withdrawn.
Figure 10:
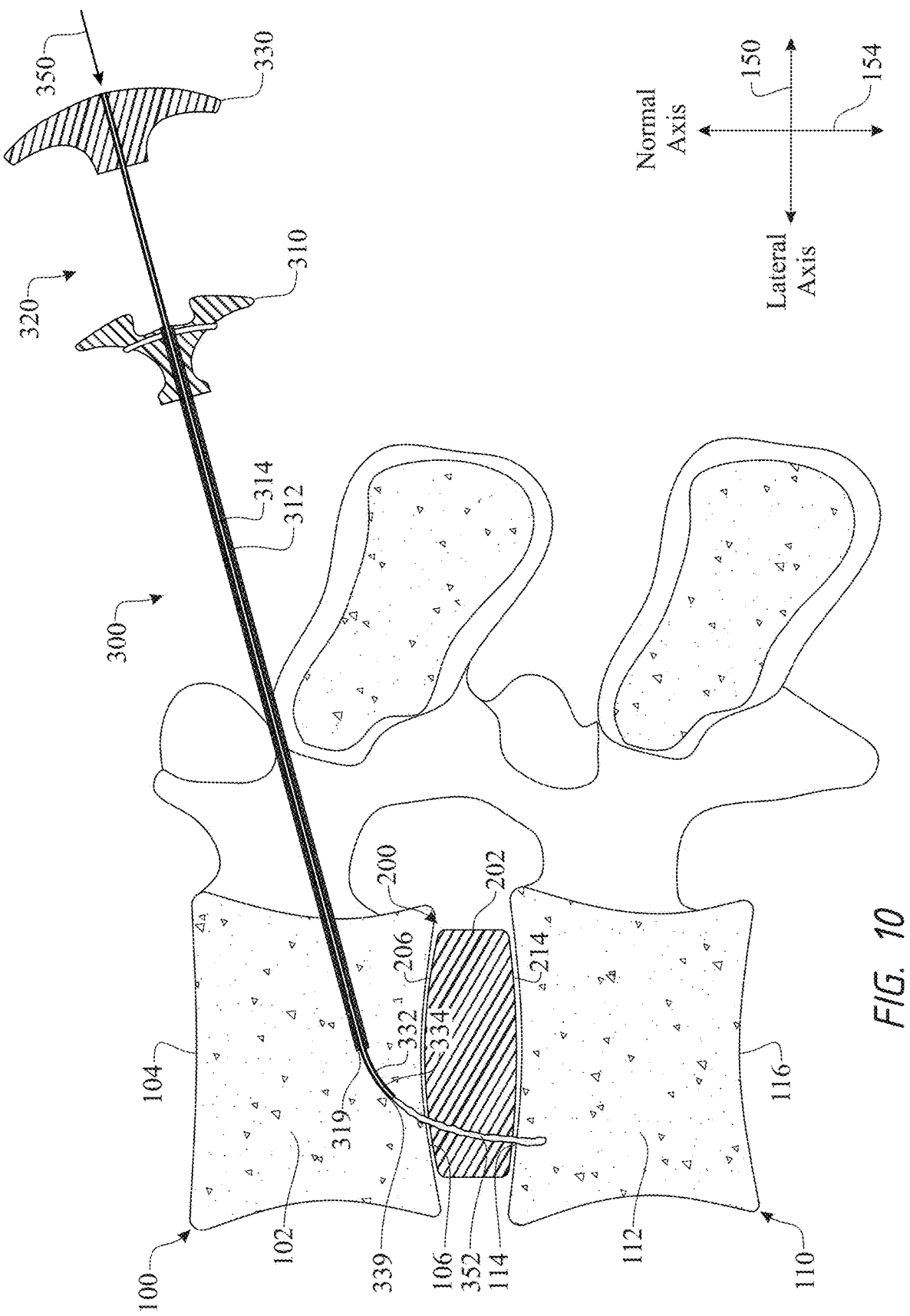
FIG. 10 presents a sectioned side elevation view illustrating the directional composition delivery cannula instrument originally introduced in FIG. 5 shown in a third incrementally withdrawn position and a volume of bone reinforcing material continues to be dispensed filling a track where the directional composition delivery cannula instrument has been withdrawn.
Figure 11:
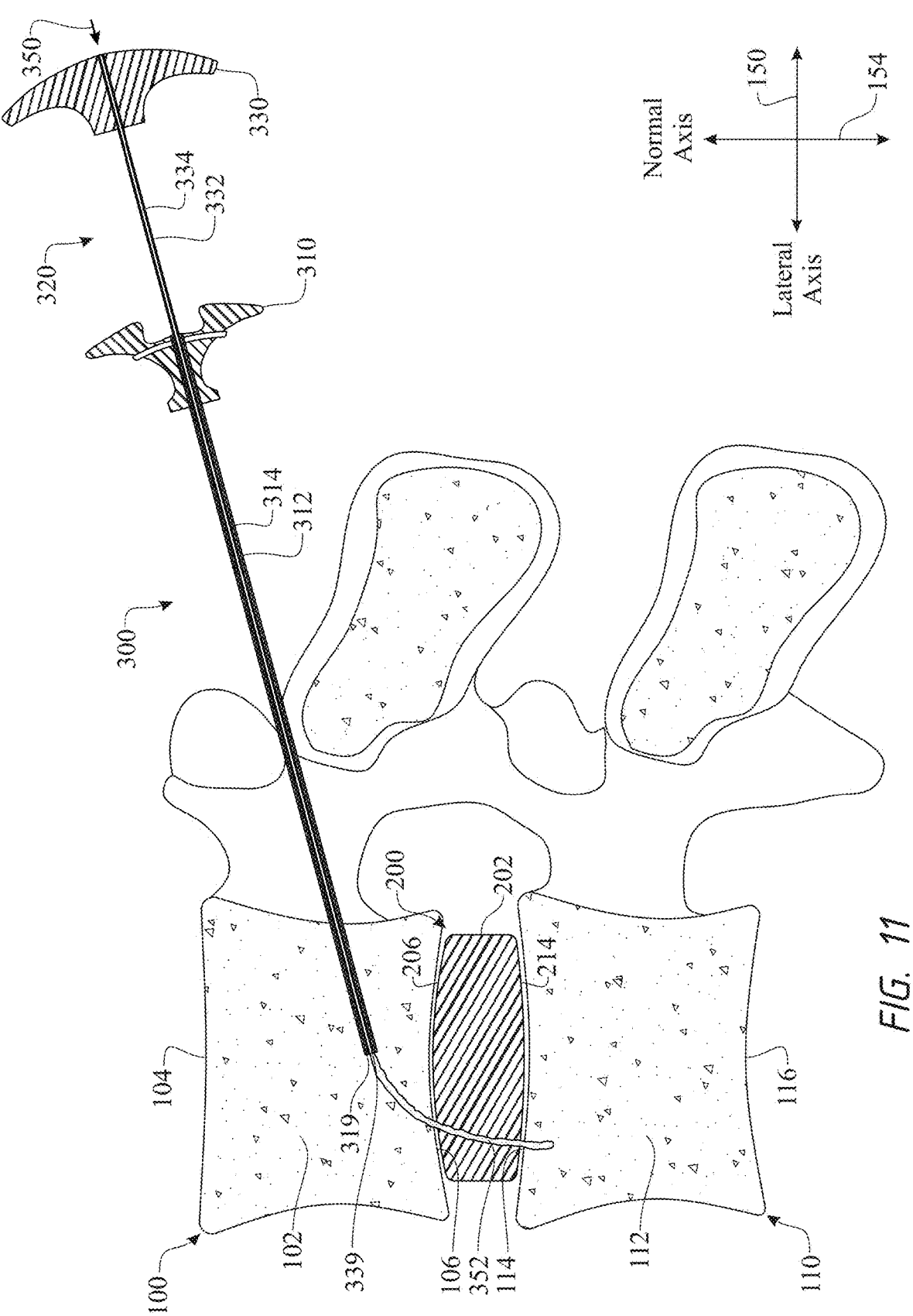
FIG. 11 presents a sectioned side elevation view illustrating the directional composition delivery cannula instrument originally introduced in FIG. 5 shown in a fourth incrementally and fully withdrawn position and a volume of bone reinforcing material continues to be dispensed filling a track where the directional composition delivery cannula instrument has been withdrawn.

The process relies upon repeated cycles of withdrawing the composition delivery cannula body 332 over a short incremental distance, then dispensing an appropriate volume of the bone reinforcement material to fill the void within the bone 102, 112 created by the composition delivery cannula body 332. Using the illustrated examples presented in FIGS. 3 through 12, where the bone reinforcement composition is dispensed into each of the second vertebrae 112, the replacement intervertebral spacer body 202, and the first vertebrae 102, the process initiates with a first incremental withdrawal of the composition delivery cannula body 332 followed by a dispensing of a first volume of the delivered reinforcement composition 352 into the second vertebrae 112 (block 432), as illustrated in FIG. 8. The process repeats with sequentially incremental withdrawals of the composition delivery cannula body 332 followed by a dispensing of a respective volume of the delivered reinforcement composition 352 into the second vertebrae 112 (block 434), as illustrated in FIGS. 9 through 11.

Figure 12:
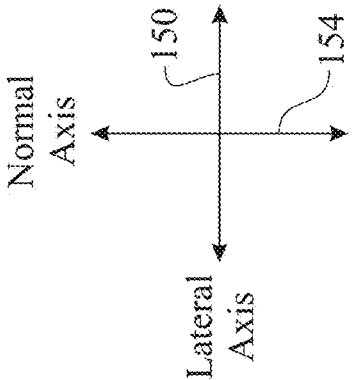
FIG. 12 presents a sectioned side elevation view illustrating a resulting bore following removal of the cannula guide instrument from the vertebra.

FIG. 12 is a sectioned side elevation view illustrating a resulting bore following removal of the cannula guide instrument from the vertebra. The cannula tubular guide instrument body 312 of the cannula guide instrument 300 can be removed from the first vertebrae 102, as illustrated in FIG. 12 (block 440 of FIG. 13). When removed, the cannula tubular guide instrument body 312 a residual bore 360 remains. The residual bore 360 can optionally be filled with a volume of the delivered reinforcement composition 352 (not illustrated) by carefully withdrawing the cannula tubular guide instrument body 312 while leaving the composition delivery cannula body 332 with the residual bore 360.

It is recognized that the insertion of the composition delivery cannula body 332 can stop where the composition delivery cannula body distal end 339 is located within the replacement intervertebral spacer body 202 or the composition delivery cannula body 332 can continue being inserted where the insertion of the composition delivery cannula body 332 can stop where the composition delivery cannula body distal end 339 is located within the second vertebrae 112. The concept of the present invention is to stabilize one or more vertebrae 100, 110 and/or intervertebral members 120, 202 relative to each other in a way that prevents the need for placement of pedicle screws. The process can be repeated at multiple locations to aid in stabilizing the elements relative to one another.

The process can be monitored using the live imaging system. The bone reinforcement material can include one or more chemical materials (e.g., radiopaque elements, chemical elements, etc.), biocompatible materials, or the like to aid in viewing the dispensed volume of the bone reinforcement material 352 using the live imaging system.

During use, the live imaging system can be toggled on and off to minimize any unwarranted exposure to the patient and medical team.

Figure 13:
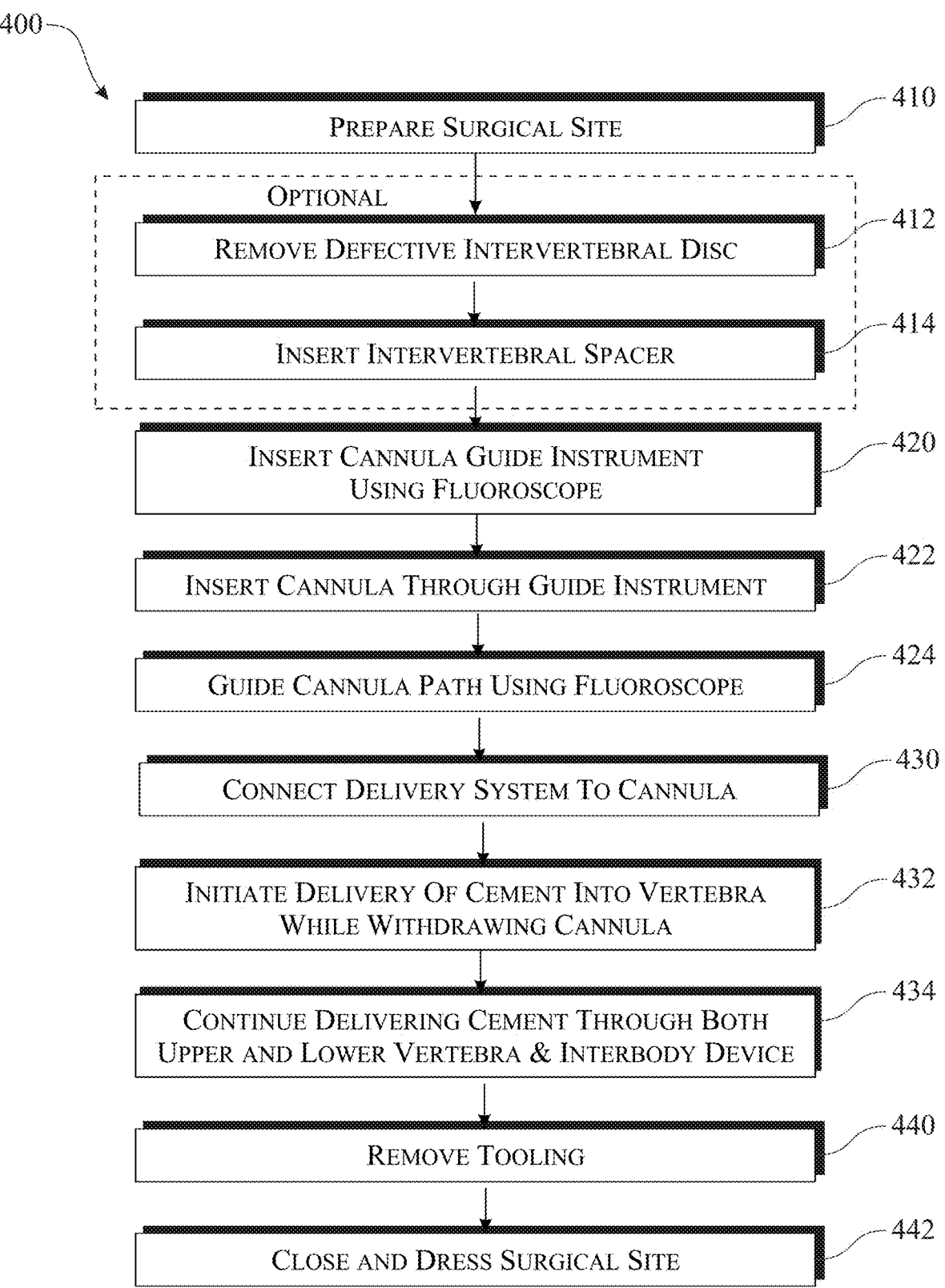
FIG. 13 presents a flow diagram outlining a process for injecting a bone reinforcing composition within adjacent vertebra and through an optionally inserted intervertebral spacer body.

Once the delivered reinforcement composition 352 has been dispensed into the surgical site and the tooling 300, 320 has been removed, the surgical site is closed and dressed (block 442 of FIG. 13).

The above describes a process for retaining an intervertebral device 200 in situ between two adjacent vertebrae 100, 110 by directing and inserting a composition delivery cannula instrument 320 into the respective adjacent vertebra 100, 110 of the two adjacent vertebrae 100, 110 and into the intervertebral device 200.

Figure 24:
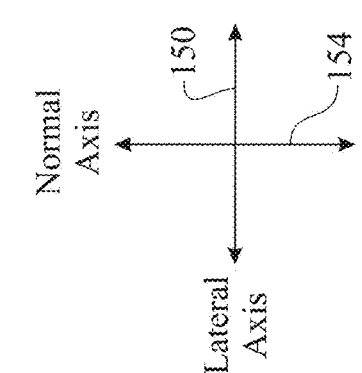
FIG. 24 presents a side sectioned elevation view of the exemplary intervertebral spacer originally introduced in FIG. 14 as installed between two adjacent vertebrae, the section being identified by section line 15-15 of FIG. 14, the illustration presenting a fourth exemplary step of rotating and continuing to remove the cannula from the off-centered guide while continuing to dispense the bone reinforcing material into and through the outer cannula guide for retaining the exemplary intervertebral spacer in situ.
Figure 25:
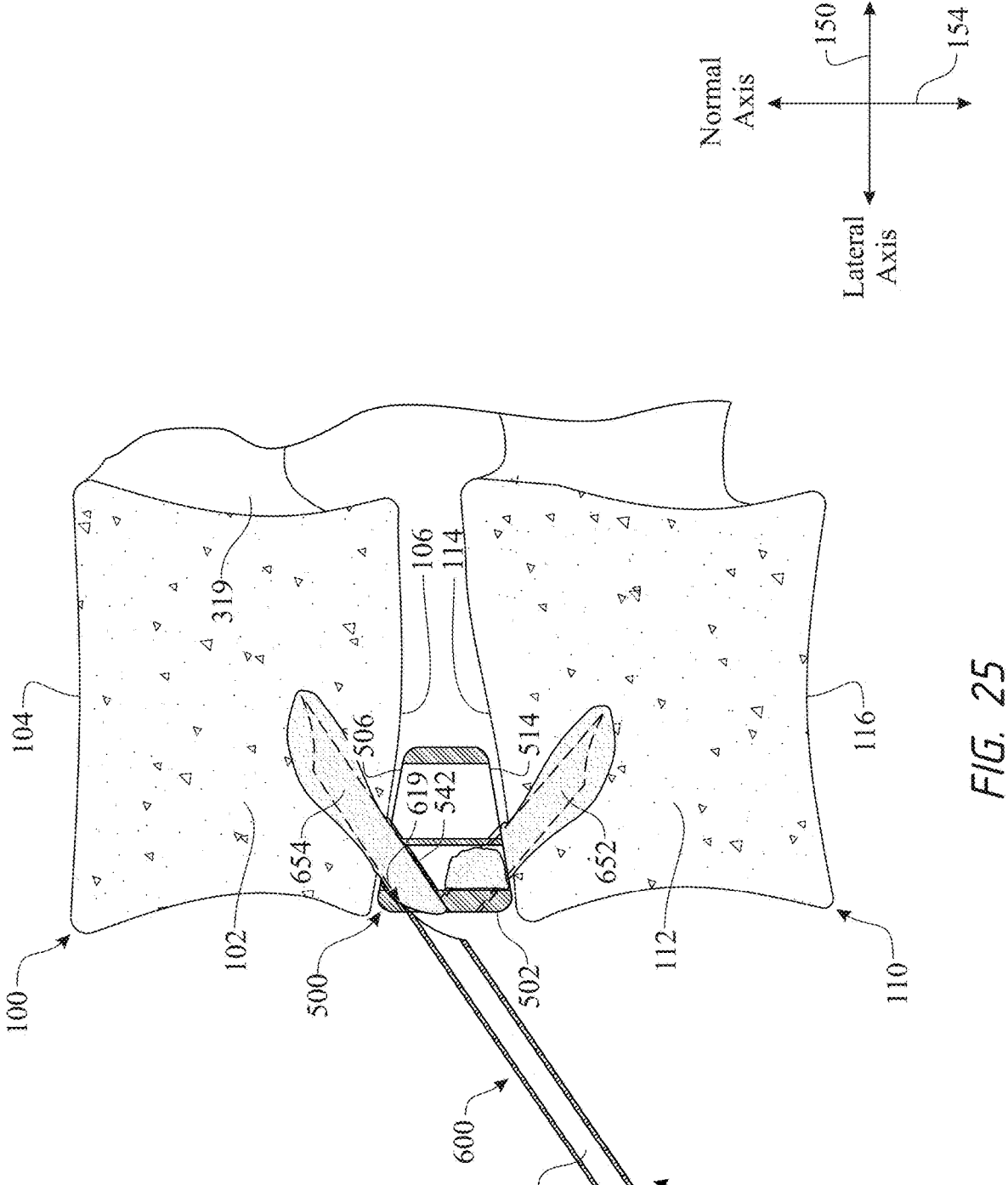
FIG. 25 presents a side sectioned elevation view of the exemplary intervertebral spacer originally introduced in FIG. 14 as installed between two adjacent vertebra, the section being identified by section line 16-16 of FIG. 14, the illustration presenting a finishing exemplary step of rotating and continuing to remove the cannula from the guide while continuing to dispense the bone reinforcing material into and through the central cannula guide for retaining the exemplary intervertebral spacer in situ.
Figure 26:
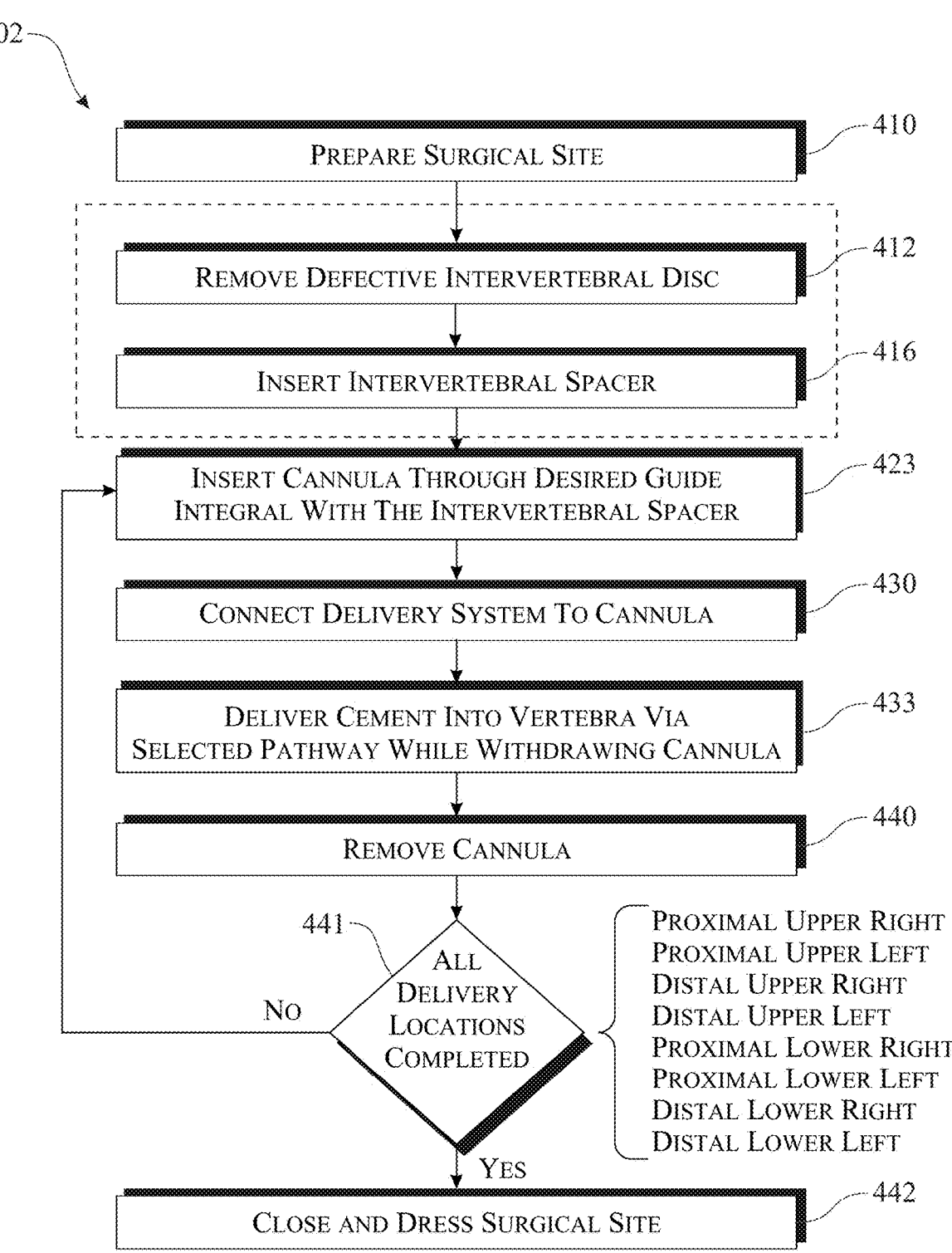
FIG. 26 presents a flow diagram outlining a second process for injecting a bone reinforcing composition through an inserted intervertebral spacer body and into at least one adjacent vertebrae.

The above-process can be reversed where a composition delivery cannula 600 can be inserted through an intervertebral spacer and into a respective adjacent vertebra 100, 110 of two adjacent vertebrae 100, 110, as illustrated in FIGS. 19 through 25 and described in connection with FIG. 26. Details of the intervertebral spacer 500 are presented in FIGS. 14 through 18.

Figure 14:
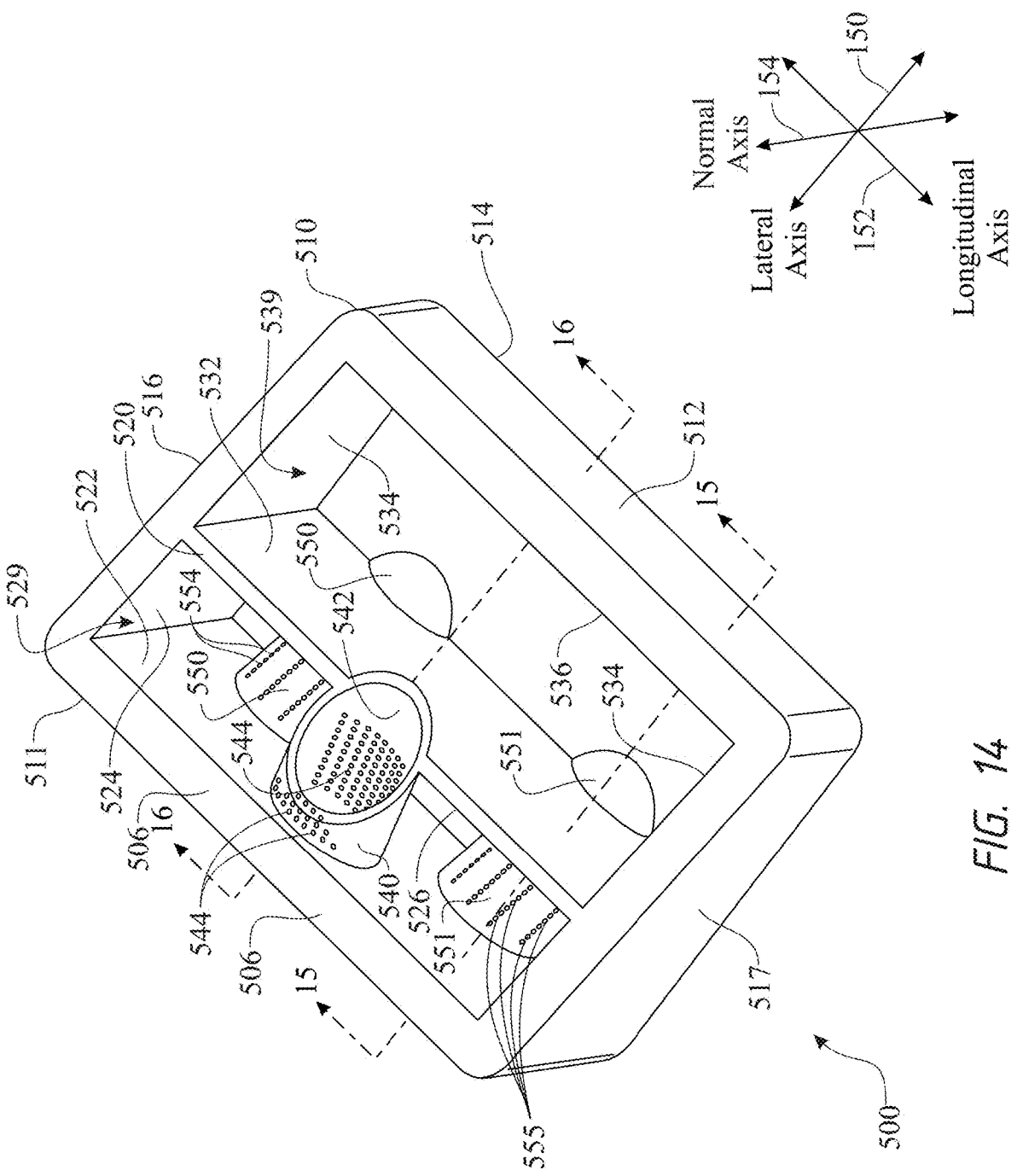
FIG. 14 presents a top side isometric view introducing an exemplary intervertebral spacer, the intervertebral spacer comprising a plurality of cement injection guides.
Figure 15:
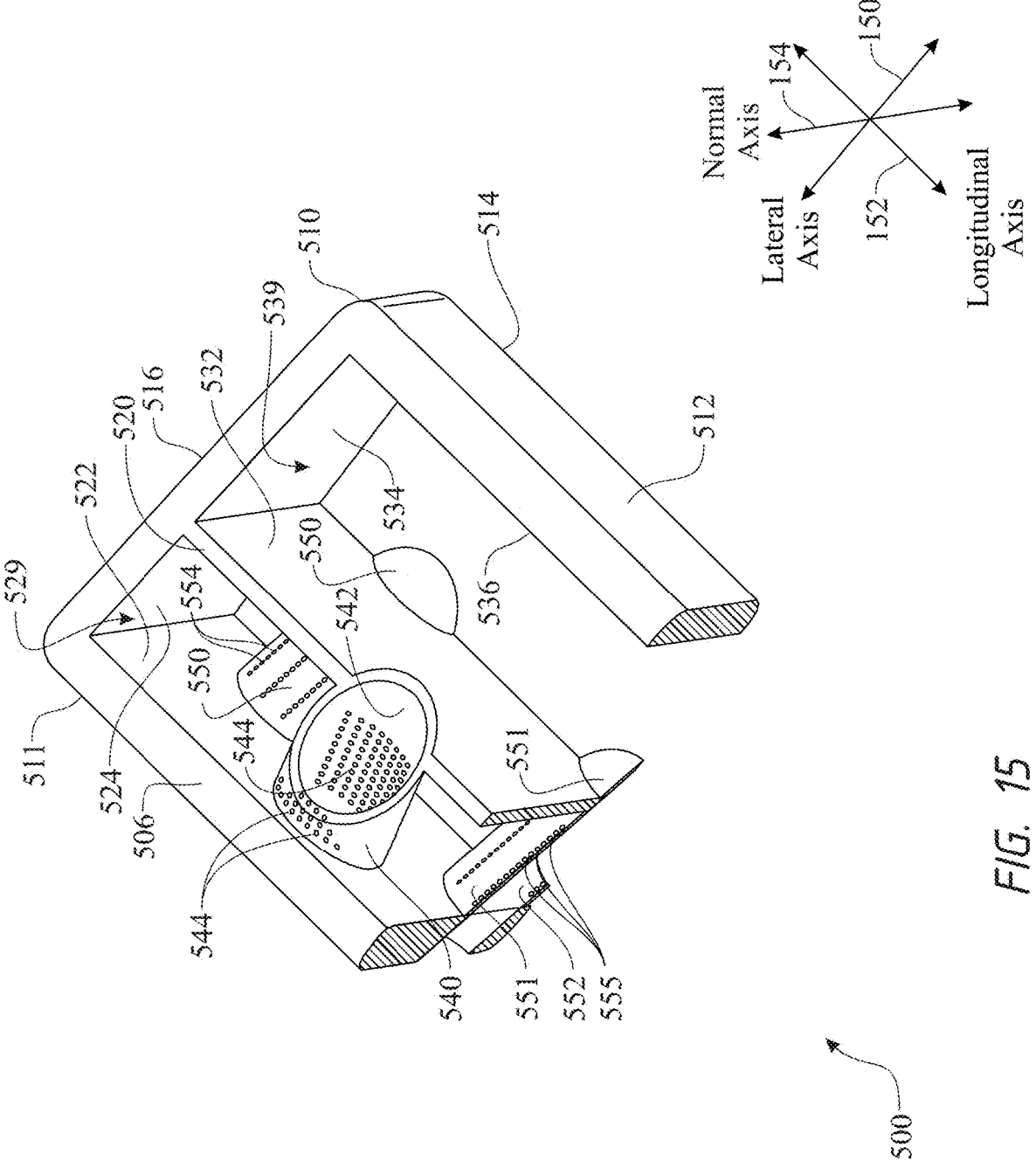
FIG. 15 presents a top side sectioned isometric view of the exemplary intervertebral spacer originally introduced in FIG. 14, the section being taken through a non-centered cement injection guide, the section being identified by section line 15-15 of FIG. 14.
Figure 16:
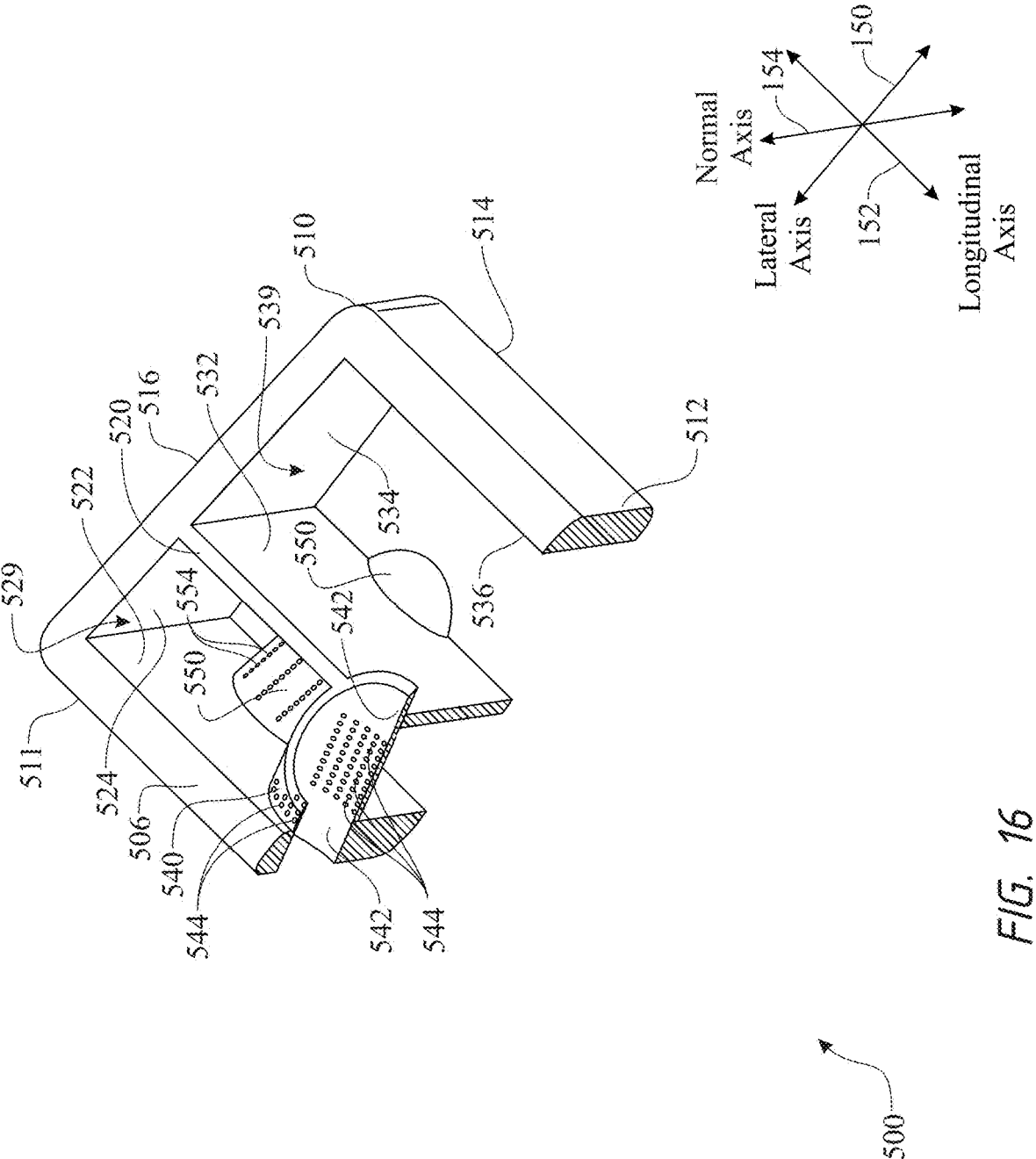
FIG. 16 presents a top side sectioned isometric view of the exemplary intervertebral spacer originally introduced in FIG. 14, the section being taken through a central cement injection guide, the section being identified by section line 16-16 of FIG. 14.

FIG. 14 is a top isometric view of an exemplary intervertebral spacer 500 including a plurality of cement injection guides. The intervertebral spacer 500 includes an intervertebral spacer body 510 comprising an intervertebral spacer body trailing (broader) panel 511, an intervertebral spacer body leading (narrow) panel 512, an intervertebral spacer body first tapering side panel 516, and an intervertebral spacer body second tapering side panel 517, as best illustrated in an isometric view presented in FIG. 14. In a plan view of the exemplary illustration (not shown but understood in the isometric view illustrated in FIG. 14), the intervertebral spacer body 510 has a rectangular shape, wherein each of the intervertebral spacer body trailing (broader) panel 511, the intervertebral spacer body leading (narrow) panel 512, the intervertebral spacer body first tapering side panel 516, and the intervertebral spacer body second tapering side panel 517 are planar in shape. The intervertebral spacer body trailing (broader) panel 511, the intervertebral spacer body leading (narrow) panel 512, the intervertebral spacer body first tapering side panel 516, and the intervertebral spacer body second tapering side panel 517 collectively defines an intervertebral spacer body upper vertebral contacting surface 506 on a first surface and an intervertebral spacer body lower vertebral contacting surface 514 on a second, opposite surface.

Figure 17:
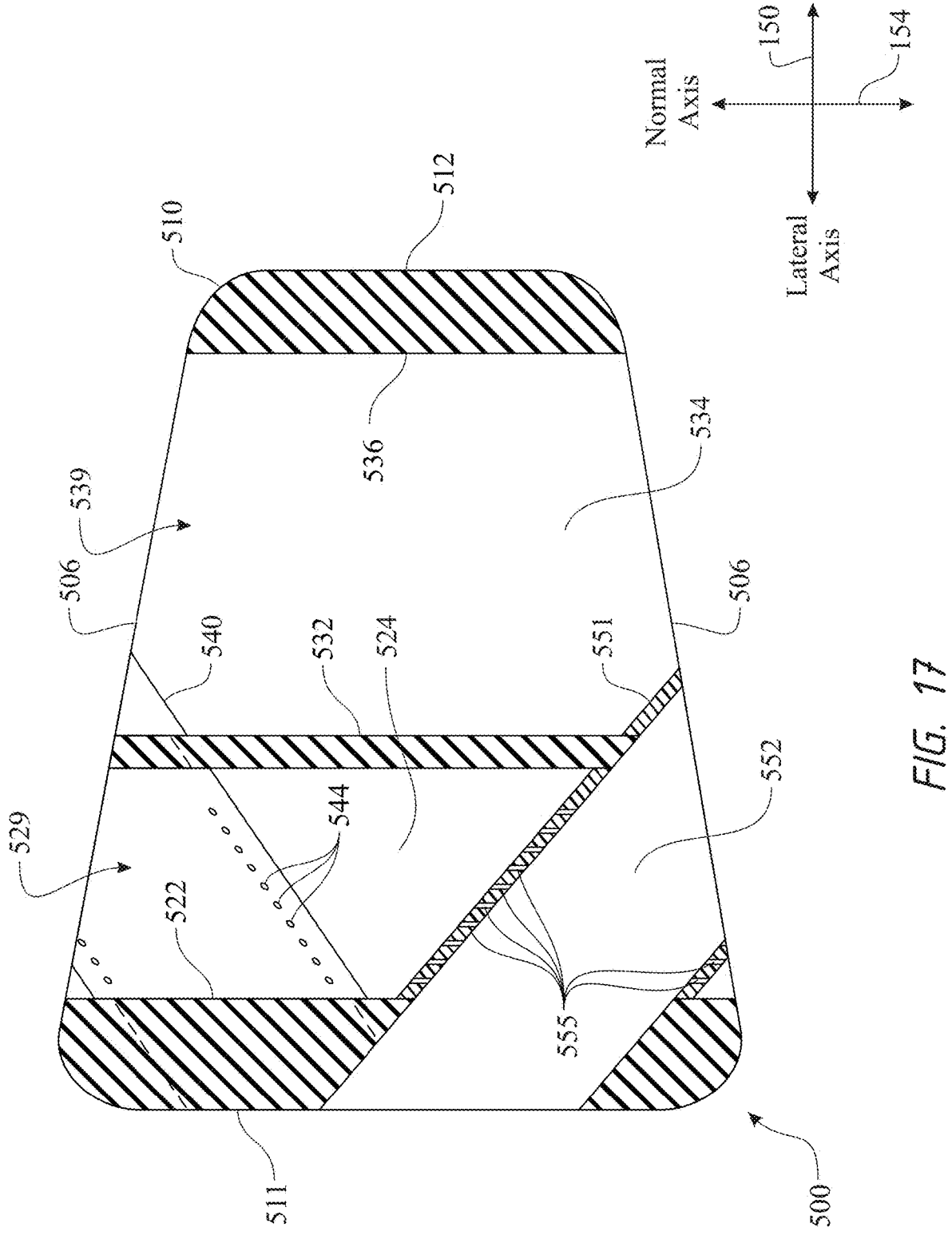
FIG. 17 presents a side sectioned elevation view of the exemplary intervertebral spacer originally introduced in FIG. 14, the section being taken through a non-centered cement injection guide, the section being identified by section line 15-15 of FIG. 14.
Figure 18:
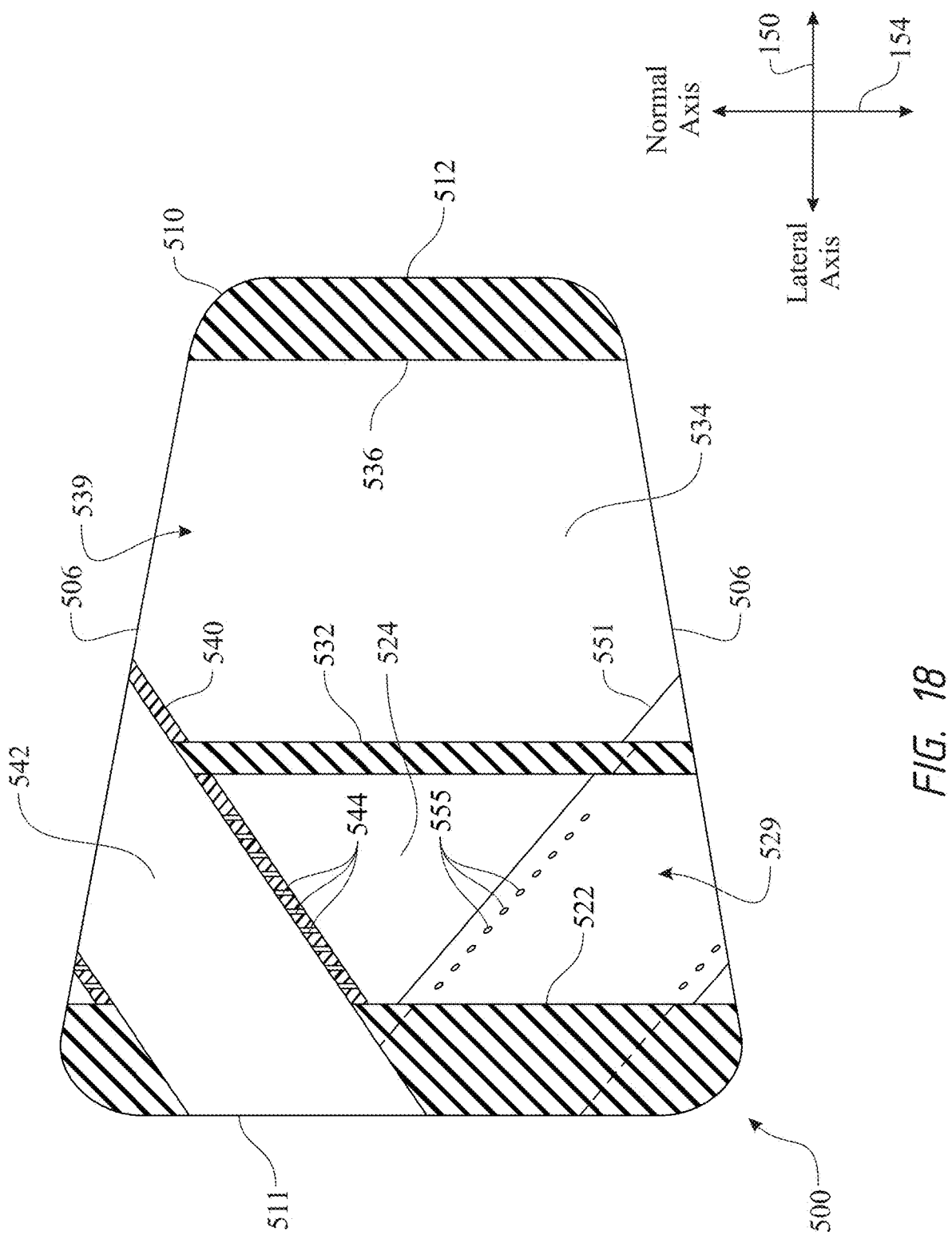
FIG. 18 presents a side sectioned elevation view of the exemplary intervertebral spacer originally introduced in FIG. 14, the section being taken through a central cement injection guide, the section being identified by section line 16-16 of FIG. 14.
Figure 19:
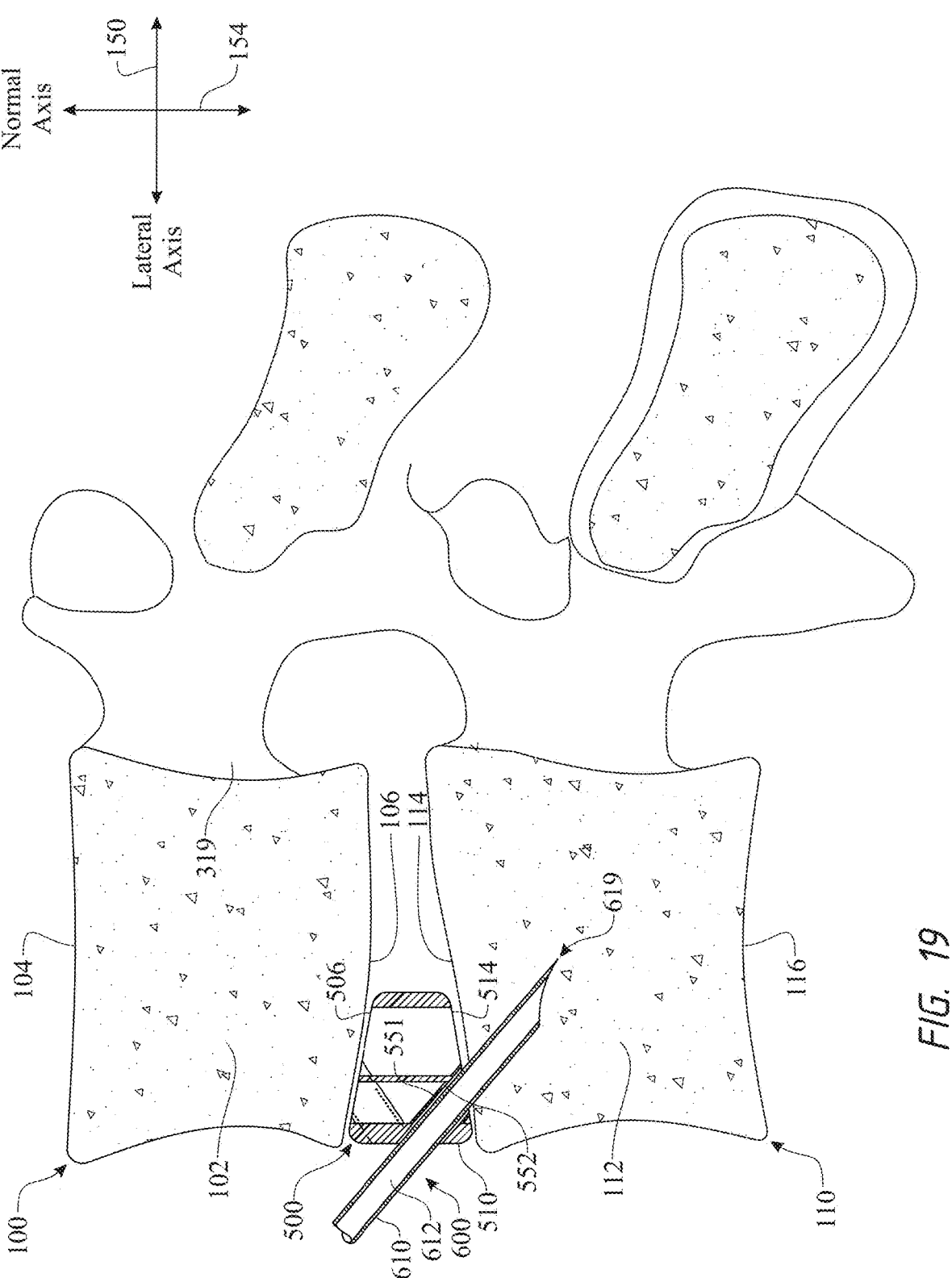
FIG. 19 presents a side sectioned elevation view of the exemplary intervertebral spacer originally introduced in FIG. 14 as installed between two adjacent vertebrae and having a cannula inserted through the non-centered cement injection guide, the section being identified by section line 15-15 of FIG. 14.
Figure 20:
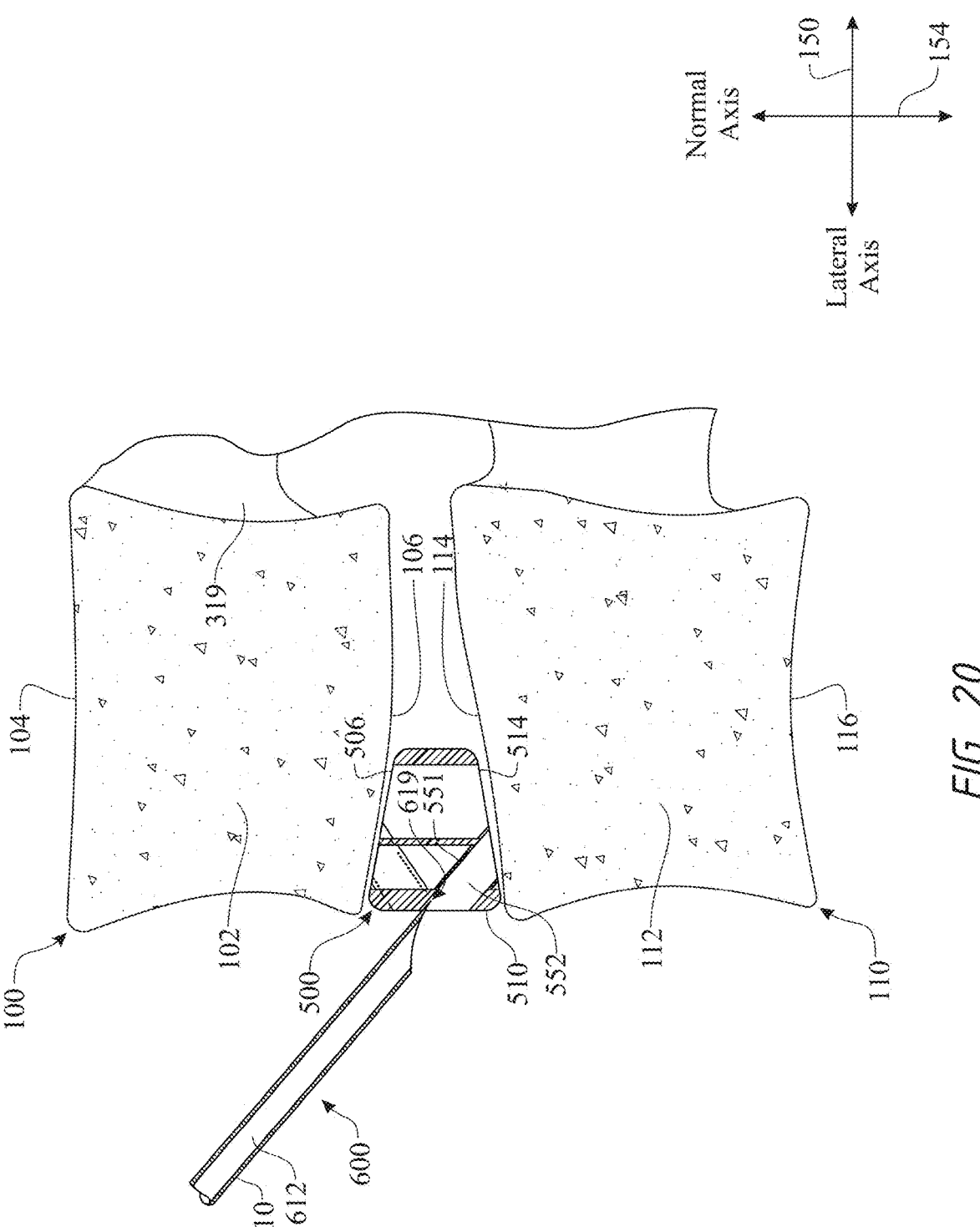
FIG. 20 presents a side sectioned elevation view of the exemplary intervertebral spacer originally introduced in FIG. 14 as installed between two adjacent vertebrae, the section being identified by section line 15-15 of FIG. 14 and prepared to dispense bone reinforcing material into a respective vertebra for retaining the exemplary intervertebral spacer in situ.

FIG. 17 is a side cross-sectional view of the exemplary intervertebral spacer discussed in connection with FIG. 14, with the section being taken through a non-centered cement injection guide along section line 15-15 of FIG. 14. FIG. 18 is a side cross-sectional view of the exemplary intervertebral spacer taken along a section line 16-16 of FIG. 14. Referring to FIGS. 17 and 18, the intervertebral spacer body side panels 516, 517 of the exemplary intervertebral spacer 500 are tapered. Each intervertebral spacer body side panel 516, 517 extends from a respective edge of a taller intervertebral spacer body trailing (broader) panel 511 to a like-sided respective edge of a shorter intervertebral spacer body leading (narrow) panel 512. Although the illustrations present a configuration of the intervertebral spacer 500 where each panel 511, 512, 516, 517 of the intervertebral spacer 500 has a linear shape, it is understood that one or more of the intervertebral spacer body trailing (broader) panel 511, the intervertebral spacer body leading (narrow) panel 512, the intervertebral spacer body first tapering side panel 516, and the intervertebral spacer body second tapering side panel 517 can be curved in shape.

The exemplary intervertebral spacer 500 includes an intervertebral spacer body central transversing panel 520 extending between the intervertebral spacer body first tapering side panel 516 and the intervertebral spacer body second tapering side panel 517. The exemplary intervertebral spacer body central transversing panel 520 is illustrated being parallel to the intervertebral spacer body trailing (broader) panel 511 and the intervertebral spacer body leading (narrow) panel 512. It is understood that the intervertebral spacer body central transversing panel 520 can be integrated at any angle and/or shape with considerations for functionality and reliability of the desired intervertebral spacer 500. The intervertebral spacer 500 can include one or more intervertebral spacer body central transversing panels 520.

The intervertebral spacer body trailing (broader) panel 511, the intervertebral spacer body central transversing panel 520, a first portion of the intervertebral spacer body first tapering side panel 516, and a first portion of the intervertebral spacer body second tapering side panel 517, collectively define an intervertebral spacer body first chamber 529. More specifically, an intervertebral spacer body trailing (broader) panel interior surface 522 of the intervertebral spacer body trailing (broader) panel 511, an intervertebral spacer body tapering side panel first chamber interior surface 524 of each of the intervertebral spacer body first tapering side panel 516 and intervertebral spacer body second tapering side panel 517, and an intervertebral spacer body central transversing panel first chamber interior surface 526 of the intervertebral spacer body central transversing panel 520 define the intervertebral spacer body first chamber 529. Similarly, the intervertebral spacer body central transversing panel 520, the intervertebral spacer body leading (narrow) panel 512, a second portion of the intervertebral spacer body first tapering side panel 516, and a second portion of the intervertebral spacer body second tapering side panel 517, collectively define an intervertebral spacer body second chamber 539. More specifically, an intervertebral spacer body central transversing panel second chamber interior surface 532 of the intervertebral spacer body central transversing panel 520, an intervertebral spacer body tapering side panel second chamber interior surface 534 of each of the intervertebral spacer body first tapering side panel 516 and intervertebral spacer body second tapering side panel 517, and an intervertebral spacer body leading (narrow) panel 536 of the intervertebral spacer body leading (narrow) panel 512 define the intervertebral spacer body second chamber 539. One or both of the intervertebral spacer body first chamber 529 and the intervertebral spacer body second chamber 539 can be used to receive bone graft material to enhance a fusion process between the two adjacent vertebrae 100, 110.

A proximal end of an intervertebral spacer central cement injection guide 540 is supported by the intervertebral spacer body trailing (broader) panel 511 and a distal end of the intervertebral spacer central cement injection guide 540 is supported by a first end of the intervertebral spacer body central transversing panel 520. The intervertebral spacer central cement injection guide 540 provides the same function as the cannula guide instrument 300 described above. The intervertebral spacer central cement injection guide 540 is tubular in shape having a cannula directing passageway defined by an intervertebral spacer central cement injection guide interior surface 542 (identified in FIG. 18). The intervertebral spacer central cement injection guide 540 is directed between an inserting end passing through the intervertebral spacer body trailing (broader) panel 511 and a discharging end oriented towards one of the two adjacent vertebrae 100, 110.

Similarly, a proximal end of an intervertebral spacer first outer cement injection guide 550 is supported by the intervertebral spacer body trailing (broader) panel 511 and a distal end of the intervertebral spacer central cement injection guide 540 is supported by a second, opposite end of the intervertebral spacer body central transversing panel 520. The intervertebral spacer first outer cement injection guide 550 is tubular in shape having a cannula directing passageway defined by an intervertebral spacer second outer cement injection guide interior surface 552 (identified in FIG. 17). The intervertebral spacer first outer cement injection guide 550 is directed between an inserting end passing through the intervertebral spacer body trailing (broader) panel 511 and a discharging end oriented towards the other of the two adjacent vertebrae 100, 110.

A combination of the intervertebral spacer central cement injection guide 540 and the intervertebral spacer first outer cement injection guide 550 provides stability to the intervertebral spacer 500 by each of the two adjacent vertebrae 100, 110. Additional cement injection guides, such as an intervertebral spacer second outer cement injection guide 551 can be included to enable the surgeon to provide more stability to the intervertebral spacer 500 when inserted between the two adjacent vertebrae 100, 110 using additional streams of the dispensed bone reinforcement composition (as will be described later herein). An intervertebral spacer second outer cement injection guide interior surface 552 of the intervertebral spacer second outer cement injection guide 551 defines the cannula directing passageway.

The affectivity of the bone reinforcement composition can be enhanced by introducing a plurality of pores 544, 554, 555 through each of the cement injection guides 540, 550, 551 respectively. The pores 544, 554, 555 would be of a diameter suitable for passage of the bone reinforcement composition.

Although the exemplary illustrations presenting the intervertebral spacer 500 define a specific configuration, it is understood that the intervertebral spacer 500 can be modified in any of a variety of manners. As described above, one or more of the intervertebral spacer body trailing (broader) panel 511, intervertebral spacer body leading (narrow) panel 512, intervertebral spacer body first tapering side panel 516, and intervertebral spacer body second tapering side panel 517 can be curved in shape. The intervertebral spacer 500 can include a top panel and/or a bottom panel (not shown). The top panel and/or a bottom panel can cover a portion or all of the respective edges 506, 514. The top panel and/or a bottom panel can be planar in shape, domed in shape, or of any other suitable shape. The top panel and/or a bottom panel can be perforated with pores similar to the pores 544, 554, 555 of the cement injection guides 540, 550, 551.

The cement injection guides 540, 550, 551 are illustrated having a circular cross sectioned shape enabling rotation of the cannula. Advantages of this will be described herein. Alternatively, in certain instances, there may be benefits in a design where the cement injection guides 540, 550, 551 have a non-circular cross sectioned shape to retain the cannula in a specific orientation.

Additionally, the cement injection guides 540, 550, 551 are illustrated having a linear shape in a longitudinal direction. The linear configuration enables application of more force during the process of inserting the cannula into the respective vertebra 100, 110 while lowering a risk of displacing the intervertebral spacer 500. The cement injection guides 540, 550, 551 may be curved in the longitudinal direction enabling horizontal insertion into an entrance end of the passageway 542, 552 and a more vertical discharge at an exit end of the passageway 542, 552. The curved configuration may simplify the process for the surgeon. The cannula can be rigid or flexible, straight or at least partially curved.

FIGS. 19 through 25 illustrated the bone reinforcing composition delivery system flow diagram 402. FIG. 26 shows a bone reinforcing composition delivery system flow diagram 402 configured to dispense a volume of staged reinforcement composition 650 into a path created by a composition delivery cannula body 610. The bone reinforcing composition delivery system flow diagram 402 is similar to the bone reinforcing composition delivery system flow diagram 400 with like steps being numbered the same. The intervertebral spacer 500 is inserted between the two adjacent vertebrae 100, 110 (block 416). The intervertebral spacer 500 is oriented with the intervertebral spacer body leading (narrow) panel 512 leading the insertion direction. This enables access to the entrances of the intervertebral spacer central cement injection guide interior surface 542, intervertebral spacer second outer cement injection guide interior surface 552 through the intervertebral spacer body trailing (broader) panel 511 of the intervertebral spacer 500 via the same incision site as used for insertion of the intervertebral spacer 500 between two adjacent vertebrae 100, 110 (block 416). A composition delivery cannula 600 is inserted through a first selected one of the cement injection guides 540, 550, 551 (block 423). In the exemplary illustration presented in FIG. 20, the composition delivery cannula 600 is inserted through the intervertebral spacer second outer cement injection guide interior surface 552 of the intervertebral spacer second outer cement injection guide 551. A composition delivery cannula body insertion end 619 of the composition delivery cannula 600 can include a point (as illustrated) or a sharpened perpendicular edge (similar to the design of a hole punch). The composition delivery cannula 600 is inserted into a desired depth, as illustrated in FIG. 21. The depth can be determined by the medical staff. The depth can be identified using any imaging system, a marking on the composition delivery cannula body 610, or any other suitable method.

Figure 22:
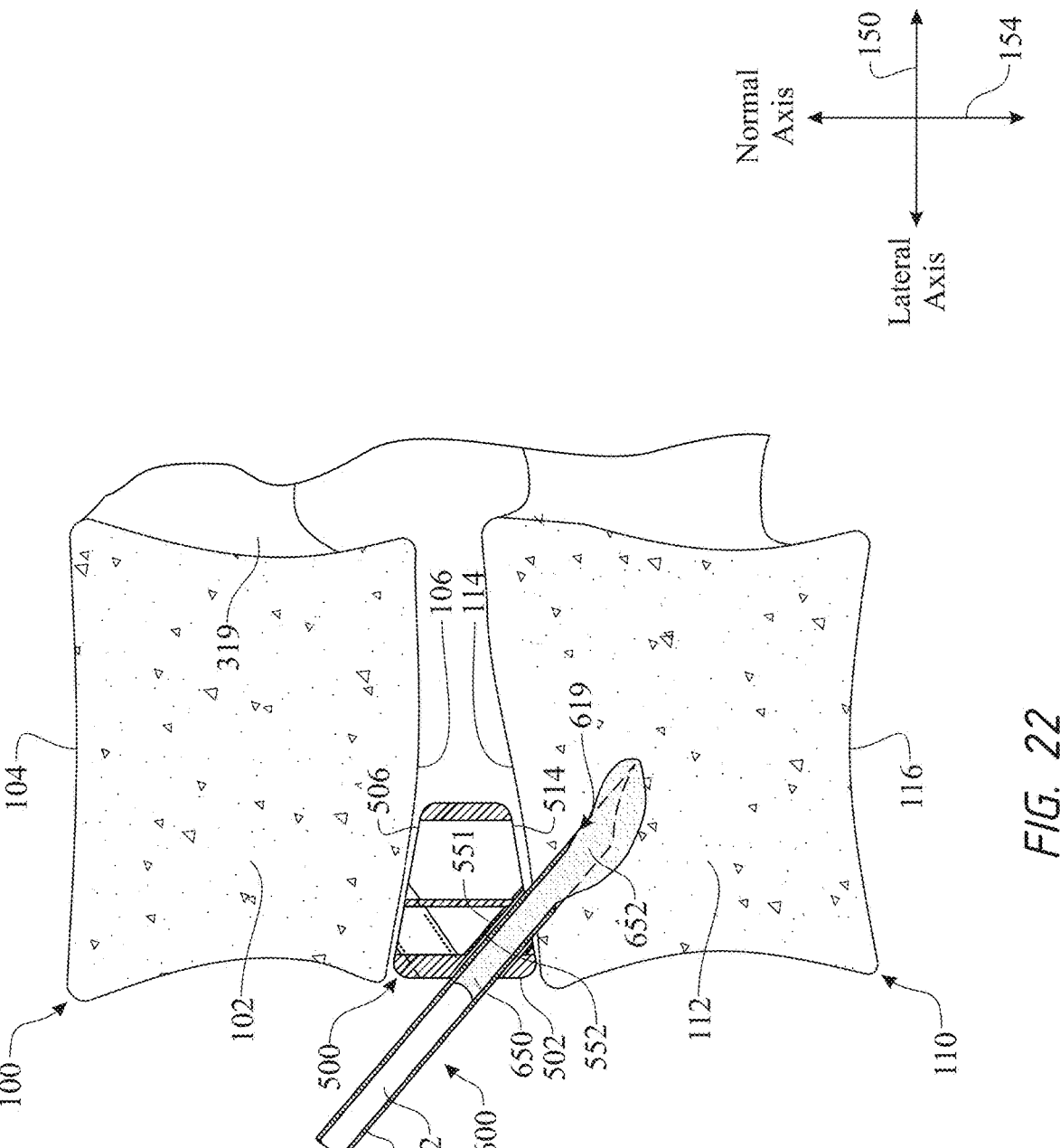
FIG. 22 presents a side sectioned elevation view of the exemplary intervertebral spacer originally introduced in FIG. 14 as installed between two adjacent vertebrae, the section being identified by section line 15-15 of FIG. 14, the illustration presenting a second exemplary step of slowly removing the cannula from the created bore and dispensing bone reinforcing material into the respective vertebra for retaining the exemplary intervertebral spacer in situ.
Figure 23:
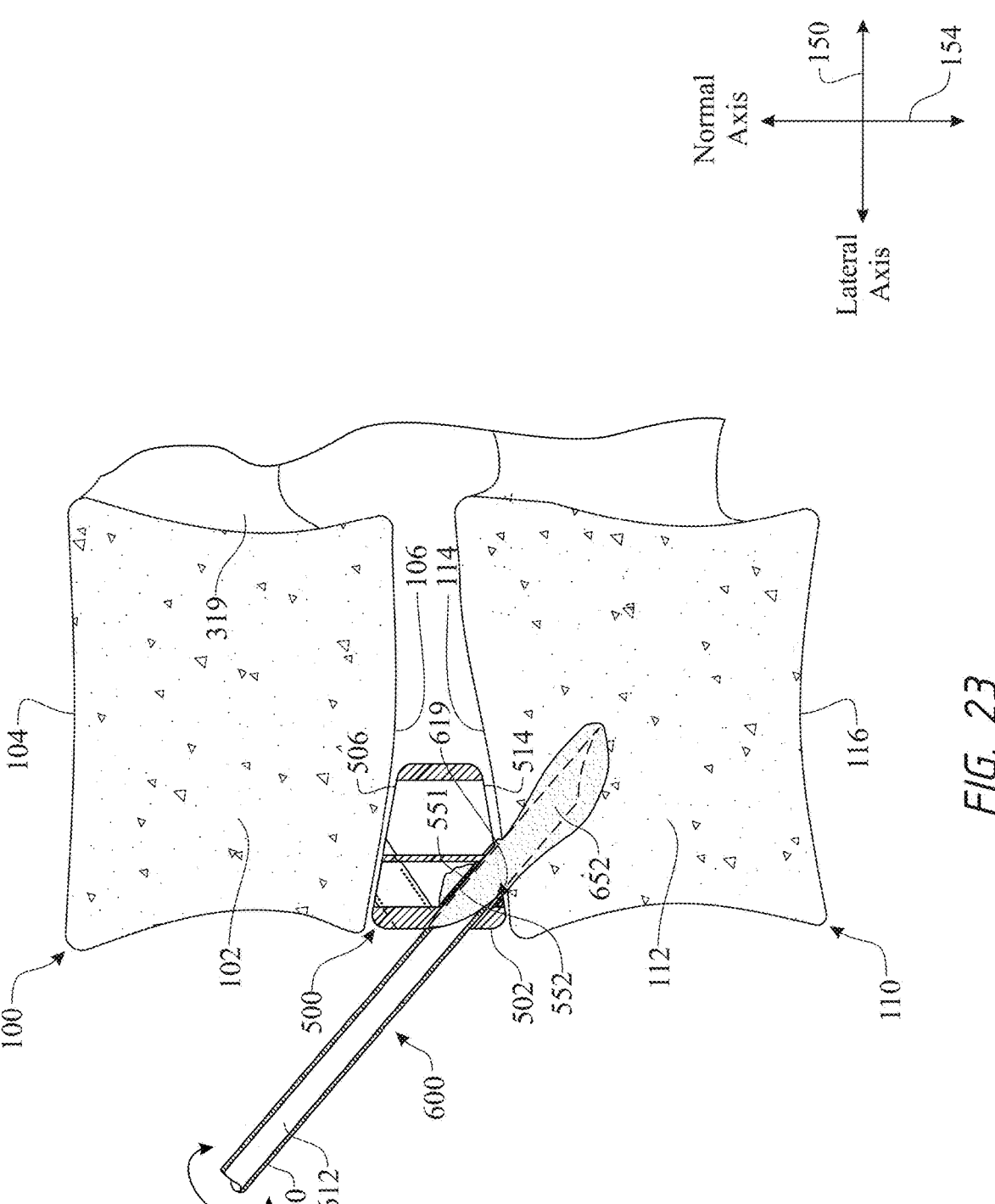
FIG. 23 presents a side sectioned elevation view of the exemplary intervertebral spacer originally introduced in FIG. 14 as installed between two adjacent vertebra, the section being identified by section line 15-15 of FIG. 14, the illustration presenting a third exemplary step of continuing to remove the cannula from the created bore and the off-centered guide while continuing to dispense the bone reinforcing material into the respective vertebra and into the outer cannula guide for retaining the exemplary intervertebral spacer in situ.

A bone reinforcement delivery system (reference numeral 350 associated with the cannula guide instrument 300) is connected to the composition delivery cannula body 610 either prior to or subsequent to positioning of the composition delivery cannula body insertion end 619 (block 430). The bone reinforcement delivery system dispenses the staged reinforcement composition 650 through a composition delivery cannula body interior passageway 612 of a composition delivery cannula body 610 of the composition delivery cannula 600 (block 433). A volume of the staged reinforcement composition 650 is dispensed as the staged reinforcement composition 650 is withdrawn from the respective adjacent vertebra 100, 110 leaving an outer located delivered reinforcement composition 652 initially within the respective adjacent vertebra 100, 110 then additional portions of the outer located delivered reinforcement composition 652 within the intervertebral spacer second outer cement injection guide interior surface 552 of the intervertebral spacer 500 (block 433), as illustrated in FIGS. 22 through 24. The process of withdrawing the composition delivery cannula 600 and dispensing the staged reinforcement composition 650 (block 433) can be accomplished with any suitable steps. In one example, the composition delivery cannula 600 can be withdrawn a short distance, then the staged reinforcement composition 650 would be dispensed to fill the region that is cleared by the withdrawal of the composition delivery cannula 600. The process is repeated until the desired volume of staged reinforcement composition 650 is dispensed and the composition delivery cannula 600 is completely withdrawn from the intervertebral spacer second outer cement injection guide interior surface 552 (block 440). In a second example, the staged reinforcement composition 650 can be dispensed simultaneously while the composition delivery cannula 600 is being withdrawn until the desired volume of staged reinforcement composition 650 is dispensed and the composition delivery cannula 600 is fully removed from the patient (block 440).

The intervertebral spacer 500 can include one or more cement injection guides 540, 550, 551. The bone reinforcing composition delivery system flow diagram 402 includes a decision step to determine if all delivery locations are processed (decision step 441). The exemplary intervertebral spacer 500 includes a central upward directing path 540, a first off-center downward directing path 550, and a second off-center downward directing path 551. The process repeats steps 423 through 441 until all of the selected pathways have been used to dispense the staged reinforcement composition 650 to adequately retain the intervertebral spacer 500 in position between the adjacent vertebra 100, 110.

The exemplary intervertebral spacer 500 includes three (3) cannula guides or pathways 540, 550, 551. A second exemplary cycle of steps 423 through 440 are illustrated in FIG. 25, where the composition delivery cannula 600 is inserted through intervertebral spacer central cement injection guide interior surface 542 of the intervertebral spacer central cement injection guide 540 and dispenses a volume of the reinforcement composition 650 forming a centrally located delivered reinforcement composition 654 into the first joint member 100 and the central cement injection guide interior surface 542.

Once all of the selected pathways have been used to dispense the staged reinforcement composition 650 to adequately retain the intervertebral spacer 500 in position between the adjacent vertebra 100, 110 and the composition delivery cannula 600 is removed from the patient one final time, the surgical team closes and dresses the surgical site (block 442).

The intervertebral spacer 500 is one exemplary design of an intervertebral spacer including at least one cement injection guide. The exemplary cement injection guides 540, 550, 551 are tubular extending between the entrance to the exit. Each exemplary cement injection guide 540, 550, 551 provides a distinct path for the composition delivery cannula 600.

Figure 27:
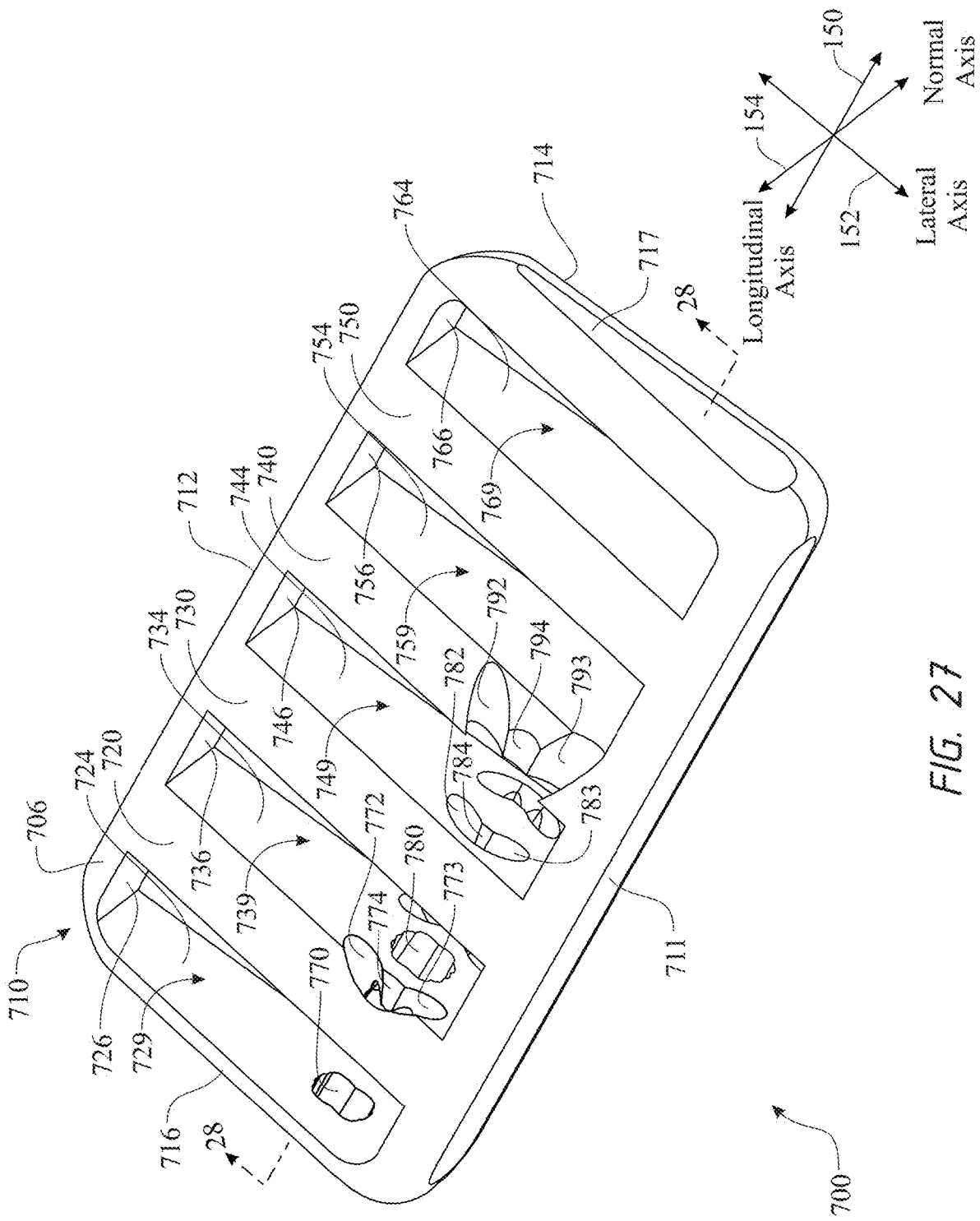
FIG. 27 presents a top side isometric view introducing a second exemplary intervertebral spacer, the intervertebral spacer comprising a plurality of cement injection guides for dispensing a bone reinforcing composition into at least one of two adjacent vertebrae in a disbursed manner.
Figure 28:
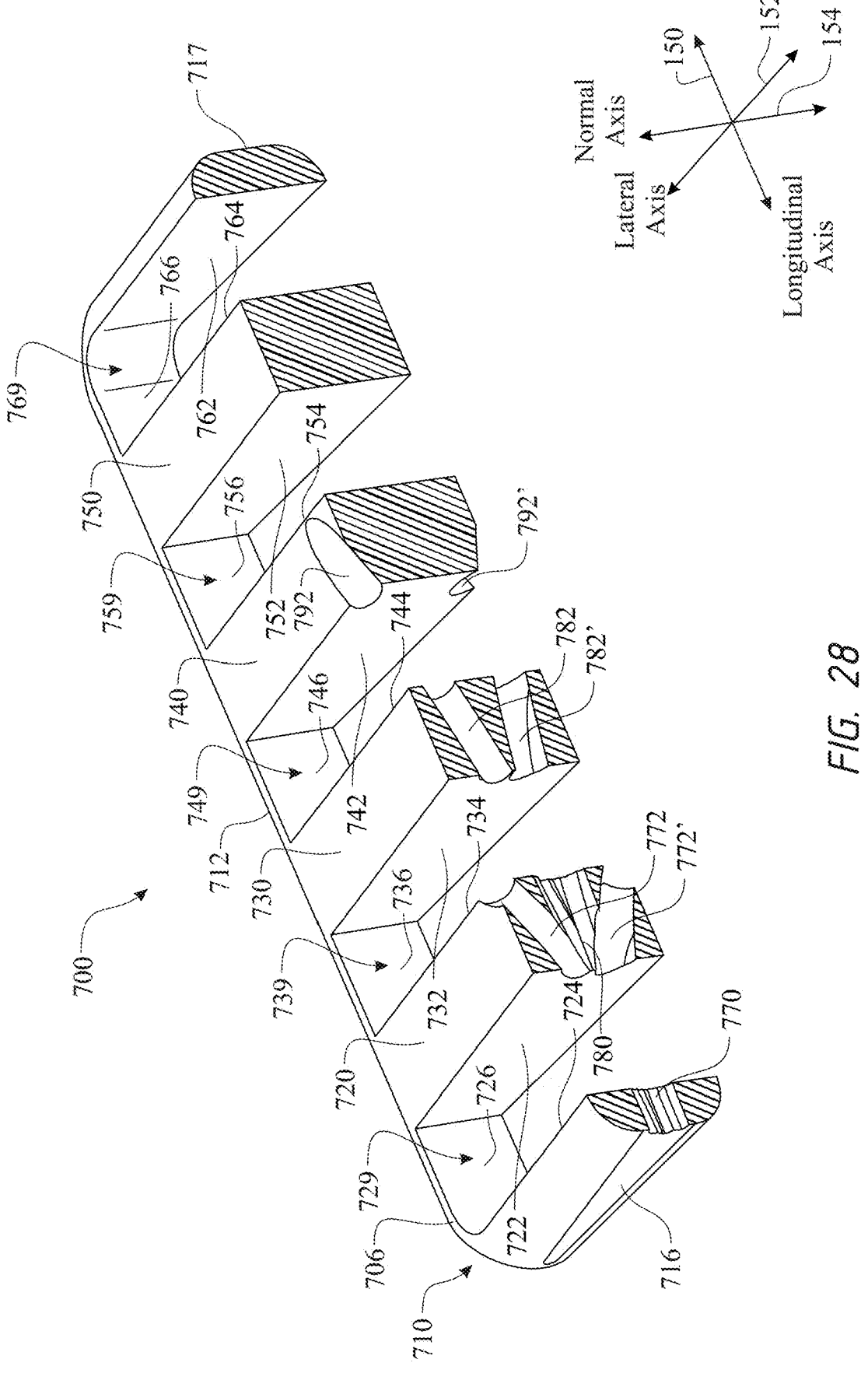
FIG. 28 presents a top side sectioned isometric view of the exemplary intervertebral spacer originally introduced in FIG. 27, the section being taken slightly offset of center of the series of cement injection guides, the section being identified by section line 28-28 of FIG. 27.

FIGS. 27 and 28 show an intervertebral spacer 700 having one initial orifice can be used to guide the cannula to several different passageways for dispensing of the bone reinforcement material in multiple locations. The intervertebral spacer 700 includes a spacer body 710 having an upper vertebral contacting surface 706 and a lower vertebral contacting surface 714.

The intervertebral spacer 700 includes an intervertebral device body trailing (broader) panel 711 extending transversely at a first, proximal end, an intervertebral device body leading (narrow) panel 712 extending transversely at a second, opposite, insertion end, an intervertebral device body first tapering side panel 716 and an intervertebral device body second tapering side panel 717. Each of the intervertebral device body first tapering side panel 716 and the intervertebral device body second tapering side panel 717 tapers from a taller intervertebral device body trailing (broader) panel 711 to a shorter intervertebral device body leading (narrow) panel 712. The intervertebral spacer 700 includes a plurality of transversing panels 720, 730, 740, 750 extending between facing surfaces of the intervertebral device body trailing (broader) panel 711 and the intervertebral device body leading (narrow) panel 712. The exemplary illustrated transversing panels 720, 730, 740, 750 are parallel to the intervertebral device body first tapering side panel 716 and the intervertebral device body second tapering side panel 717. The transversing panels 720, 730, 740, 750 may be integrated in any design and/or orientation. In one example, the transversing panels 720, 730, 740, 750 may be oriented at one or more angle respective to the intervertebral device body first tapering side panel 716 and the intervertebral device body second tapering side panel 717. In a second example, the transversing panels 720, 730, 740, 750 may be arched as opposed to being linear, as illustrated. In a third example, the transversing panels 720, 730, 740, 750 may be arranged forming a matrix forming "x" shapes, a honeycomb, or any other matrix configuration.

Each transversing panel 720, 730, 740, 750 segments the intervertebral spacer 700 creating multiple chambers 729, 739, 749, 759, 769. The intervertebral device body first chamber 729 is bound by an intervertebral device body first tapering side panel first chamber interior surface 724 of the intervertebral device body first tapering side panel 716, an intervertebral device body leading (narrow) panel first chamber interior surface 726 of a portion of the intervertebral device body leading (narrow) panel 712, a facing or opposing intervertebral device body leading (narrow) panel first chamber interior surface 726 of a portion of the intervertebral device body trailing (broader) panel 711, and an intervertebral device body first intermediary transversing panel first chamber interior surface 722 of the intervertebral device body first intermediary transversing panel 720. The intervertebral device body second chamber 739 is bound by an intervertebral device body first intermediary transversing panel second chamber interior surface 734 of the intervertebral device body first intermediary transversing panel 720, an intervertebral device body leading (narrow) panel second chamber interior surface 736 of a portion of the intervertebral device body leading (narrow) panel 712, a facing or opposing intervertebral device body leading (narrow) panel second chamber interior surface 736 of a portion of the intervertebral device body trailing (broader) panel 711, and an intervertebral device body second intermediary transversing panel second chamber interior surface 732 of the intervertebral device body second intermediary transversing panel 730. The intervertebral device body fourth chamber 749 is bound by an intervertebral device body second intermediary transversing panel third chamber interior surface 744 of the intervertebral device body second intermediary transversing panel 730, an intervertebral device body leading (narrow) panel fourth chamber interior surface 746 of a portion of the intervertebral device body leading (narrow) panel 712, a facing or opposing intervertebral device body leading (narrow) panel fourth chamber interior surface 746 of a portion of the intervertebral device body trailing (broader) panel 711, and an intervertebral device body third intermediary transversing panel third chamber interior surface 742 of the intervertebral device body third intermediary transversing panel 740. The intervertebral device body first chamber 759 is bound by an intervertebral device body third intermediary transversing panel fourth chamber interior surface 754 of the intervertebral device body third intermediary transversing panel 740, an intervertebral device body leading (narrow) panel first chamber interior surface 756 of a portion of the intervertebral device body leading (narrow) panel 712, a facing or opposing intervertebral device body leading (narrow) panel first chamber interior surface 756 of a portion of the intervertebral device body trailing (broader) panel 711, and an intervertebral device body fourth intermediary transversing panel fourth chamber interior surface 752 of the intervertebral device body fourth intermediary transversing panel 750. The intervertebral device body fifth chamber 769 is bound by an intervertebral device body fourth intermediary transversing panel fifth chamber interior surface 764 of the intervertebral device body fourth intermediary transversing panel 750, an intervertebral device body leading (narrow) panel fifth chamber interior surface 766 of a portion of the intervertebral device body leading (narrow) panel 712, a facing or opposing intervertebral device body leading (narrow) panel fifth chamber interior surface 766 of a portion of the intervertebral device body trailing (broader) panel 711, and an intervertebral device body second tapering side panel fifth chamber interior surface 762 of the intervertebral device body second tapering side panel 717. The exemplary intervertebral spacer 700 includes five (5) chambers 729, 739, 749, 759, 769. It is understood that the intervertebral spacer 700 can include any suitable number of transversing panels 720, 730, 740, 750 segmenting the intervertebral spacer 700 into any suitable number of chambers 729, 739, 749, 759, 769 for the desired number of cannula passageways and adequate support for the implant application.

As illustrated, the intervertebral spacer 700 includes twelve (12) exemplary distinct optional cannula pathways, each initiating through a short and long cannula guiding passageway entrance 770 passing through the intervertebral device body first tapering side panel 716:

(a) an upper inwardly directed proximal passageway 770, 772;

(b) an upper centrally directed proximal passageway 770, 774;

(c) an upper outwardly directed proximal passageway 770, 773;

(d) an upper inwardly directed distal passageway 770, 772, 782, 792;

(e) an upper centrally directed distal passageway 770, 774, 784, 794;

(f) an upper outwardly directed distal passageway 770, 773, 783, 793;

(g) a lower inwardly directed proximal passageway 770, 772';

(h) a lower centrally directed proximal passageway 770, 774';

(i) a lower outwardly directed proximal passageway 770, 773';

(j) a lower inwardly directed distal passageway 770, 772', 782', 792';

(k) a lower centrally directed distal passageway 770, 774', 784', 794'; and (l) a lower outwardly directed distal passageway 770, 773', 783', 793'.

Figures 29A, 29B:
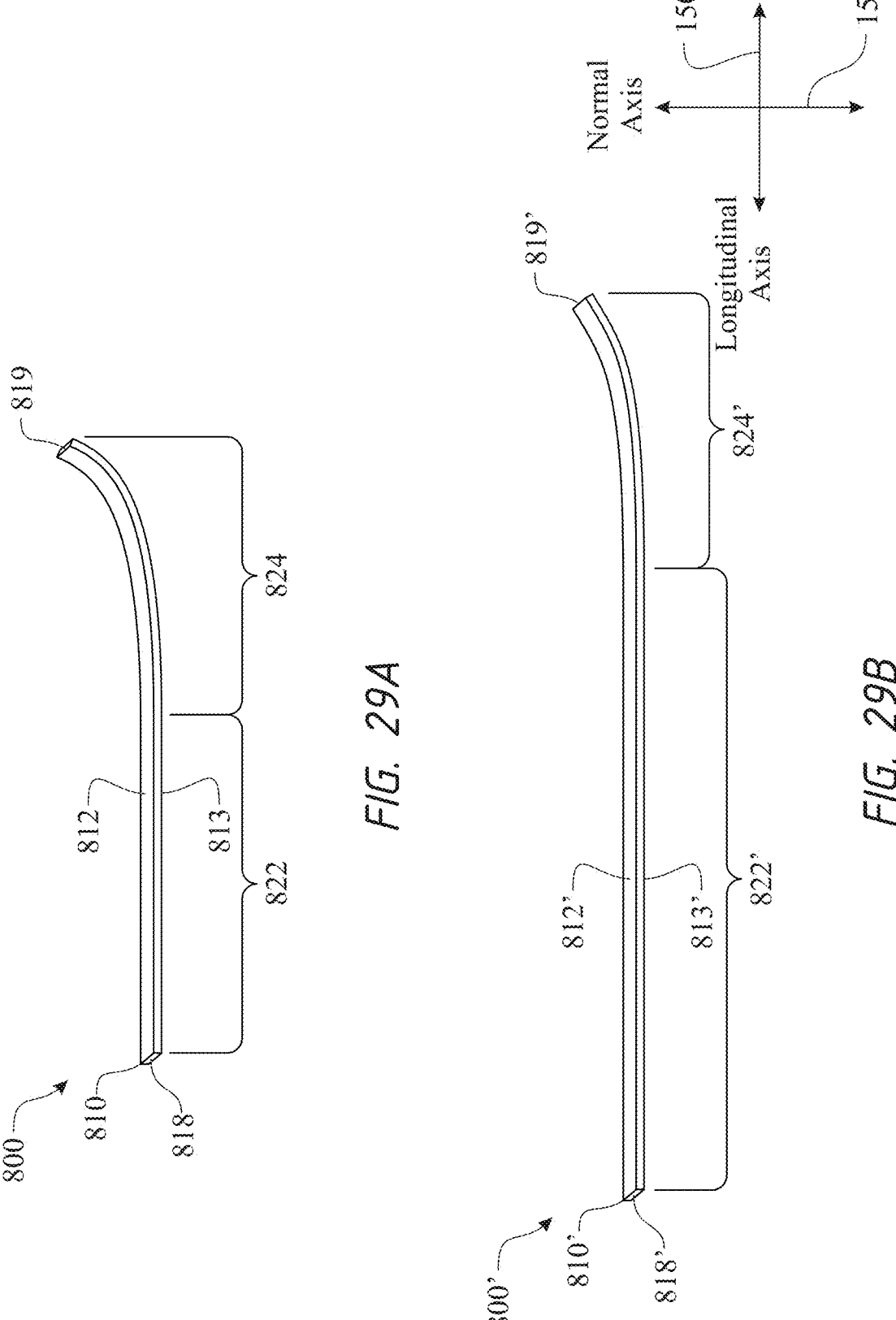
FIG. 29A presents a side top isometric view of an exemplary smaller cannula or smaller cannula guide, the exemplary smaller cannula comprising a linear segment and an arched segment.
FIG. 29B presents a side top isometric view of an exemplary larger cannula or larger cannula guide, the exemplary larger cannula comprising a linear segment and an arched segment.

The use of cannulae of different configurations can aid in directing the cannula through the desired passageway. Two cannulae 800, 800' having differing shapes and lengths are illustrated in FIGS. 29A and 29B.

The short and long cannula guiding passageway entrance 770 can optionally include several features to aid in guiding the cannula to a subsequent passageway orifice. Each exemplary cannula 800, 800' comprising a cannula body 810, 810'. The cannula body 810, 810' can be of any suitable shape, including circular, oval, elliptical, square, rectangular, and the like. The circular shape enables rotation, whereas the non-circular shaped versions restrict any rotation. The cannula body 810, 810' is hollowed allowing passage of the staged reinforcement composition 650 therethrough. Orientation of each cannula body 810, 810' can be defined by a cannula body first guide surface 812, 812', a cannula body second, opposite guide surface 813, 813', a cannula body guide end 818, 818', and a cannula body leading end 819, 819'. The cannula body 810, 810' is preferably segmented into two portions, a cannula body linear segment 822, 822' and a cannula body arched segment 824, 824'. The cannula body arched segment 824, 824' enables guidance from a horizontal insertion orientation to a more vertical direction for insertion into the adjacent vertebra 100, 110. Details of the use of the cannula body arched segment 824, 824' are presented in FIGS. 30, 31, 33, and 34.

The method of using the intervertebral spacer 700 replicates the bone reinforcing composition delivery system flow diagram 402. A partial listing of the twelve (12) exemplary distinct optional cannula pathways described above are presented in a suggested group of cannula pathways. In use, the decision determining if all delivery locations have been used for dispensing of the staged reinforcement composition 650 includes a step of determining which or all of the available cannula pathways are to be used by the surgical team for dispensing of the staged reinforcement composition 650 into the adjacent first joint member 100 and the adjacent second joint member 110. Although the exemplary intervertebral spacer 700 includes twelve (12) exemplary distinct optional cannula pathways, it is understood that the intervertebral spacer 700 can include any suitable number of useable cannula pathways and bone reinforcement composition distribution paths. The cannula pathways can be independent of one another or partially combined, as illustrated. The surgical team would guide the composition delivery cannula 600 through each of the selected or predetermined cannula pathways and would preferably record each used pathway for documentation. The process would be repeated (decision block 441) until the staged reinforcement composition 650 is dispensed through each selected or predetermined cannula pathway of the number of cannula pathways integrated into the intervertebral spacer 700.

Figure 30:
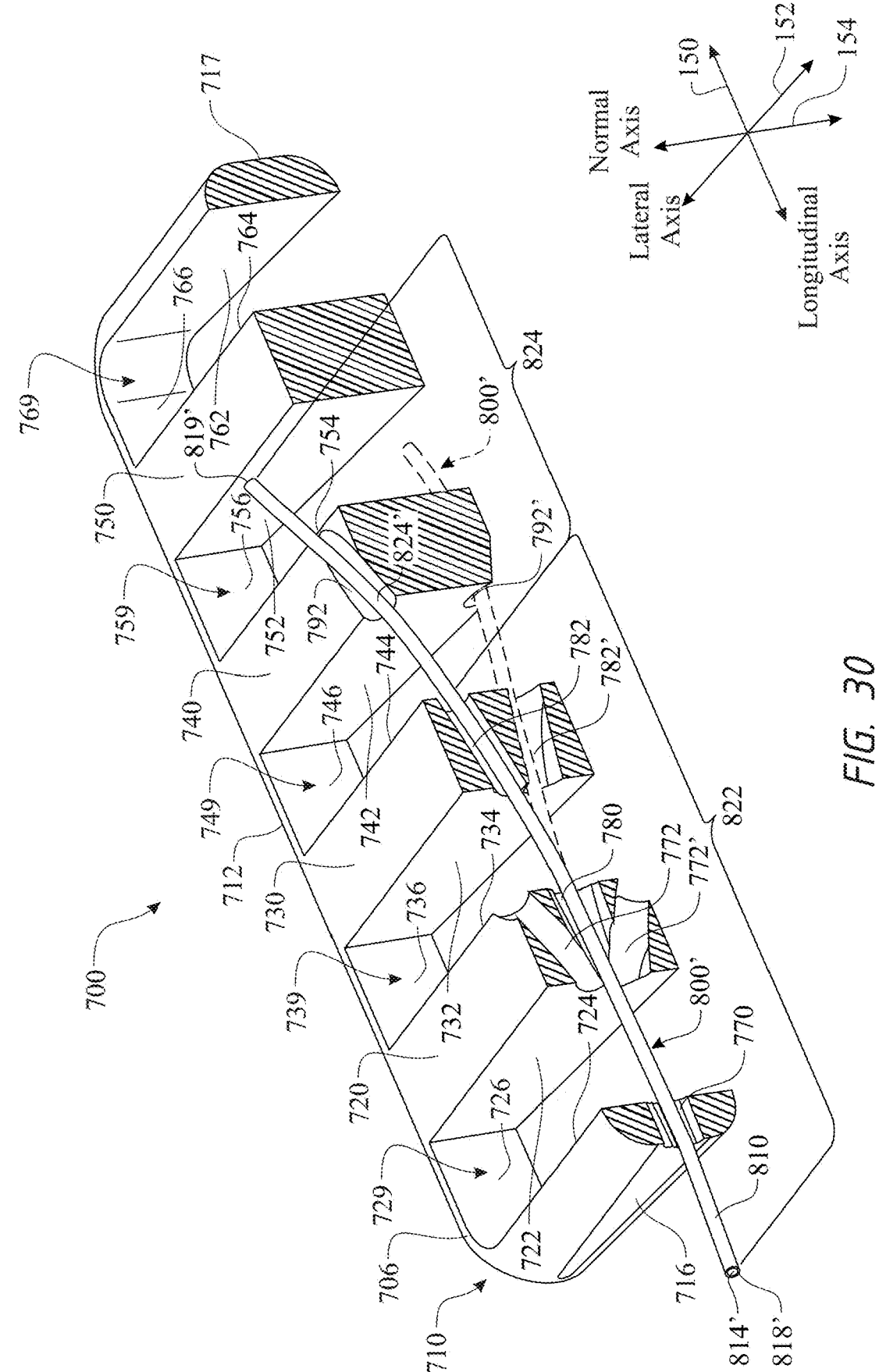
FIG. 30 presents a top side sectioned isometric view of the exemplary intervertebral spacer originally introduced in FIG. 27, the section being taken slightly offset of center of the series of cement injection guides, the section being identified by section line 28-28 of FIG. 27, the illustration presenting an insertion of the larger cannula through the intervertebral spacer following an exemplary distal inward bone reinforcement composition delivery pathway.
Figure 33:
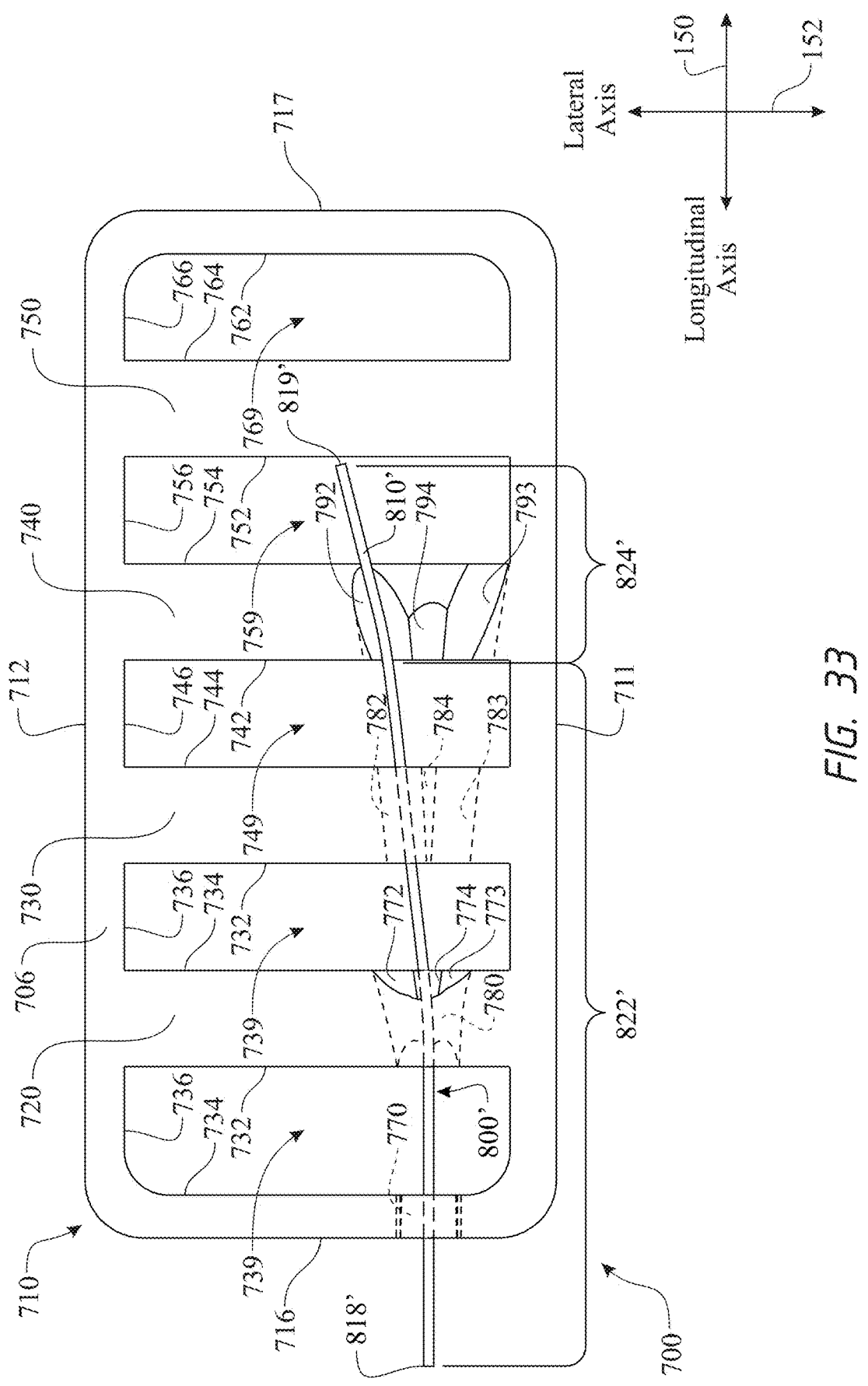
FIG. 33 presents a top plan view of the exemplary intervertebral spacer originally introduced in FIG. 27 providing a second viewing angle of the insertion of the larger cannula through the intervertebral spacer following the exemplary distal inward bone reinforcement composition delivery pathway.

Examples of dispensing of the staged reinforcement composition 650 using different cannula pathways are presented in FIGS. 30, 31, 33, and 34. In FIGS. 30 and 33, the long cannula 800' is inserted into the intervertebral spacer 700 following the upper inwardly directed distal passageway 770, 772, 782, 792. Also presented in FIG. 30, the long cannula 800' (shown in broken line) is inserted into the intervertebral spacer 700 following a lower inwardly directed distal passageway 770, 772', 782', 792'. The short cannula 800 can include a short cannula body 810 with a cannula guide surface 814, 814'. The short cannula body 810 can comprise a short cannula body guide end 818, short cannula body leading end 819, short cannula body linear segment 822, and short cannula body arched segment 824.

Figure 31:
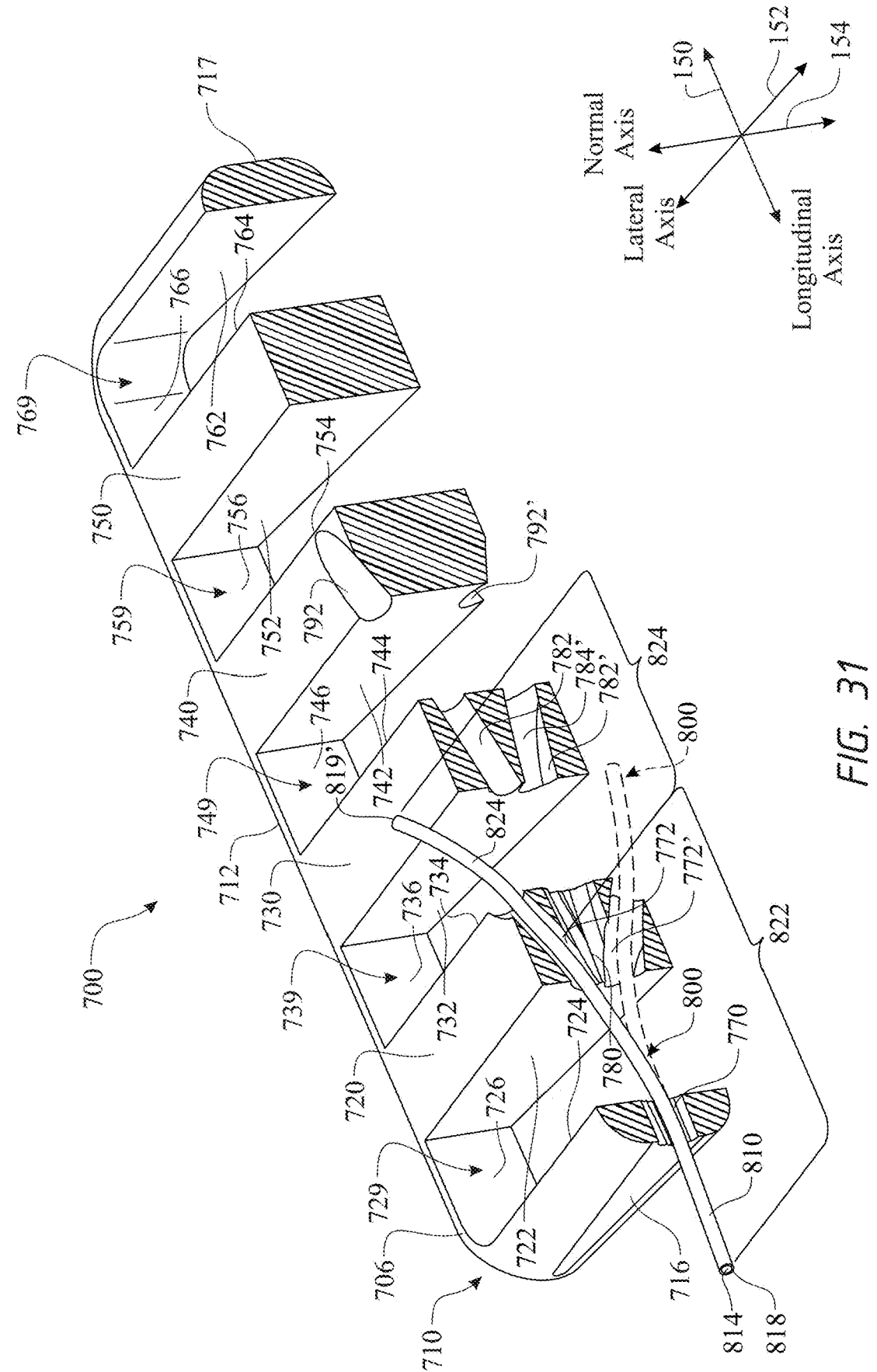
FIG. 31 presents a top side sectioned isometric view of the exemplary intervertebral spacer originally introduced in FIG. 27, the section being taken slightly offset of center of the series of cement injection guides, the section being identified by section line 28-28 of FIG. 27, the illustration presenting an insertion of the smaller cannula through the intervertebral spacer following an exemplary proximal inward bone reinforcement composition delivery pathway.
Figure 32:
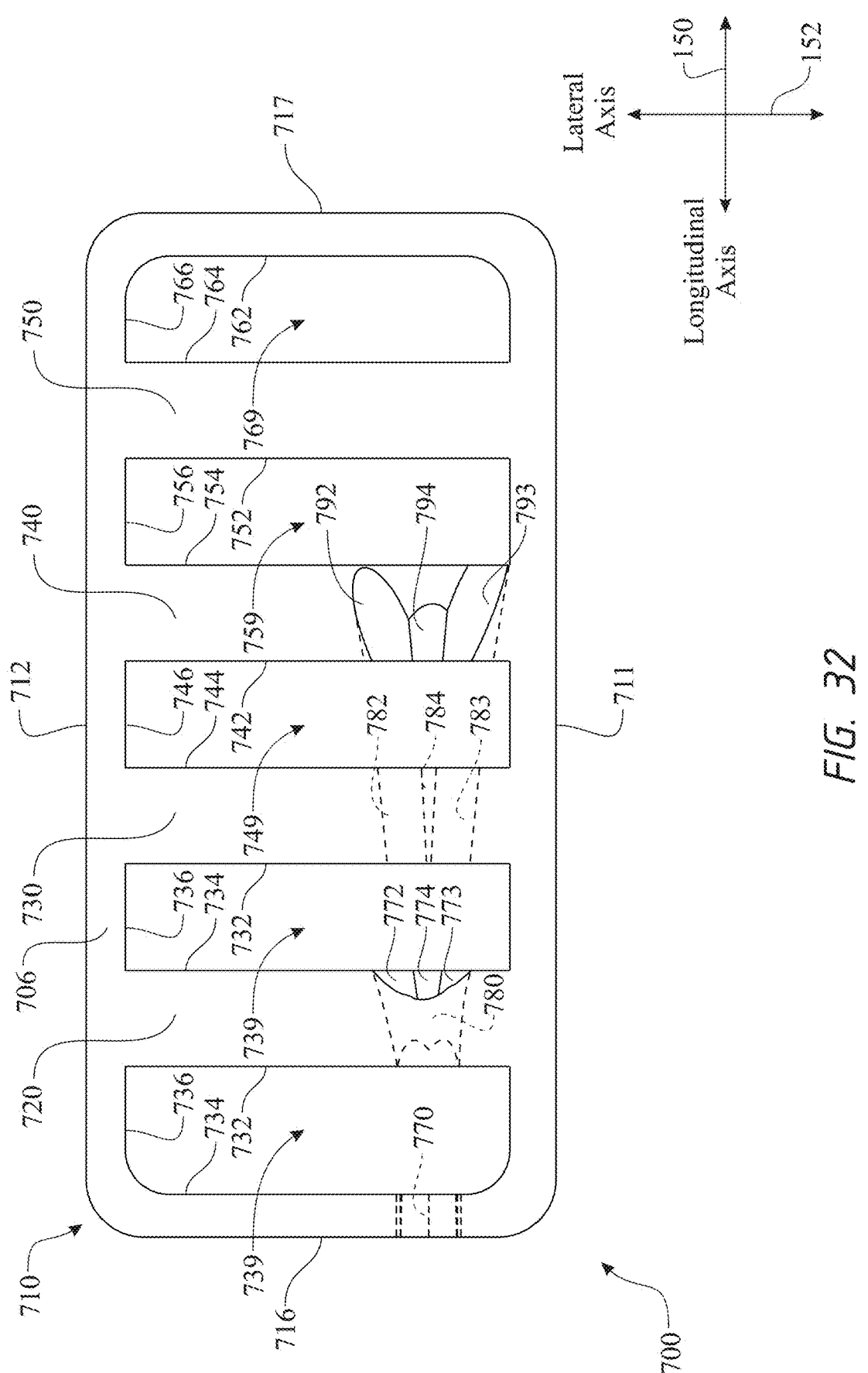
FIG. 32 presents a top plan view of the exemplary intervertebral spacer originally introduced in FIG. 27.
Figure 34:
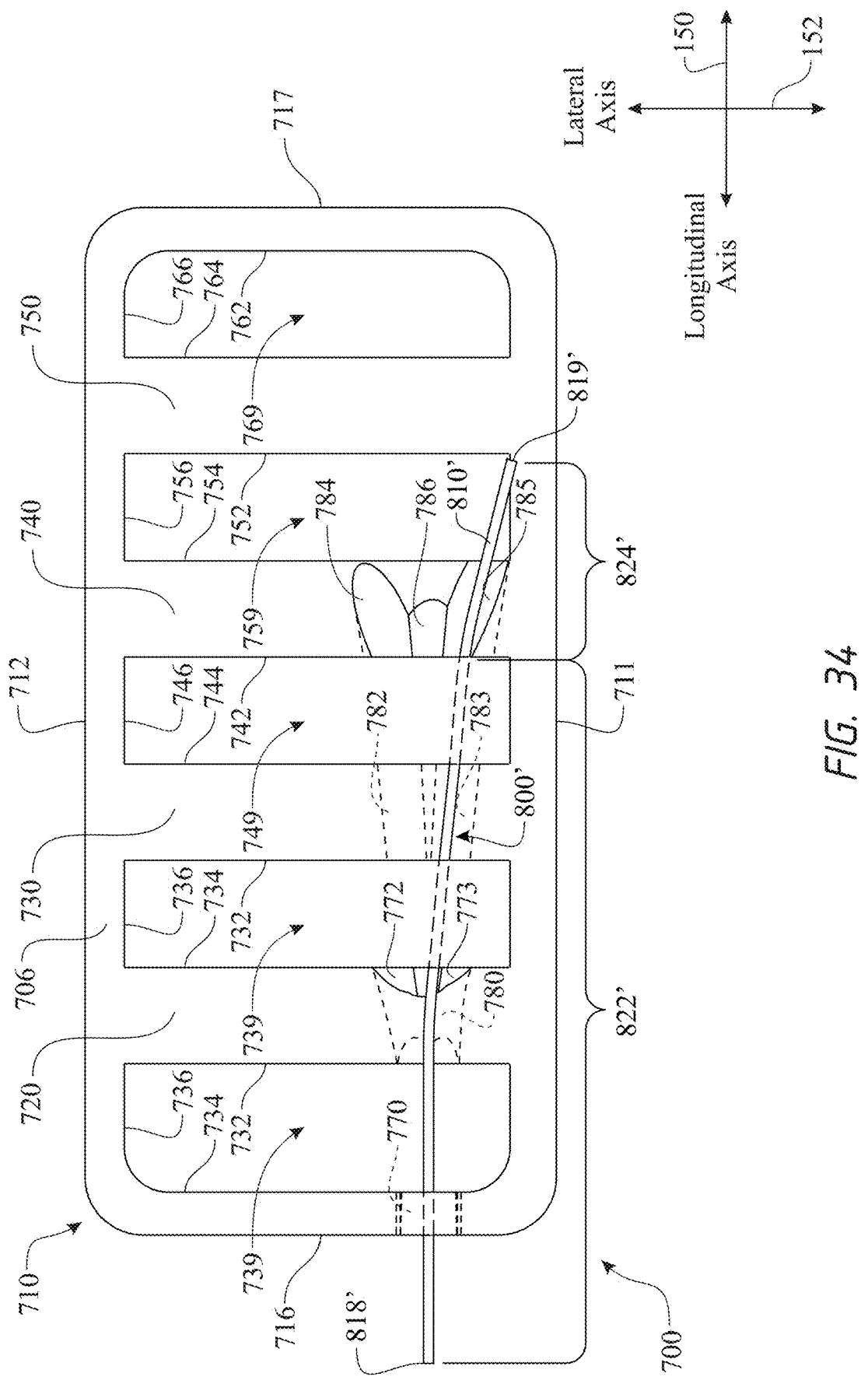
FIG. 34 presents a top plan view of the exemplary intervertebral spacer originally introduced in FIG. 27 providing a top plan view of the insertion of the larger cannula through the intervertebral spacer following an exemplary distal outward bone reinforcement composition delivery pathway.

In FIG. 31, the short cannula 800 is inserted into the intervertebral spacer 700 following the upper inwardly directed proximal passageway 770, 772. In FIG. 34, the long cannula 800' is inserted into the intervertebral spacer 700 following the upper outwardly directed distal passageway 770, 773, 783, 793. The spacer body 710 can include one or more passageways, network of passageways, and/or interconnected passageways for guiding a cannula. For example, the spacer body 710 includes passageways including the cannula guiding entrance 770 that connects to several discharge and intermediary passageways. These can include upper interior discharge passageway 772, upper outer discharge passageway 773, intermediary guiding passageway 780, upper interior intermediary passageway 782, upper outer intermediary passageway 783, upper central intermediary passageway 784, central intermediary passageway 785, and lower intermediary passageway 786.

The complex internal structure of the intervertebral spacer 700, with its multiple chambers and intricate network of passageways, can facilitate targeted cement delivery. The various chambers can allow for differential filling with bone graft materials or cement, while the passageway system can enable precise guidance of a cannula to specific regions within the spacer body 710 or adjacent vertebral tissue. This design can allow for customized cannula delivery, cement distribution patterns, and/or potentially enhancing the stability and integration of the intervertebral spacer 700 with surrounding bone structures.

Figure 35:
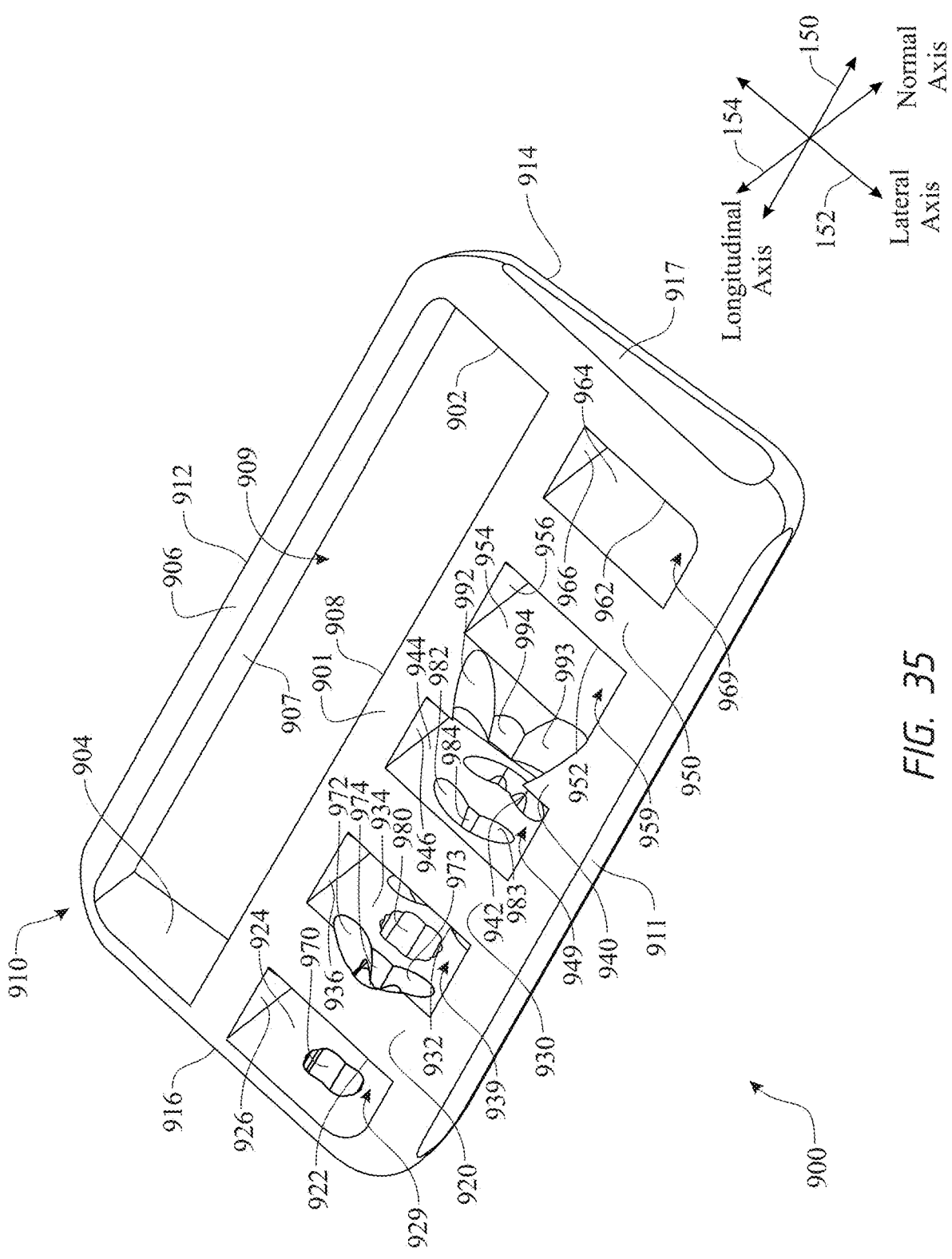
FIG. 35 presents a top side isometric view introducing a variant of the exemplary intervertebral spacer originally introduced in FIG. 27, the variant of the intervertebral spacer introducing an intervertebral spacer body bone graft chamber.

An intervertebral spacer 900, illustrated in FIG. 35, is a modified variant of the intervertebral spacer 700. The intervertebral spacer 900 includes a majority of the elements of the intervertebral spacer 700. Elements of the intervertebral spacer 900 that are shared by the intervertebral spacer 700 are numbered the same as the like elements of the intervertebral spacer 700, while preceded by the numeral "9." The intervertebral spacer 900 introduces an interverte-bral device body elongated sectioning panel 901. The transversing panels 920, 930, 940, 950 extend between facing surfaces of an intervertebral device body trailing (broader) panel 911 and the intervertebral device body elongated sectioning panel 901. A combination of a bone graft chamber interior surface 908 of an elongated sectioning panel 901, bone graft chamber interior surface 907 of an body leading (narrow) panel 912, an bone graft chamber interior surface 904 of a body first tapering side panel 916, and a bone graft chamber interior surface 902 of an second tapering side panel 917 collectively define an intervertebral device body bone graft chamber 909. The intervertebral device body bone graft chamber 909 is provided to receive a volume of bone graft during the surgical procedure. In the intervertebral spacer 700, the cannula directing pathways are off-centered respective to the transversing members or panels 720, 730, 740, 750. In the intervertebral spacer 900, the cannula directing pathways are generally centered respective to the transversing panels 920, 930, 940, 950.

The intervertebral spacer 900 includes a spacer body 910 defining panels and internal chambers. The spacer body 910 has an upper vertebral contacting surface 906 and a lower vertebral contacting surface 914.

The spacer body 910 is bounded by one or more walls or panels. In some embodiments, the spacer body 910 includes a trailing panel 911, a leading panel 912, a first tapering side panel 916, and a second tapering side panel 917. An elongated sectioning panel 901 extends between these boundary panels, dividing the spacer body 910 into distinct regions. Different materials can be delivered into the distinct regions (e.g., voids, chambers, openings).

Multiple transversing panels extend between the boundary panels, including a first transversing panel 920, a second transversing panel 930, a third transversing panel 940, and a fourth transversing panel 950. These panels create separate chambers within the spacer body 910, including a first chamber 929, a second chamber 939, a third chamber 949, and a fourth chamber 959.

A bone graft chamber 909 is defined by the sectioning panel interior surface 908, the leading panel interior surface 907, the first tapering side panel interior surface 904, and the second tapering side panel interior surface 902. The bone graft chamber 909 can be configured to receive and hold bone graft material during the surgical procedure.

The spacer body 910 includes one or more passageways for guiding a cannula through the spacer body 910 and into adjacent tissue. A cannula guiding entrance 970 connects to multiple discharge pathways, including some or all of the interior discharge passageway 972, an upper outer discharge passageway 973, an upper central discharge passageway 974, and a central discharge passageway 975. Additional guiding passageways include an upper interior guiding passageway 982, an upper outer guiding passageway 983, and an upper central guiding passageway 984.

In some cases, the elongated sectioning panel 901 can serve as a barrier between the bone graft chamber 909 and the cement flow regions of the spacer body 910. This configuration can allow for simultaneous accommodation of bone graft material and cement delivery within the same intervertebral spacer 900.

The cement flow regions, which can include the first chamber 929, second chamber 939, third chamber 949, and fourth chamber 959, can be designed to allow bone cement to flow through specific areas of the intervertebral spacer 900. These chambers can be interconnected by one or more guiding passageways to create a network for cement distribution.

The bone graft chamber 909 can be accessed separately from the cement flow regions, allowing a surgeon to pack bone graft material into the chamber before, during, or after the cement delivery process. This design can facilitate both initial stability through cement fixation and long-term biological integration through bone graft incorporation.

In some cases, the intervertebral spacer 900 can include porous surfaces or openings in the bone graft chamber 909 to promote bone ingrowth and fusion with adjacent vertebral bodies. The cement flow regions can be designed with different porosity characteristics to control cement flow and distribution.

The combination of a dedicated bone graft chamber 909 and separate cement flow regions in the intervertebral spacer 900 can provide a versatile implant that addresses both immediate stabilization needs through cement delivery and long-term fusion goals through bone graft placement. This dual-function design can potentially improve overall surgical outcomes in spinal fusion procedures.

The spacer body 910 may include a first intermediary transversing panel 920 with a first chamber interior surface 922 that helps define the boundaries of the first chamber 929. Adjacent to this, the first tapering side panel 916 may have a first chamber interior surface 924 that further encloses the first chamber 929. The leading panel 912, which may be narrower than other panels, can include a first chamber interior surface 926 that completes the enclosure of the first chamber 929.

A second intermediary transversing panel 930 may be positioned within the spacer body 910, featuring a second chamber interior surface 932 that contributes to defining the second chamber 939. The first intermediary transversing panel 920 may also have a second chamber interior surface 934 facing the second chamber 939. The leading panel 912 may include a second chamber interior surface 936 that forms part of the second chamber 939 boundary.

The spacer body 910 may incorporate a third intermediary transversing panel 940 with a third chamber interior surface 942 that helps shape the third chamber 949. The second intermediary transversing panel 930 may have a third chamber interior surface 944 that faces into the third chamber 949.

A fourth intermediary transversing panel 950 may be present, featuring a fourth chamber interior surface 952 that contributes to defining the fourth chamber 959. The third intermediary transversing panel 940 may include a fourth chamber interior surface 954 that faces the fourth chamber 959. The leading panel 912 may have a fourth chamber interior surface 956 that forms part of the fourth chamber 959.

The spacer body 910 may also include a fifth chamber 969, which can be partially defined by the second tapering side panel 917 with a fifth chamber interior surface 962. The fourth intermediary transversing panel 950 may have a fifth chamber interior surface 964 facing into the fifth chamber 969. The leading panel 912 may include a fifth chamber interior surface 966 that completes the enclosure of the fifth chamber 969.

For guiding cannulas, the spacer body 910 may incorporate a cannula guiding entrance 970 that can accommodate both short and long cannulas. For short cannulas, the spacer may include an upper interior discharge passageway 972, an upper outer discharge passageway 973, and an upper central discharge passageway 974.

Long cannulas may be guided through a collective intermediary guiding passageway 980 that branches into more specific pathways. These may include an upper interior guiding (e.g., guiding intermediary) passageway 982, an upper outer guiding intermediary passageway 983, and an upper central guiding intermediary passageway 984. These intermediary passageways may lead to corresponding discharge passageways for long cannulas, including an upper interior guiding discharge passageway 992, an upper outer guiding discharge passageway 993, and an upper central guiding discharge passageway 994.

This intricate system of chambers and passageways may allow for differential filling with bone graft materials or cement, potentially enhancing the stability and integration of the intervertebral spacer 900 with surrounding bone structures. The design may enable surgeons to customize material distribution patterns and access specific regions within the spacer body 910 or adjacent vertebral tissue during surgical procedures.

Figure 36:
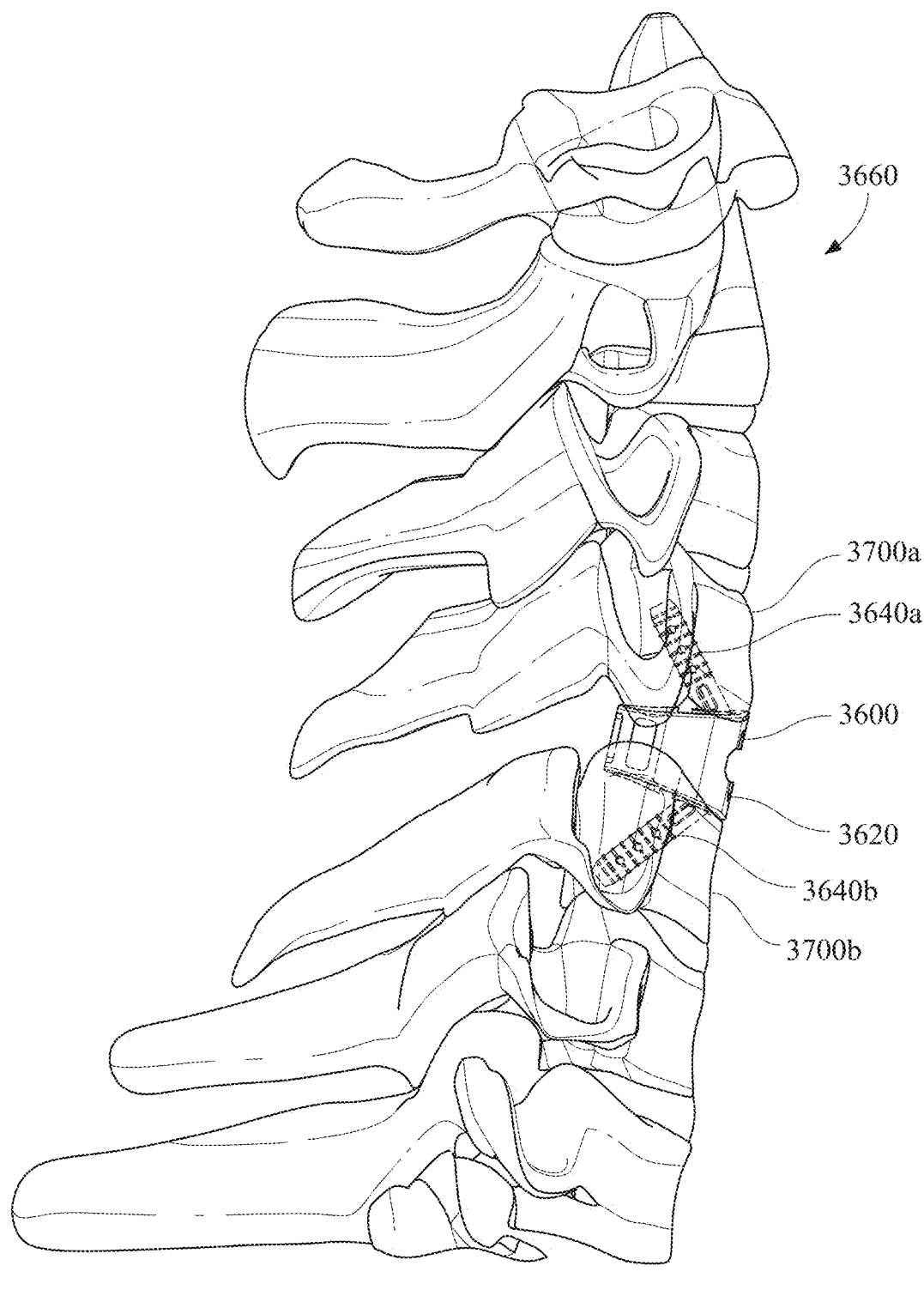
FIG. 36 is a side view of an anterior implant assembly positioned along a cervical region of a subject's spine.

FIG. 36 is a side view of an anterior intervertebral implant assembly 3600 positioned along a cervical region of a subject's spine. The implant assembly 3600 is configured to assist with delivery of material and includes an intervertebral cage or body 3620 ("body 3620") and hollow upper and lower anchors 3640a, 3640b (collectively, "anchors 3640"). The description of the intervertebral cages of FIGS. 1-35 applies to the body 3620 unless indicated otherwise. The description of one of the anchors applies to the other unless indicated otherwise.

The intervertebral body 3620 can include one or more flow-through features configured to receive pairs of upper and lower anchors 3640 such that flowable material can be delivered through the upper and lower anchors 3640 and into upper and lower vertebrae 3700a, 3700b. The delivered material can harden to rigidly lock together, for example, the intervertebral implant assembly 3600 and vertebrae 3700a, 3700b, components of the implant assembly 3600, or combinations thereof. The delivered material can harden within, for example, 1-5 minutes, 10 minutes, 20 minutes, 30 minutes, hours, days, weeks, months, or another suitable length of time. In some embodiments, the flowable material is bone cement that hardens to form a hardened bone cement structure that extends through, for example, the upper anchor 3640a, the body 3620, and/or the lower anchor 3640b. The hardened bone cement can also extend at least partially through interior tissue of the upper and lower vertebrae 3700a, 3700b, respectively, to, for example, reinforce one or both vertebrae 3700a, 3700b, inhibit or prevent cracking, strengthen anatomy, improve locking of the implant assembly 3600 to the anatomy, inhibit or prevent movement of the anchors 3640, inhibit or prevent movement of the joint, or combinations thereof.

The intervertebral body 3620 and/or anchors 3640 can include one or more flow-through features. The flow-through features can include one or more passageways (e.g., interconnected passageways), cavities, bifurcated fixation holes, spaced-apart pairs of bifurcated fixation holes, fixation holes, etc. The number and configuration of flow-through features can be selected based on, for example, an amount of material to be contained by the intervertebral implant assembly 3600, amount of material to be delivered into the patient (delivered between anatomy, into anatomy, etc.), configuration of the implantation site (e.g., cervical region, lumbar region, etc.), planned anatomical correction, fusion procedure, or combinations thereof.

Figure 37:
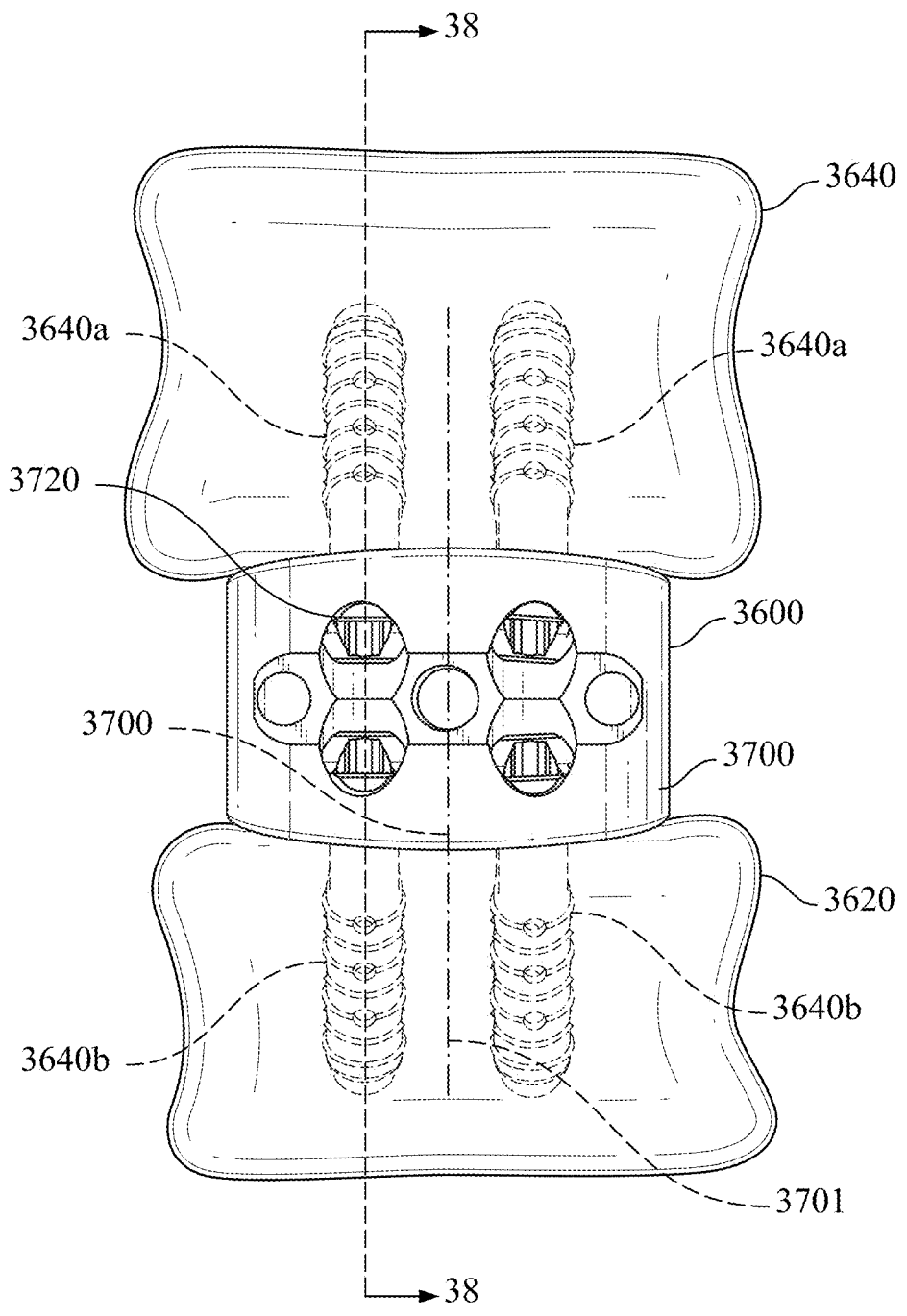
FIG. 37 is an anterior view of the implant assembly positioned along the cervical region of FIG. 36.
Figure 38:
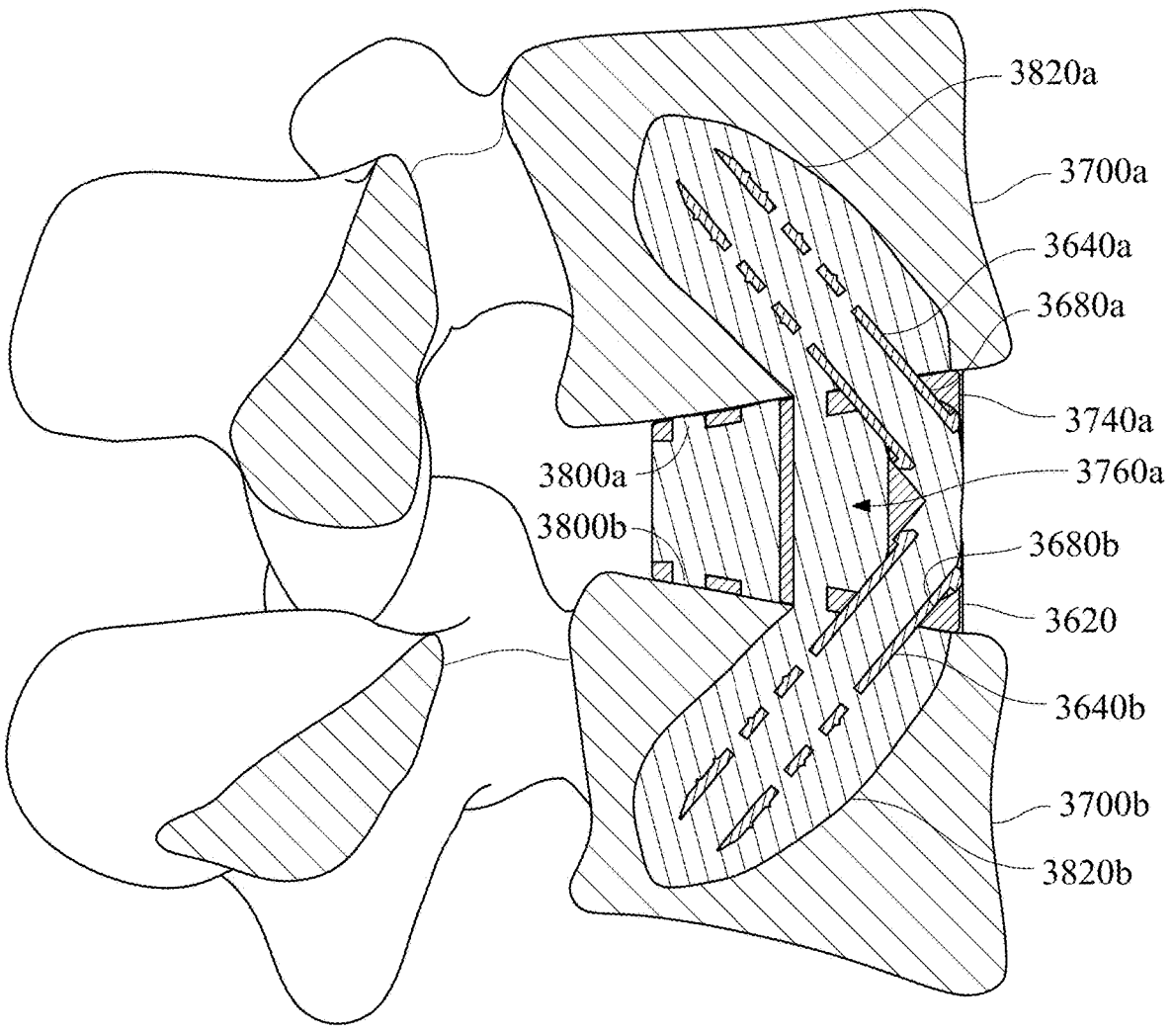
FIG. 38 is a cross-sectional view of the implant assembly and spine taken along line 38-38 of FIG. 37.

FIG. 37 is an anterior view of the implant assembly 3600 of FIG. 36. FIG. 38 is a cross-sectional view of the implant assembly 3600 and anatomy taken along section lines 38-38 of FIG. 37. Referring now to FIG. 37, the upper anchors 3640a can be positioned on opposite sides of a plane 3701

(e.g., parasagittal plane, mid sagittal plane, etc.) of the body 3620. Heads 3720 (one identified in FIG. 37) can be accessed to hammer, pull, or rotate the upper anchors 3640a. The lower anchors 3640b can be positioned on opposite sides of the plane 3701 of the body 3620. The anchors 3640 on the same side of the parasagittal plane 3701 can be vertically aligned such that flowable material can flow between the hollow passageways of the vertically aligned anchors. Additionally, the vertically aligned anchors can block or obstruct one another to inhibit or prevent anchor pullout. In this manner, the vertically adjacent anchors can cooperate to ensure proper fixation.

Referring now to FIG. 38, bone cement 3820a, 3820b locks together components of the implant assembly 3600 and the vertebrae 3700a, 3700b. The intervertebral body 3620 is positioned between vertebral endplates 3800a, 3800b of the vertebrae 3700a, 3700b, respectively. The inner body 3620 includes a side wall 3740 and interconnected passageways in the form of a bifurcated opening or through hole 3770 ("bifurcated through hole 3770"). The bifurcated through hole 3770 has an upper opening 3680a that receives an upper anchor 3640a and a lower opening 3680b that receives a lower anchor 3640b. Bifurcated through holes are discussed in connection with FIG. 44A.

With continued reference to FIG. 38, anchors 3640a, 3640b and the body 3620 define a generally continuous bone cement flow path such that, during implantation, bone cement can flow out of the anchors 3640a, 3640b and into the vertebrae 3700a, 3700b, respectively. For example, an upper region of bone cement 3820a can extend at least partially through the intervertebral body of the upper vertebra 3700a and a lower region of bone cement 3820b can extend through at least a portion of the vertebral body of the lower vertebra 3700b. The bone cement can also partially or completely fill spaces (e.g., cavities, passageways, gaps, etc.) of the intervertebral implant assembly 3600.

Figures 39, 40:
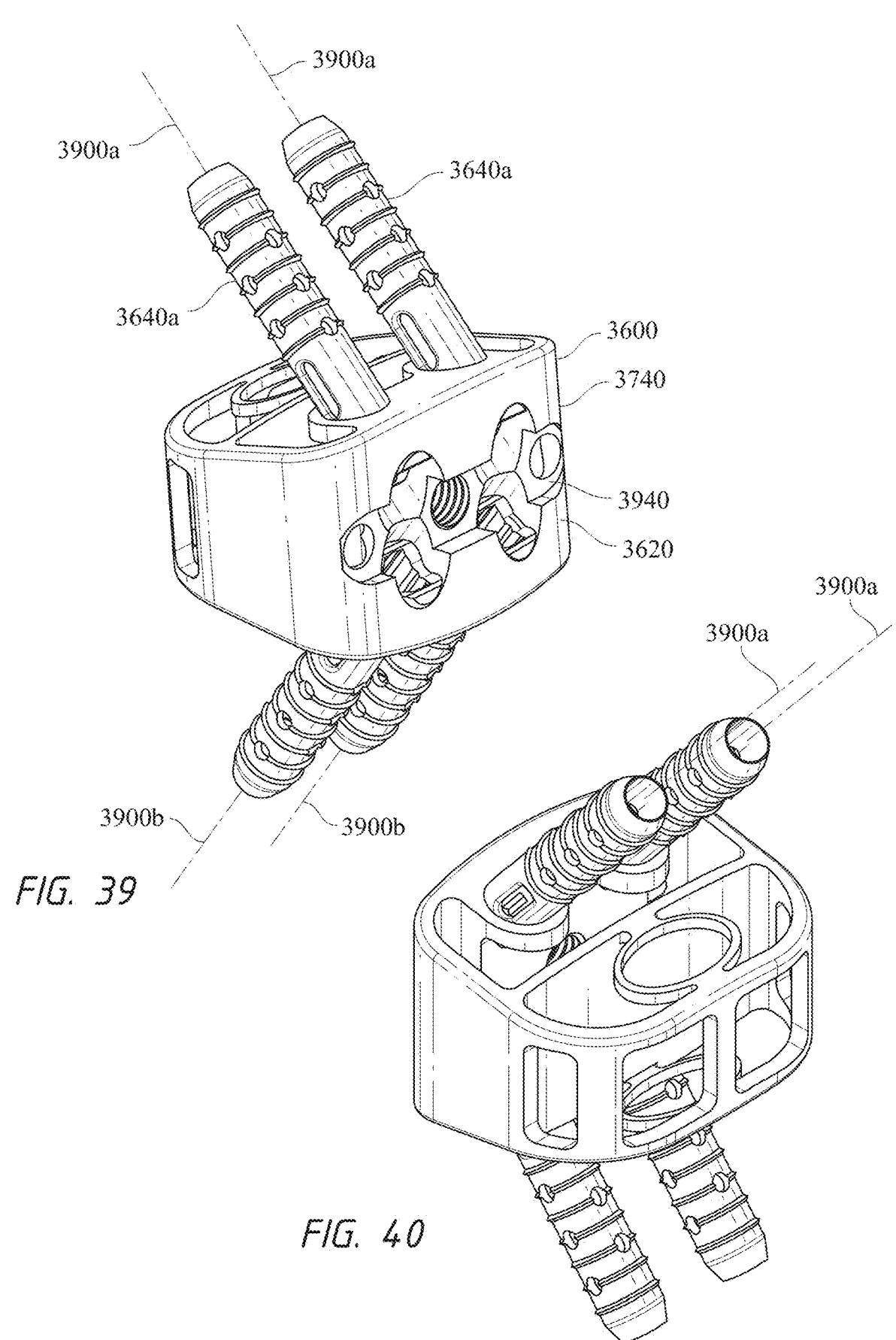
FIG. 39 is an isometric front top view of an implant assembly in accordance with embodiments of the technology.
FIG. 40 is an isometric back top view of the implant assembly of FIG. 39.

FIG. 39 is an isometric front top view of an intervertebral implant assembly 3600 in accordance with embodiments of the technology. FIG. 40 is an isometric back top view of the intervertebral implant assembly 3600 of FIG. 39. Referring now to FIG. 39, the body 3620 has a side wall 3740 including an entrance 3940 defining openings for receiving the anchors 3640a, 3640b, cannulas, or instruments for holding the anchor body 3620. The body 3620 can have chambers, porous regions, cavities, and other features for receiving bone graft material. Referring now to FIGS. 39 and 40, the upper anchors 3640a can extend along trajectories 3900a, 3900a (collectively, "trajectories 3900") generally parallel to each other. In some embodiments, the trajectory 3900a can be generally parallel to, or lie along, a mid-central plane (e.g., mid-sagittal plane 4100 of FIGS. 41 and 42, parasagittal plane, etc.) of the body 3620. In some embodiments, one or both of the anchors 3640 have longitudinal axes generally parallel to a parasagittal plane of the intervertebral body 3620. The trajectories, spacing, and/or number of anchors 3640 can be selected based on the procedure to be performed.

Figures 41, 42, 43:
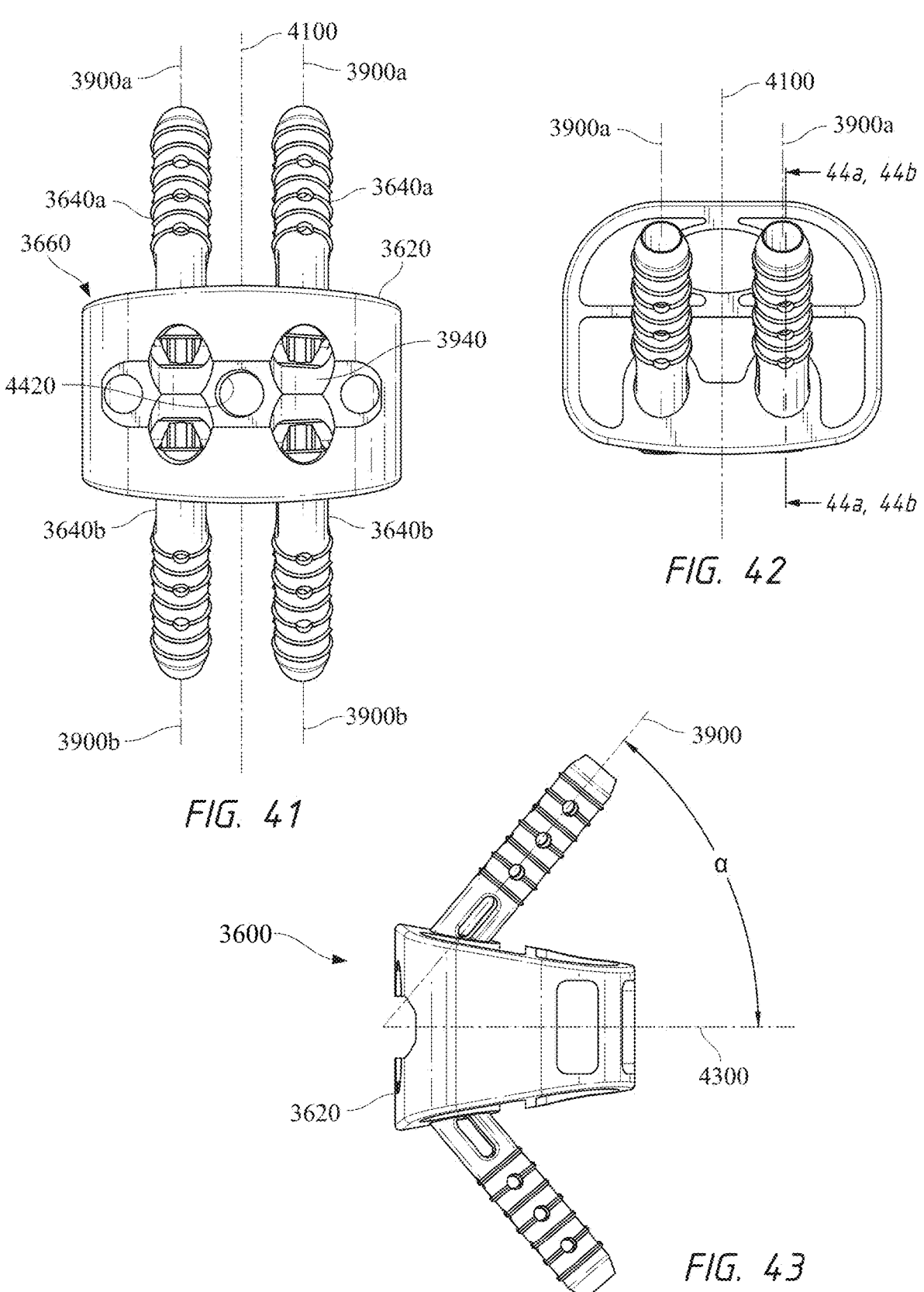
FIG. 41 is a front view of the implant assembly of FIG. 39.
FIG. 42 is a top view of the implant assembly of FIG. 39.
FIG. 43 is a side view of the implant assembly of FIG. 39.

FIG. 41 shows the entrance 3940 for accessing interior regions of the body 3620, heads of the anchors 3640, fixation or attachment features 4120 (e.g., threaded holes, clipping features, or the like), or the like. In some embodiments, the entrance 3940 is connected to the bifurcated through hole to allow the anchors 3640 to be inserted through the body 3620 along the trajectories 3900.

FIG. 43 is a side view of the implant assembly 3600. A longitudinal axis of and anchor trajectory 3900a and the transverse plane 4300 of the body 3620 can define an angle α in the range of 30° to 60°, 40° to 50°, or other ranges of angles. In some embodiments, the angle α can be equal to or less than 30°, 40°, 45°, 50°, 55°, 60°, or other desired angles. The angle α and the length of the anchors 3640 can be selected based on the configuration and dimensions of the patient's anatomy.

Figure 44A:
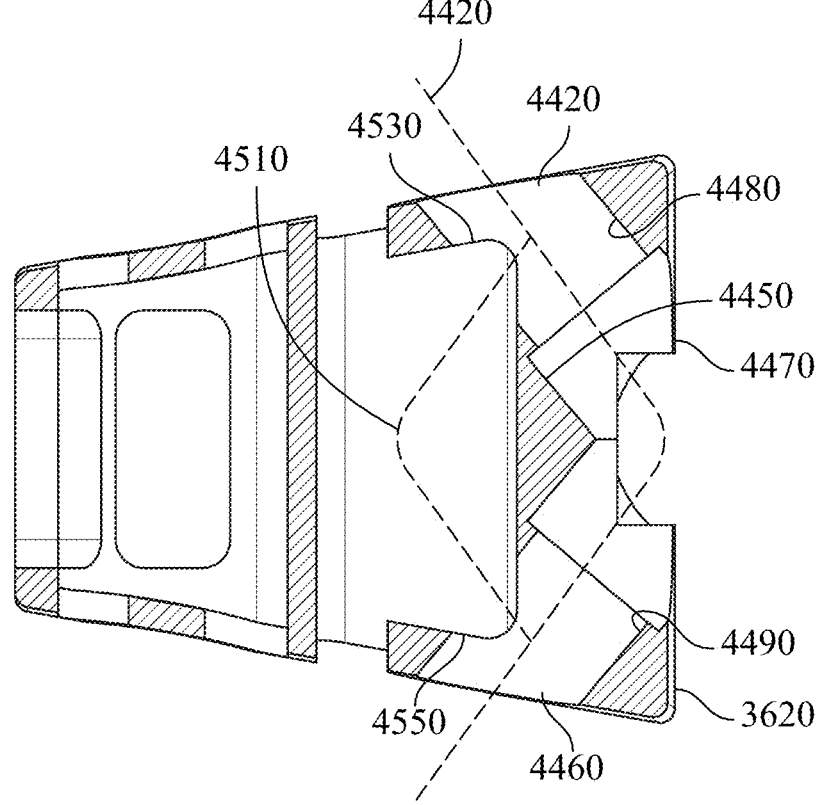
FIG. 44A is a cross-sectional view of an intervertebral body taken along line 44a-44a of FIG. 42 in accordance with embodiments of the technology.

Referring to FIG. 44A, the body 3620 defines the bone cement flow path 4420. In some embodiments, the bifurcated through hole includes an upper inlet 4440 and the angle passageway 4450 extending from the upper inlet 4440 to a lower inlet 4460. The angle passageway 4450 can have a generally V-shape configuration as viewed from the side, as shown in FIG. 44A. In some embodiments, the bone cement flow path 4420 can diverge and have an inner flow passageway 4510 that extends between openings 4530, 4550 angled toward an interior region of the body 3620. This allows cement to flow inwardly through the body 3620. The angle passageway 4450 can extend to a side wall opening 4470 positioned along an anterior side wall of the body 3620. In some embodiments, an upper portion 4480 of the angle passageway 4450 is configured to receive the upper anchor. The angle passageway 4450 can include a lower portion 4490 configured to receive the lower anchor. The upper inlet 4440 is configured to overlay a lower endplate of an upper vertebral body. This allows the anchor to be inserted through the endplate and into the interior of the vertebral body. Similarly, the lower inlet 4460 can overlay an upper endplate of the lower vertebral body.

Figure 44B:
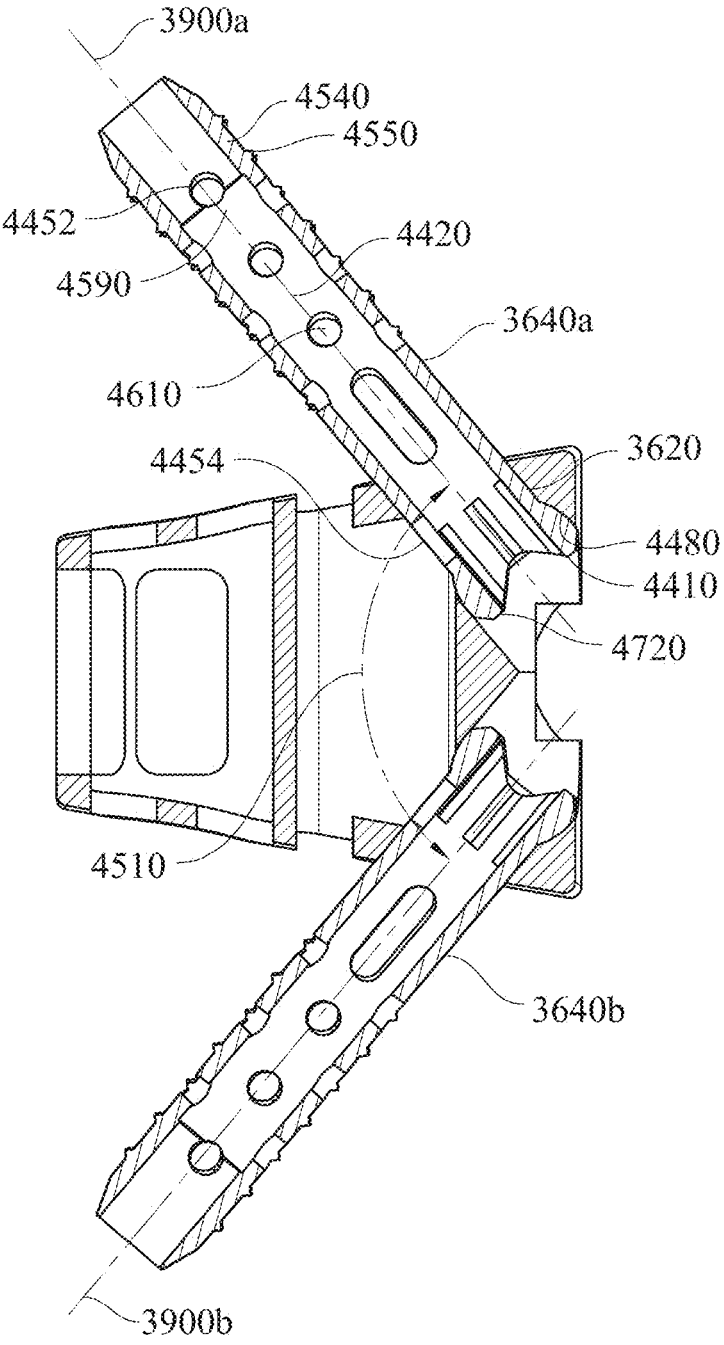
FIG. 44B is a cross-sectional view of the implant assembly taken along line 44b-44b of FIG. 42 in accordance with embodiments of the technology.

Referring now to FIG. 44B, an upper anchor 3640a is positioned the upper portion 4480 of the angle passageway 4450. A head 4410 of the anchor 4640a can be received in a complementary enlarged region 4480 of the passageway 4450. The lower anchor 3640b can be seated in a similar manner. The anchors 3640 can include one or more delivery outlets 4452 and flow-through openings 4454. The bone cement flow path 4420 can extend along an upper passageway of the upper anchor 3640a, through a central chamber (or central porous region) of the body 3620, and along a lower passageway of the lower anchor 3640b. Material can flow through the delivery outlets 4452 to exit the assembled implant, and material can flow through the flow-through openings 4454 to fill (partially or completely) the assembled implant.

Figure 45:
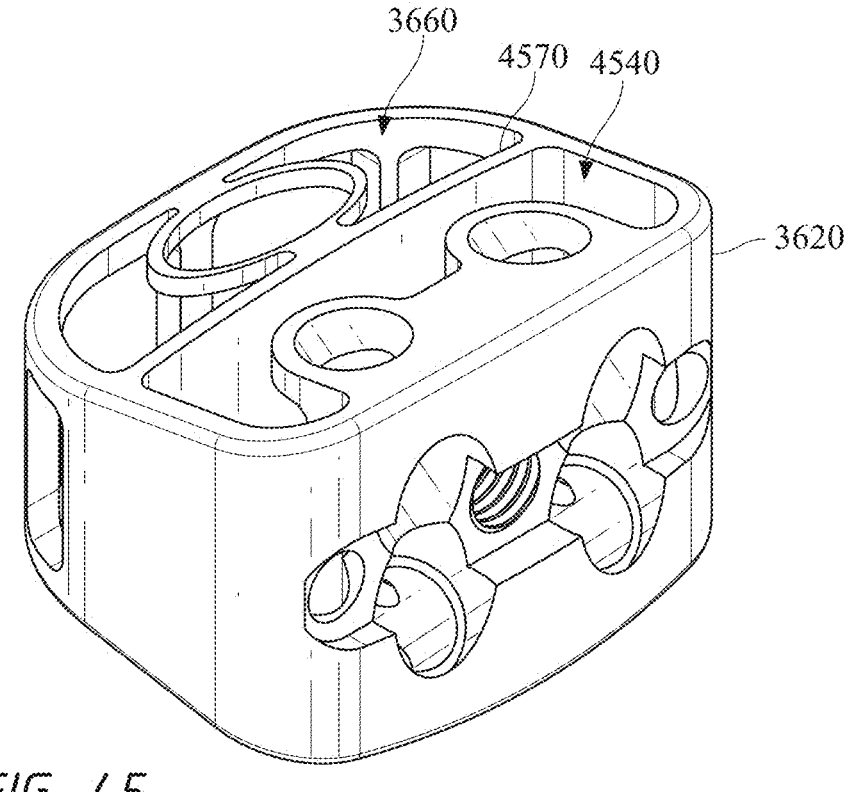
FIGS. 45 and 46 are isometric views of an intervertebral body in accordance with embodiments of the technology.
Figure 46:
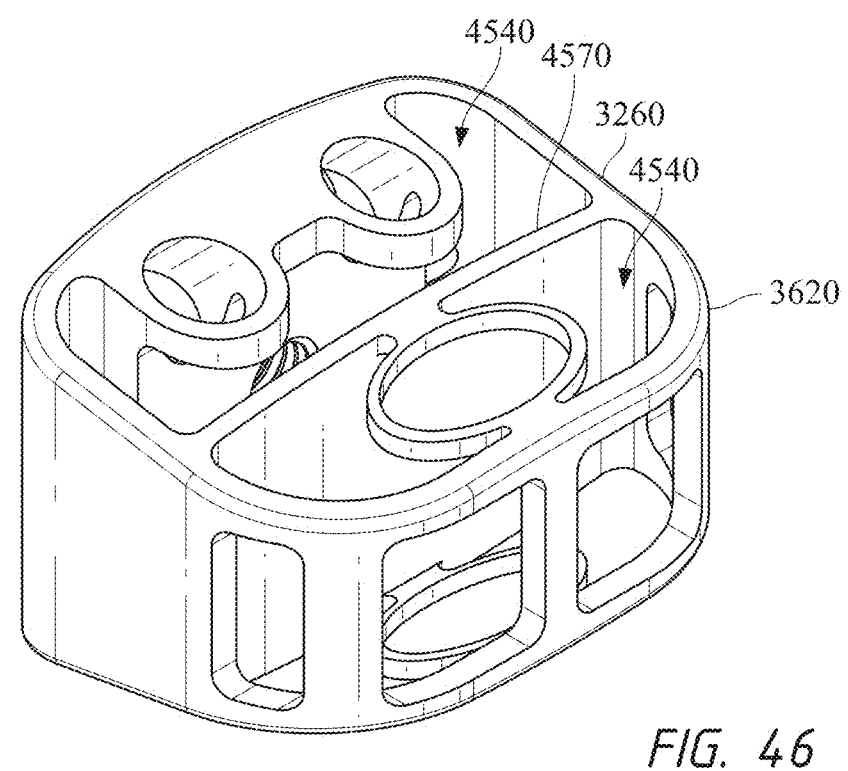
Figure 47:
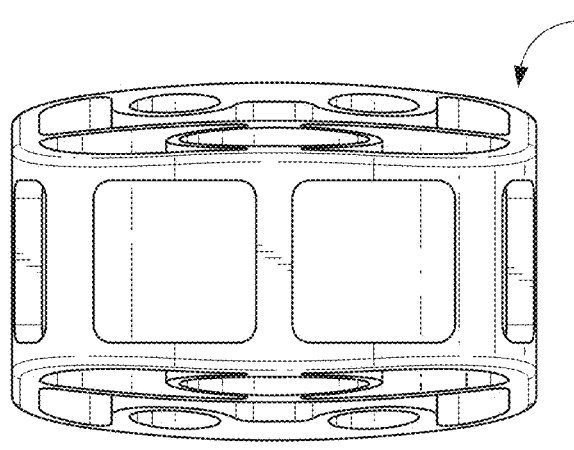
FIG. 47 is a back view of the intervertebral body of FIG. 45.
Figure 48:
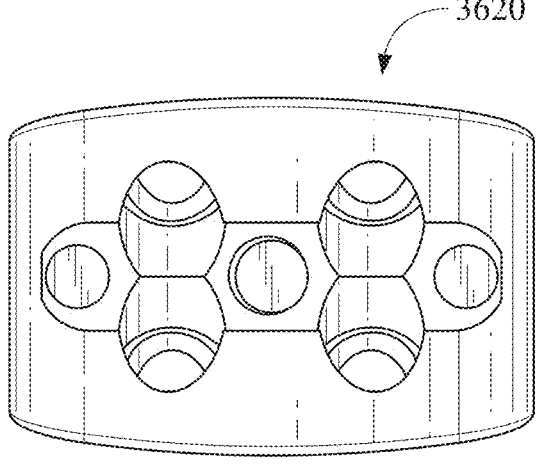
FIG. 48 is a front view of the intervertebral body of FIG. 45.
Figure 49:
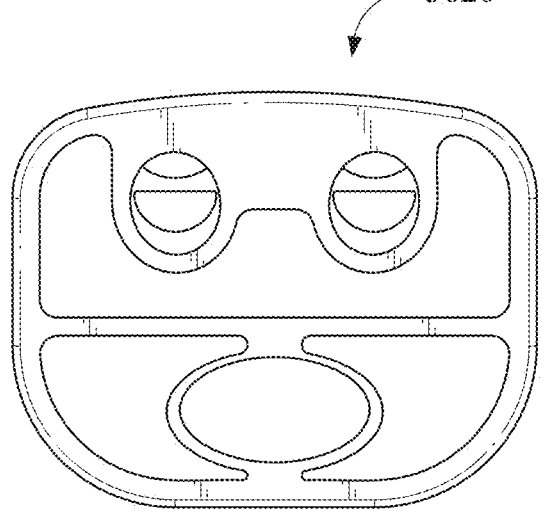
FIG. 49 is a top view of the intervertebral body of FIG. 45.
Figure 50:
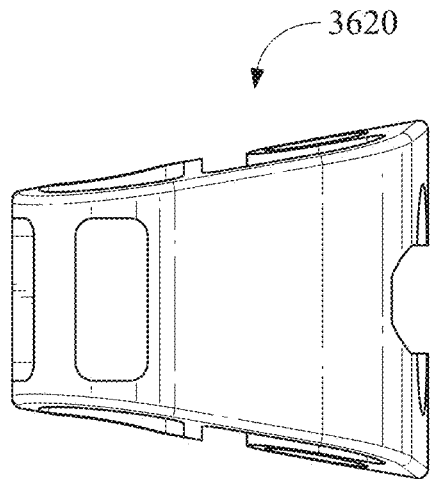
FIG. 50 is a side view of the intervertebral body of FIG. 45.

FIG. 45 is an isometric front top view of an anterior intervertebral body 3620 in accordance with embodiments of the technology, and FIG. 46 is an isometric back top view of the anterior intervertebral body 3620. The body 3620 can include a bone cement flow-through porous region 4540, a bone graft receiving region 4560, and a partition 4570. The bone graft receiving region 4560 is configured to hold bone graft material while bone cement flows through the porous region 4540. The partition 4570 can be a solid wall, a divider, or a structure for limiting, preventing, or inhibiting movement of material between different regions. The number, configuration, and position of the material receiving regions (e.g., bone cement flow-through porous regions, bone graft receiving regions, medicant receiving regions, solid regions, etc.) can be selected based on the procedure to be performed.

In some embodiments, the bone cement is injected into the lattice of the body 3620 to partially or completely fill chamber(s) in the body 3620 and/or intercalate with the lattice while inhibiting or substantially preventing bone cement from flowing out the top or bottom of the body 3620. In some embodiments, the lattice can have a varying density for controlling the flow of bone cement. For example, the lattice can have gradient or varying porosity to increase the density of the lattice so that the lattice is denser on the top and bottom tissue-contacting surfaces and less dense in a central region. In some embodiments, the body 3620 can include an outer low-flow lattice zone and inner high-flow lattice zone. A flow ratio characteristic of the outer low-flow lattice zone to the inner high-flow lattice zone can be equal to, less than, or greater than 0.2, 0.4, 0.5, 0.6, 0.7, 0.8, 0.9, 1, 1.5, 2, 3, 4, 5, 10, or 20. The flow characteristic can be, for example, porosity, density, or the like. For example, the flow ratio characteristic can be equal to or less than 0.5 for an outer low-flow lattice zone with a porosity of 25% and an inner low-flow lattice zone with a porosity greater than 50%. In another embodiment, the flow ratio characteristic can be equal to or greater than 2 for an outer low-flow lattice zone with a density greater than 2× the density of the inner low-flow lattice zone. In another embodiment, the flow ratio characteristic can be equal to or greater than 3 for an outer low-flow lattice zone with a density greater than 3× the density of the inner low-flow lattice zone. The size, characteristics, and number of the lattice zones can be selected based on the target flow ratio characteristics (e.g., pattern of flow paths, back pressure to generate flows, distribution of flowable material, etc.).

Referring to FIGS. 47-50, the configuration of the body 3620 can be selected based on the target corrected anatomical configuration of the patient. For example, a lumbar interbody can be different from a cervical interbody. In some embodiments, the body 3620 for anterior fusion procedures can have a tapered configuration (see FIG. 50). The body 3620 for a posterior lumbar fusion can have a non-tapered configuration. A physician can receive a kit of a plurality of different sized bodies. The physician can then select the body to be inserted based on interoperative imaging, such as fluoroscopy or X-rays. The surgeon can insert the body using instruments, such as placement rods.

FIGS. 51-55 show an anchor 3640 in accordance with an embodiment of the technology. The anchor 3640 has a generally cylindrical body 4541 that can include one or more motion inhibiting features, such as external threads, ribs (illustrated ribs 4555), openings, or the like. In the illustrated embodiment, the anchor 3640 includes an interior passageway 4590 (FIGS. 44B, 54, and 55) and through holes 4610 (one through hole identified in FIGS. 44B and 51) that can be circular, elongated, rectangular, or the like. During implantation, uncured bone cement can flow along the interior passageway 4590 and exit the anchor 3640 via the through holes 4610. The proximal elongated or oval openings can allow bone cement to flow into the interior of the implant, between the implant and the vertebral endplates, or into the vertebrae. In some embodiments, the bone cement is kept out of the disc space. A section of the anchor without any holes or openings can extend between the implant and the vertebral endplate to prevent cement from getting injected directly into the disc space immediately adjacent (e.g., above or below) the anchor. The number, position, and configuration of the through holes 4610 can be selected based on the desired delivery of the bone cement. Referring to FIGS. 51-53 and 55, the anchor 3640 can have a head 4720 configured to receive an insertion instrument, such as a torquing tool, driver instrument, or the like. In some embodiments, the head 4720 has an enlarged region or flange for seating. The configuration, features, and size of the head 4720 can be selected based on the configuration of the insertion tools.

FIGS. 56-62 show anchors in accordance with various embodiments of the technology. Example anchors can be cannulated fenestrated anchors configured to allow for cement distribution and can include slits, holes, or other flow-through features. The size of the flow-through features can vary. For example, holes could be larger proximally and smaller distally so that when a user pulls a bone cement delivery cannula proximally, the flow path of least resistance for the bone cement is via the proximal holes (e.g., proximal holes the bone cement delivery cannula moved past) rather than the distal holes through which bone cement has already been delivered. The configuration and number of anchors can be selected based on the procedure to be performed and can be used with the devices disclosed herein.

Figure 56:
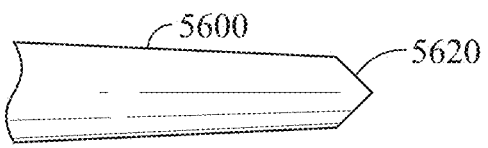
FIGS. 56-62 show anchors in accordance with various embodiments of the technology.

Referring now to FIG. 56, an anchor 5600 can have a tapered configuration with a sharp tip 5620. The tip 5620 can be pyramidal, cone shaped, tapered, or the like. In some embodiments, the anchor can have external threads.

Figure 57:
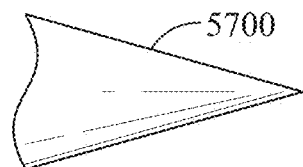

Referring now to FIG. 57, an anchor 5700 can be a tapered end spike with or without inhibiting features. The anchor 5700 can have a varying or uniform taper.

Figure 58:
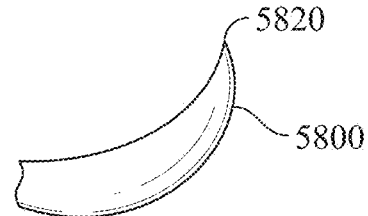

FIG. 58 shows an anchor 5800 having a curved or sickle configuration. The anchor 5800 can have a relatively sharp tip 5820 for moving through tissue. A cross-sectional shape (e.g., transverse cross-sectional shape) of the anchor 5800 can be generally circular, elliptical, or the like.

Figure 59:
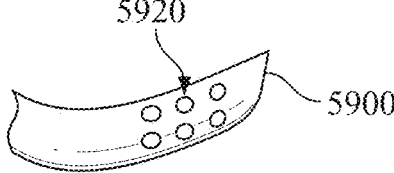

FIG. 59 shows an anchor 5900 with an array of through holes 5920. The spacing, pattern, and configuration of the through holes can be selected based on the characteristics of the material to be delivered.

Figure 60:
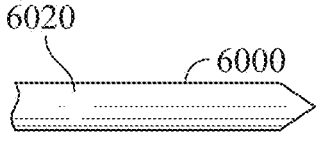

FIG. 60 shows an anchor 6000 having external threads 6020. The pitch, size, and characteristics of the threads can be selected based on the desired fixation capability.

Figure 61:
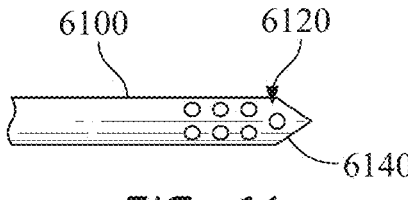

FIG. 61 shows an anchor 6100 having an array of flow-through openings 6120. External threads can extend around the body and can be adjacent to the flow-through openings. A body 6140 of the anchor can have external threads for engaging tissue.

Figure 62:

FIG. 62 is an elongated spike 6200 that has a generally arcuate shape. In some embodiments, the spike can have a wavy configuration, straight configuration, or the like.

Figure 63:
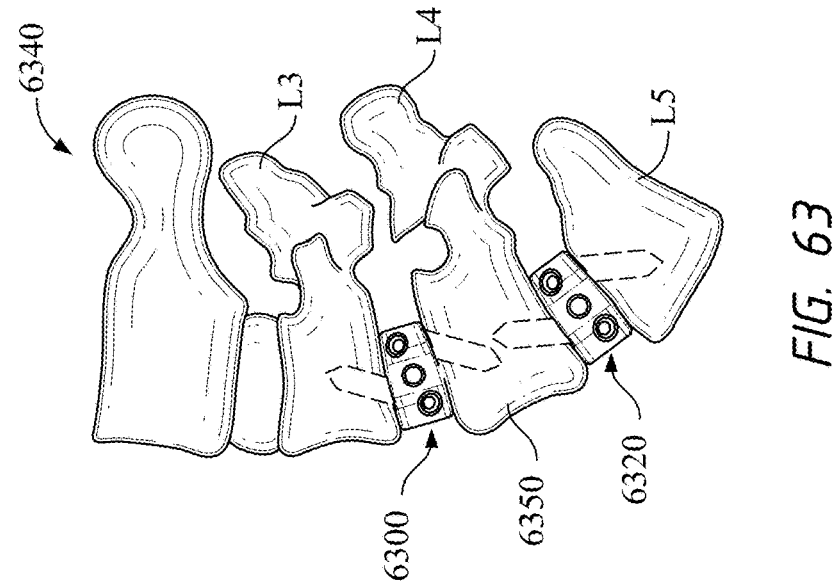
FIG. 63 is a side view of a lateral intervertebral implant assembly positioned along a subject's spine in accordance with embodiments of the technology.

FIG. 63 is a side view of intervertebral implant assemblies 6300, 6320 positioned along a subject's spine 6340 in accordance with embodiments of the technology. The description of the implant assemblies discussed in connection with FIGS. 1 to 55 applies equally to FIGS. 63-83, unless indicated otherwise. The implant assemblies 6300, 6320 are described for lateral lumbar fusion procedures discussed in connection with FIGS. 63-83. However, the configuration of the implant assemblies 6300, 6320 can be selected for different procedures, such as procedures discussed in connection with FIGS. 84-85. Accordingly, the implant assemblies 6300, 6320 can be configured for procedures as discussed in connection with FIGS. 84-85.

The implant assembly 6300 is positioned between L3 and L4 vertebrae and the implant assembly 6320 is positioned between L4 and L5 vertebrae. The number, positions, and configuration of the implant assemblies can be selected based on the targeted anatomical correction for the patient. The description of one of the implant assemblies applies equally to the other unless indicated otherwise.

Figure 64:
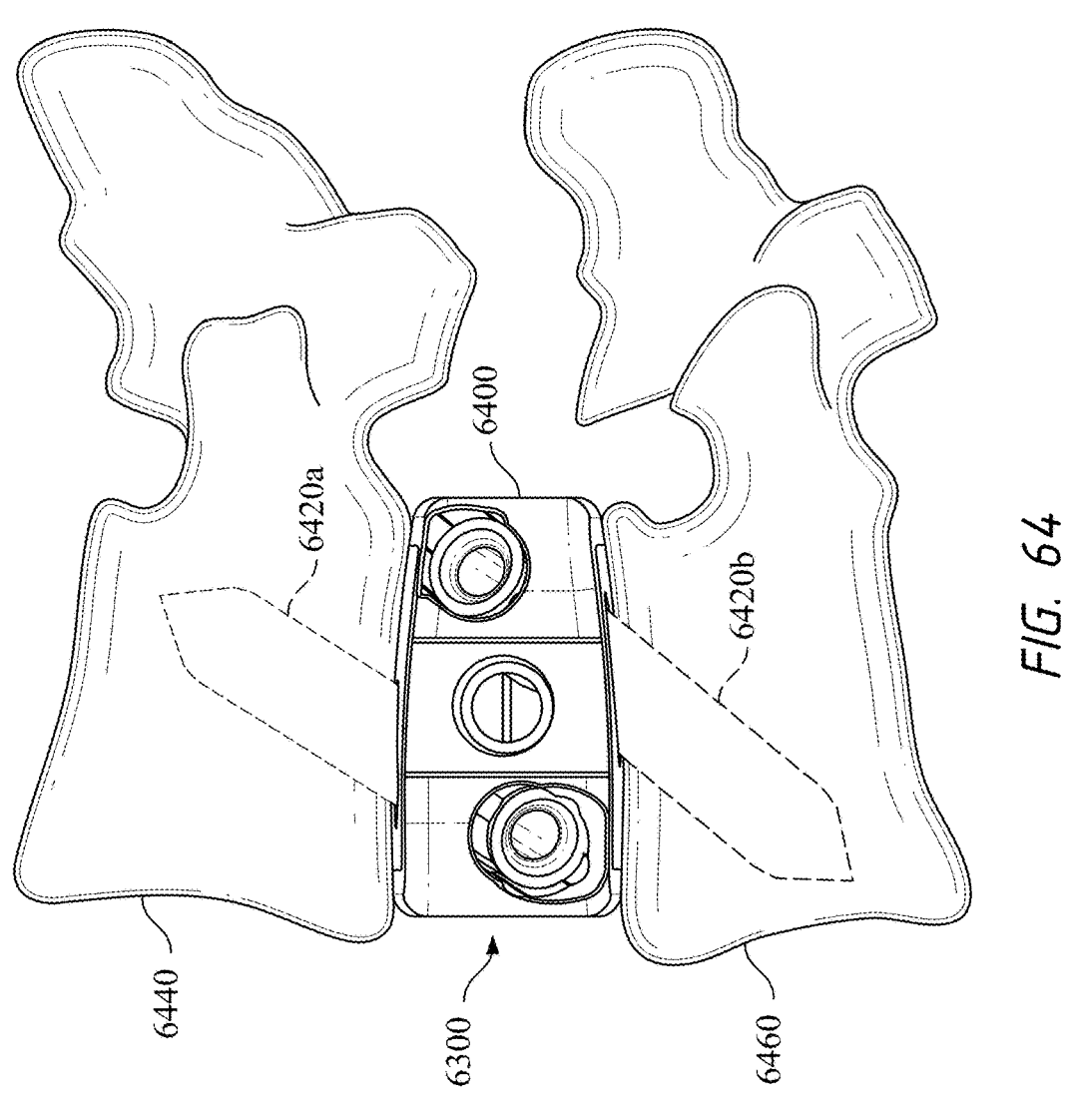
FIG. 64 is a detailed side view of the intervertebral implant assembly of FIG. 63.

FIG. 64 is a detailed side view of the lateral intervertebral implant assembly 6300 of FIG. 63. The implant assembly 6300 includes an intervertebral body 6400, a hollow upper anchor 6420a, and a hollow lower anchor 6420b. The upper anchor 6420a is configured to pierce and extend upwardly past a lower endplate 6410 of an upper vertebra 6440 when the intervertebral body 6400 contacts the lower endplate 6410. The lower anchor 6420b is configured to pierce and extend upwardly past an upper endplate 6430 of a lower vertebra 6460 when the intervertebral body 6400 contacts the upper endplate 6430. One or both anchors 6420a, 6420b and the body 6400 can define a continuous bone cement flow path along which bone cement flows for rigidly locking together components. The anchors 6420a, 6420b can include one or more openings 6421a, 6421b through which bone cement flows. The bone cement can reinforce the upper vertebra 6440 and the lower vertebra 6460.

Figure 65:
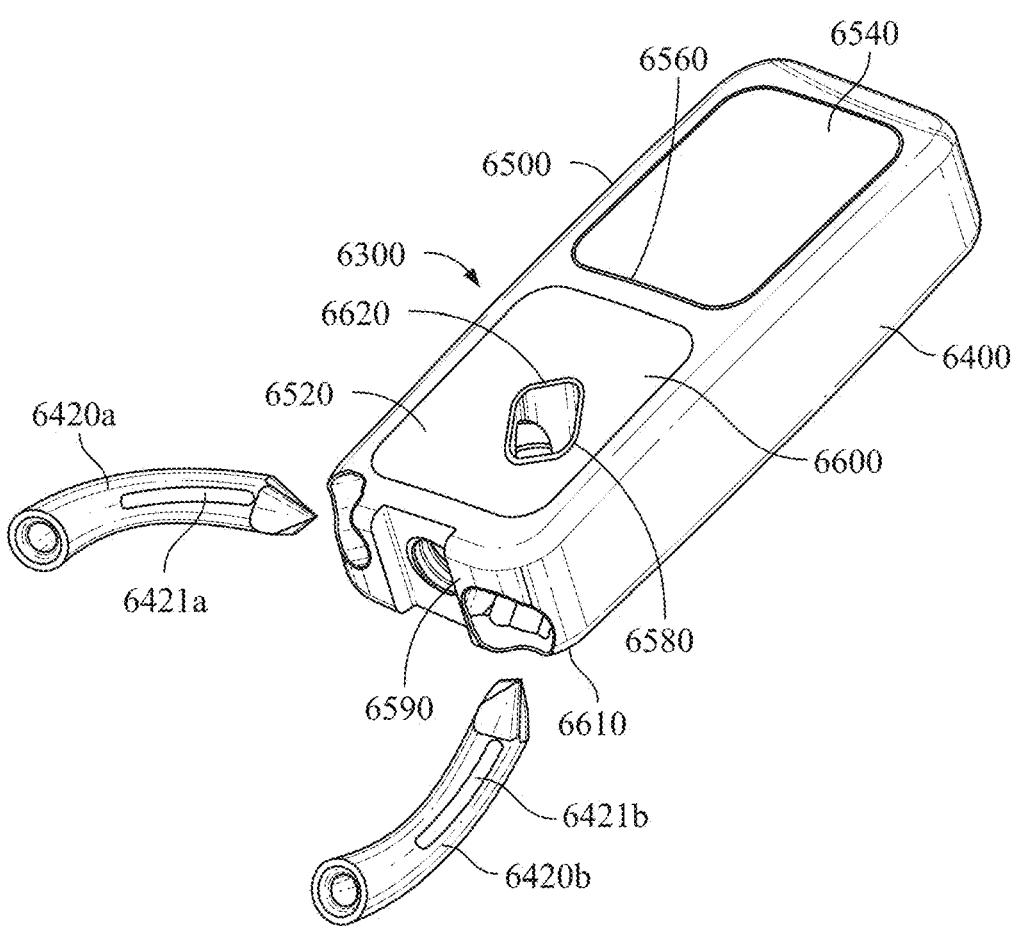
FIG. 65 is an exploded view of the intervertebral implant assembly of FIG. 63.
Figure 66:
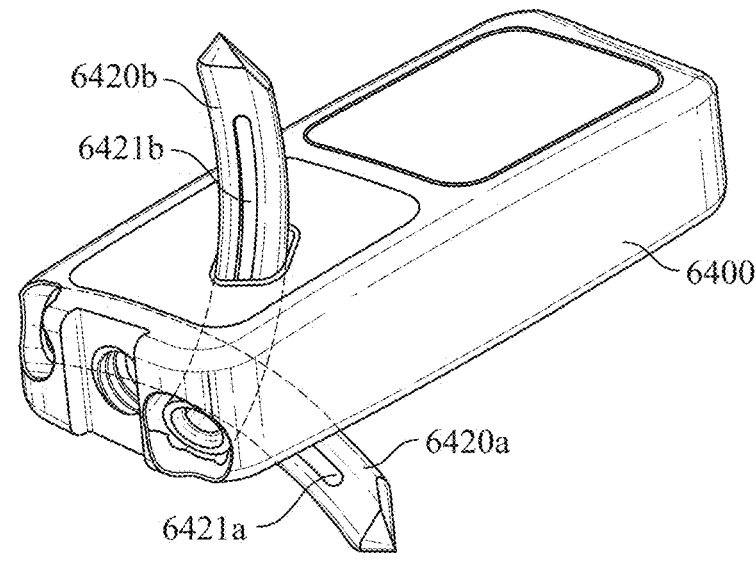
FIG. 66 is an isometric view of the intervertebral implant assembly of FIG. 63.

FIG. 65 is an exploded view of the intervertebral implant assembly 6300 of FIG. 63. FIG. 66 is an isometric view of the intervertebral implant assembly 6300. The intervertebral body 6400 can include discrete regions for receiving material. In the illustrated embodiment, the body 6400 has an outer portion 6500 configured to surround bone receiving regions or material receiving regions 6520, 6540. The region 6520 can be in the form of a bone cement flow-through porous region. The region 6540 can be a bone graft receiving region configured to hold one or more bone graft materials. The outer portion 6500 can include a partition 6560 between the regions 6520, 6540 and a solid periphery. For example, the regions 6520, 6540 can be porous lattice structures surrounded by a solid partition 6560 and outer wall.

The inner body 6400 can include anchor-receiving features 6580 (one identified) that can be, for example, arcuate or curved passageways or through holes and can extend from a side wall 6590 to a bone engagement surface 6600. The anchors 6420a, 6420b (collectively, "anchors 6420") of FIG. 65 can be moved through the anchor-receiving features during the implantation. For example, the lower anchor 6420b can be inserted into an entrance 6610 along the side wall 6590. The lower anchor 6420b can be advanced distally along the channel or passageway and out an outlet 6620, and the lower anchor 6420b can be advanced distally until it protrudes upwardly from the bone engagement surface 6600, as shown in FIG. 66. The upper anchor 6420a can be moved through the body 6400 in a similar manner. The passageways or channels can have solid structures, smooth surfaces, or other features for guiding the anchors 6420. The openings 6421a, 6421b can be partially positioned within the body 6400 to concurrently deliver bone cement into the body 6400 and the tissue. In some embodiments, the openings 6421a, 6421b are spaced apart from the body 6400 and positioned entirely within tissue, as discussed in connection with FIGS. 80 and 82. The user can select the configuration of the anchors based on the desired delivery of bone cement.

Figure 67:
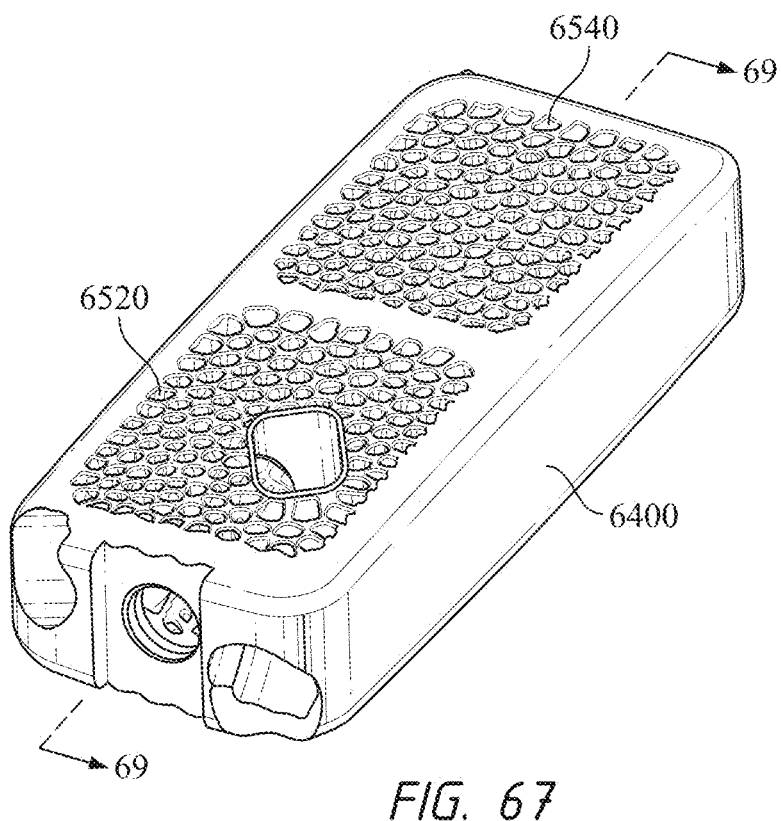
FIG. 67 is an isometric view of an intervertebral body in accordance with embodiments of the technology.

FIG. 67 is an isometric view of the intervertebral body 6400 in accordance with some embodiments. The intervertebral body 6400 can include one or more porous regions having similar or different characteristics at different regions. The region 6520 can include open or closed pores for holding bone cement. The characteristics of the bone cement can be selected based on the size, density, and characteristic of the pores. For example, pore size can be increased or decreased to accommodate high or low viscosity bone cement, respectively.

The region 6540 can be configured for receiving bone graft material. The region can have a complex, interconnected network of pores designed to allow flow of material therethrough. The pores can also promote bone growth to, for example, improve stability, mimic the structure of bone, or the like. For example, the pores can have nonuniform sizes and can be evenly or unevenly distributed to mimic the irregular structure of natural tissue. The pore size can range from, for example, about 100 micrometers to about 700 micrometers. In some embodiments, the pores can have an average diameter equal to or less than 100 micrometers, 200 micrometers, 300 micrometers, 400 micrometers, 500 micrometers, 600 micrometers, or 700 micrometers, or ranges encompassing such diameters (e.g., maximum diameter). The porosity can be a ratio of pore volume to total volume and can be selected based on the procedure. For example, high porosity (e.g., at least 80%, 90%, 95%) can be suitable for enhanced bone ingrowth. The cages can be made, in whole or in part, of one or more metals (e.g., titanium, tantalum, polyether ether ketone (PEEK), or other suitable biocompatible material). The cages can be manufactured using one or more additive manufacturing techniques (e.g., three-dimensional (3D) metal printing, selective laser manufacturing, laser melting, etc.), injection molding, or the like.

Figure 68:
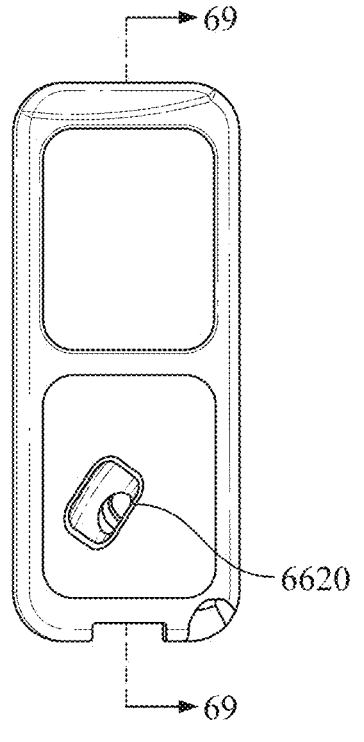
FIG. 68 is a top view of the intervertebral body of FIG. 67.

FIG. 68 is a top schematic view of the intervertebral body 6400 of FIG. 67. The position of the outlet 6620 can be selected based on the desired entrance to the vertebral body. The outlet 6620 can have a rectangular shape, circular shape, elliptical shape, or other suitable shape for closely surrounding the anchor. For example, the outlet 6620 can have a generally circular shape to receive a bone screw having a generally circular cross-sectional shape. In the illustrated embodiment, the outlet 6620 has a generally rounded rectangular shape for receiving an anchor having a generally rounded rectangular cross section.

Figure 69:
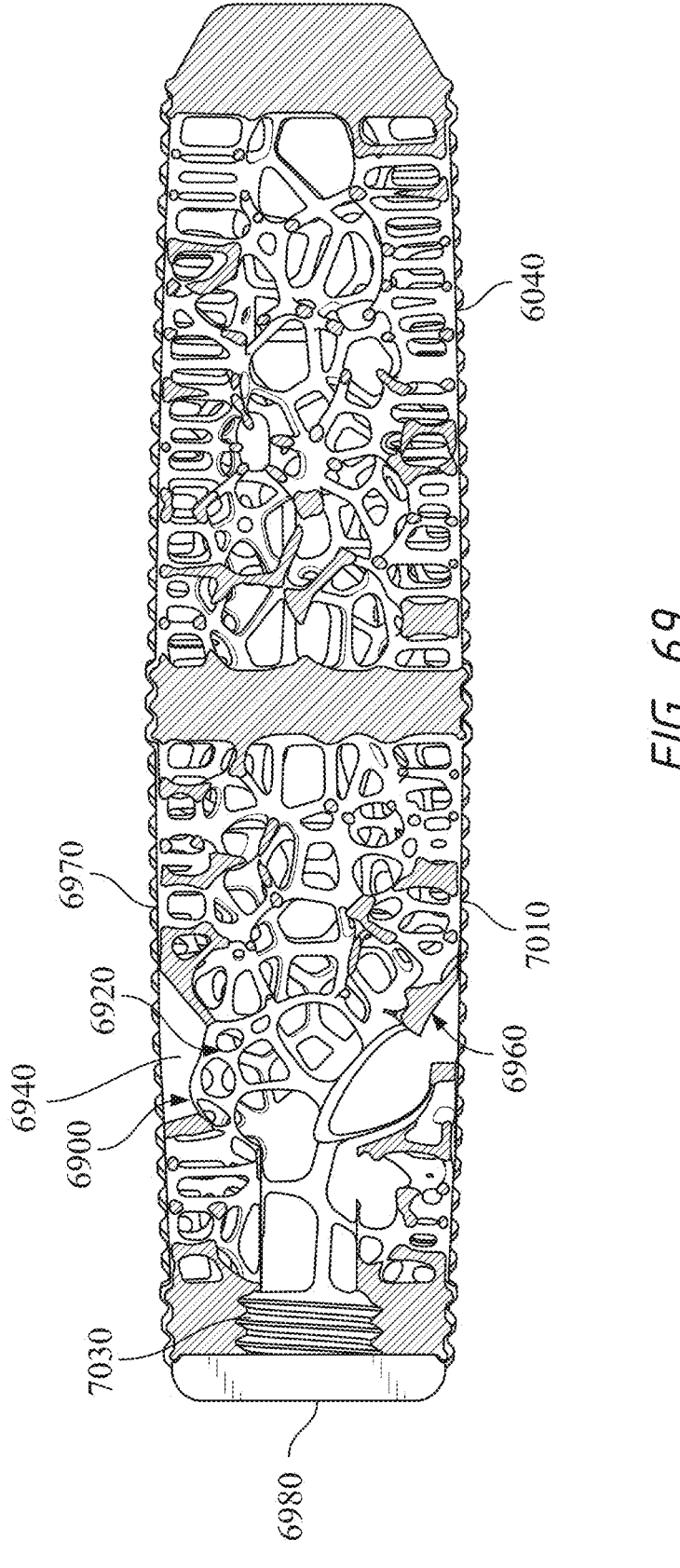
FIG. 69 is a cross-sectional view of an intervertebral body taken along line 69-69 of FIG. 68.

FIG. 69 is a cross-sectional view of the intervertebral body 6400 taken along line 69-69 of FIG. 68. The body 6400 can include a bifurcated hole 6900 that includes a central chamber 6920 and a pair of passageways 6940, 6960. In the illustrated embodiment, the passageway 6940 extends from an upper surface 6970 of the body 6400 to a side wall 6980 of the body 6400. The passageway 6960 extends from a lower surface 7010 of the body 6400 to the side wall 6980. The body 6400 can have one or more attachment features 7030 for coupling to an instrument. The attachment feature 7030 can be, for example, an internally threaded hole (illustrated), a snap fitting, a coupler fitting, or the like. The configuration and features of the body 6400 can be selected based on the procedure to be performed. For example, the body 6400 can include more than two different porous regions for selecting different materials. By way of example, the first porous region can be configured to allow bone graft material to flow therethrough. A second region can have a second porous region for holding a second bone graft material. A third porous region can have a different porosity for receiving a third bone graft material different from the second bone graft material. The characteristics (e.g., porosity, distribution of pores, geometrical characteristics of pores, patterning of pores, average size of pores, etc.) can be selected based on the materials to be retained in the body 6400.

Figure 70:
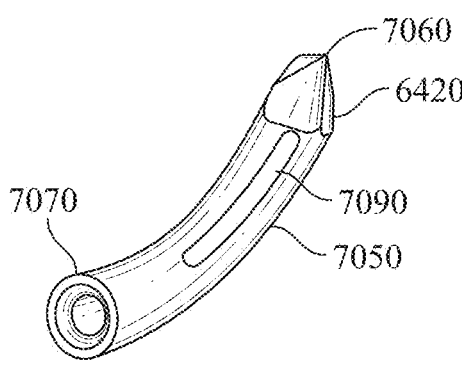
FIG. 70 is an isometric view of an anchor of the intervertebral implant assembly of FIG. 63.
Figure 71:
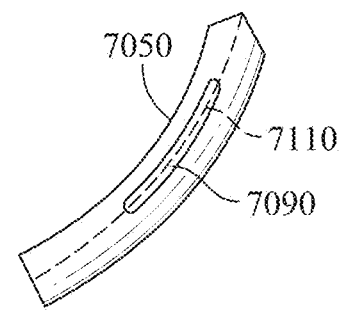
FIG. 71 is a side view of an anchor in accordance with embodiments of the technology.
Figure 72:
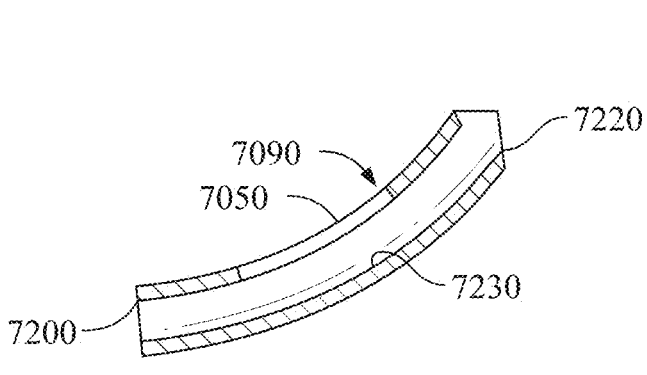
FIG. 72 is a cross-sectional view of an anchor along line 72-72 of FIG. 73.
Figure 73:
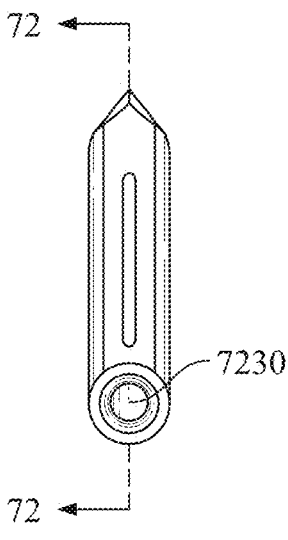
FIG. 73 is a front view of the anchor.

FIG. 70 is an isometric view of an anchor 7050 of the intervertebral implant assembly of FIG. 63. FIG. 71 is a side view of an anchor 7050 of the intervertebral implant. FIG. 72 is a cross-sectional view of the anchor 7050 taken along line 72-72 of FIG. 73. FIG. 73 is a front view of the anchor. The anchor 7050 can be a cannulated fenestrated anchor to allow for cement distribution and can include slits, holes, or other flow-through features.

Referring now to FIG. 70, the anchor 7050 can have an arcuate body having a piercing end 7060 and a head 7070. The anchor 7050 can have a removable piercing head configured to leave a hole when removed. The piercing end 7060 can have a configuration for piercing tissue. The head 7070 can have an enlarged region, a flange, a bulbous region, or the like for seating with the body. The anchor 7050 can be configured to receive and allow flowable material to move therethrough. In the illustrated embodiment, the anchor 7050 has an elongated opening 7090 configured to expel flowable bone cement. The bone cement can be delivered using a cannula, pump, or other suitable device.

Referring now to FIG. 71, the opening 7090 can extend along most of a length of the anchor 7050. The opening 7090 can extend along an arcuate path 7110 that is generally parallel to the elongated axis of the anchor 7050. Other configurations of openings can be used. The number, length, and position of the openings can be selected based on the desired location and amount of bone cement to be expelled.

Referring now to FIG. 72, the anchor 7050 can have an elongated passageway 7230 extending from an inlet 7200 to an outlet 7220. The passageway 7230 can have a smooth inner surface to allow material to flow therethrough. The opening 7090 can be a slot in the upper side of the anchor 7050. Referring now to FIGS. 72 and 73, the passageway 7230 can have a generally circular cross section (illustrated), elliptical cross section, random polygonal cross section, or other suitable cross section for receiving flowable material. The anchors discussed in connection with FIGS. 1-68 can include the features discussed in connection with FIGS. 70-73. For example, the anchors discussed in connection with FIGS. 56-62 can include one or more elongated slots, similar to the elongated opening 7090 of FIGS. 71-73. Additionally, the anchor 7050 can include features discussed in connection with FIGS. 56-62. For example, the anchor 7050 of FIG. 70 can include both elongated slots and sets of through holes, such as through holes 5920 at FIG. 59.

Figure 74:
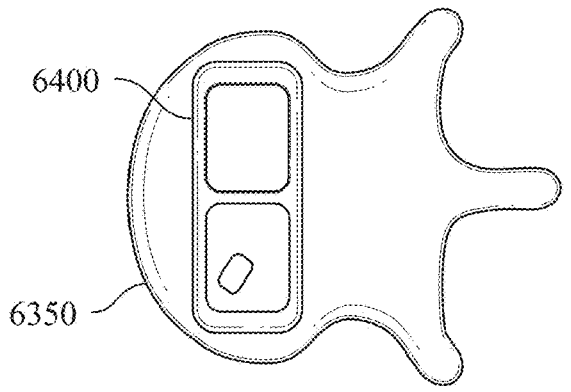
FIGS. 74-76 illustrate steps for implanting an intervertebral implant assembly along a subject's spine in accordance with embodiments of the technology.
Figure 75:
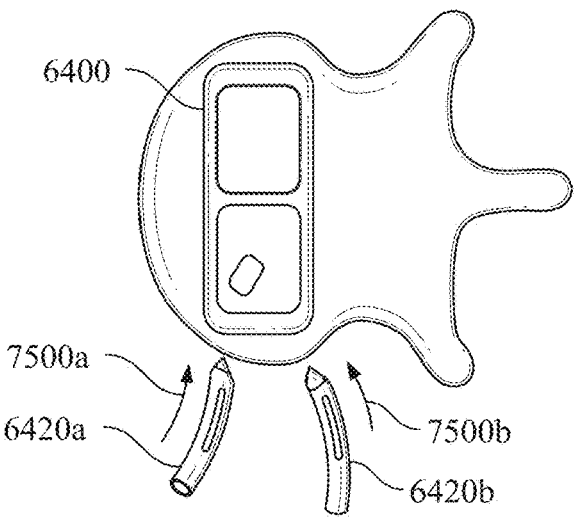
Figure 76:
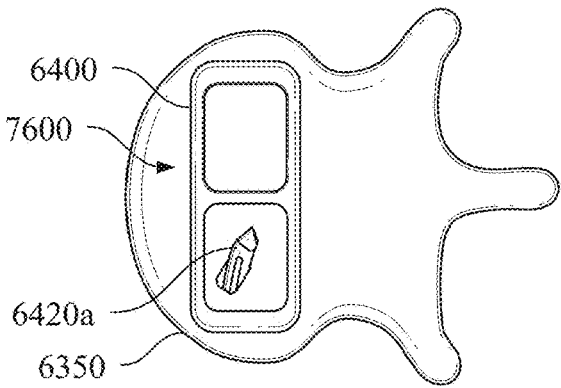

FIGS. 74-76 illustrate steps for implanting an intervertebral implant along a subject's spine in accordance with embodiments of the technology. The intervertebral body 6400 can be inserted into the patient using a lateral approach to position the body on a vertebral endplate 7600 of the vertebra 6350. The position of the intervertebral body 6400 can be confirmed using one or more imaging techniques, such as thoracoscopy, X-ray imaging, or the like. A physician can move the anchors and deliver the anchors through the body 6400 as indicated by arrows 7500. The anchors 6420a, 6420b can be advanced distally into the patient, as indicated by arrows 7500a, 7500b. FIG. 76 shows the implant assembly after inserting the anchors 6420. Although not visible, the lower anchor 6420b extends through the body 6400 into the endplate 7600 of the vertebra 6350. The upper anchor 6420a extends into an upper vertebra, as illustrated in FIG. 63.

Figure 77:
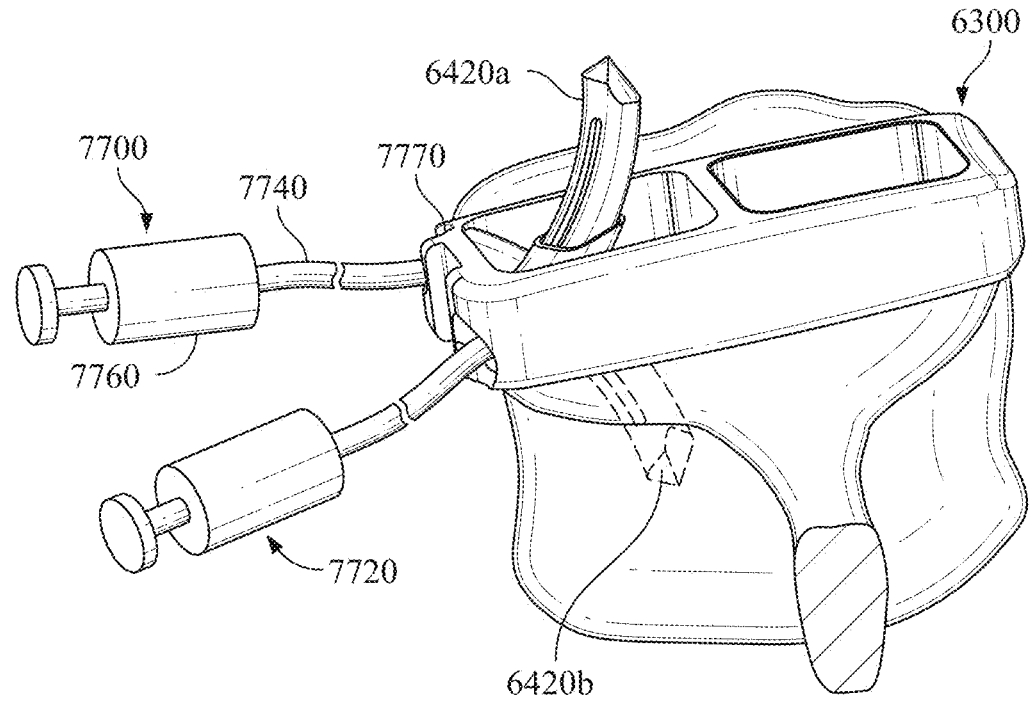
FIG. 77 shows material delivery devices positioned for insertion into the intervertebral implant assembly in accordance with embodiments of the technology.

FIG. 77 shows material delivery devices positioned for insertion into the intervertebral implant assembly 6300. A pair of delivery devices 7700, 7720 are positioned for insertion into the intervertebral implant assembly 6300 for delivering bone graft material. The delivery device 7700 includes a cannula 7740 and a pump 7760. The distal tip 7770 in the canula 7740 can be inserted into and through the lower anchor 6420b. The delivery device 7720 can be inserted and advanced distally along the interior passageway of the upper anchor 6420a. For example, the distal portions of the cannula 7740 are configured to be moved through a passageway of at least one of the hollow upper or lower anchors 6420a, 6420b. The delivery devices 7700, 7200 can be configured to expel the bone cement while being moved distally through the implant assembly 6300. In some embodiments, the cannula 7740 is sufficiently rigid to help push the material distally through and/or out of the implant assembly 6300.

Figure 78:
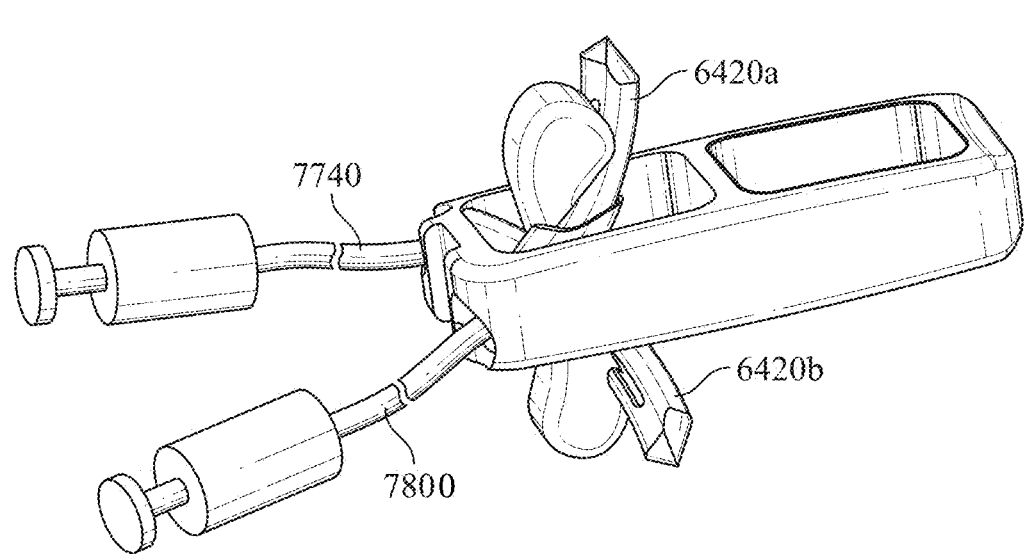
FIG. 78 shows material flowing out of the intervertebral implant assembly in accordance with embodiments of the technology.

FIG. 78 shows the cannula 7740 positioned in the lower anchor 6420b, a cannula 7800 of the delivery device 7720 positioned in the upper anchor 6420a, and bone graft material flowing out of the elongated slots of the anchors 7420.

Figure 79:
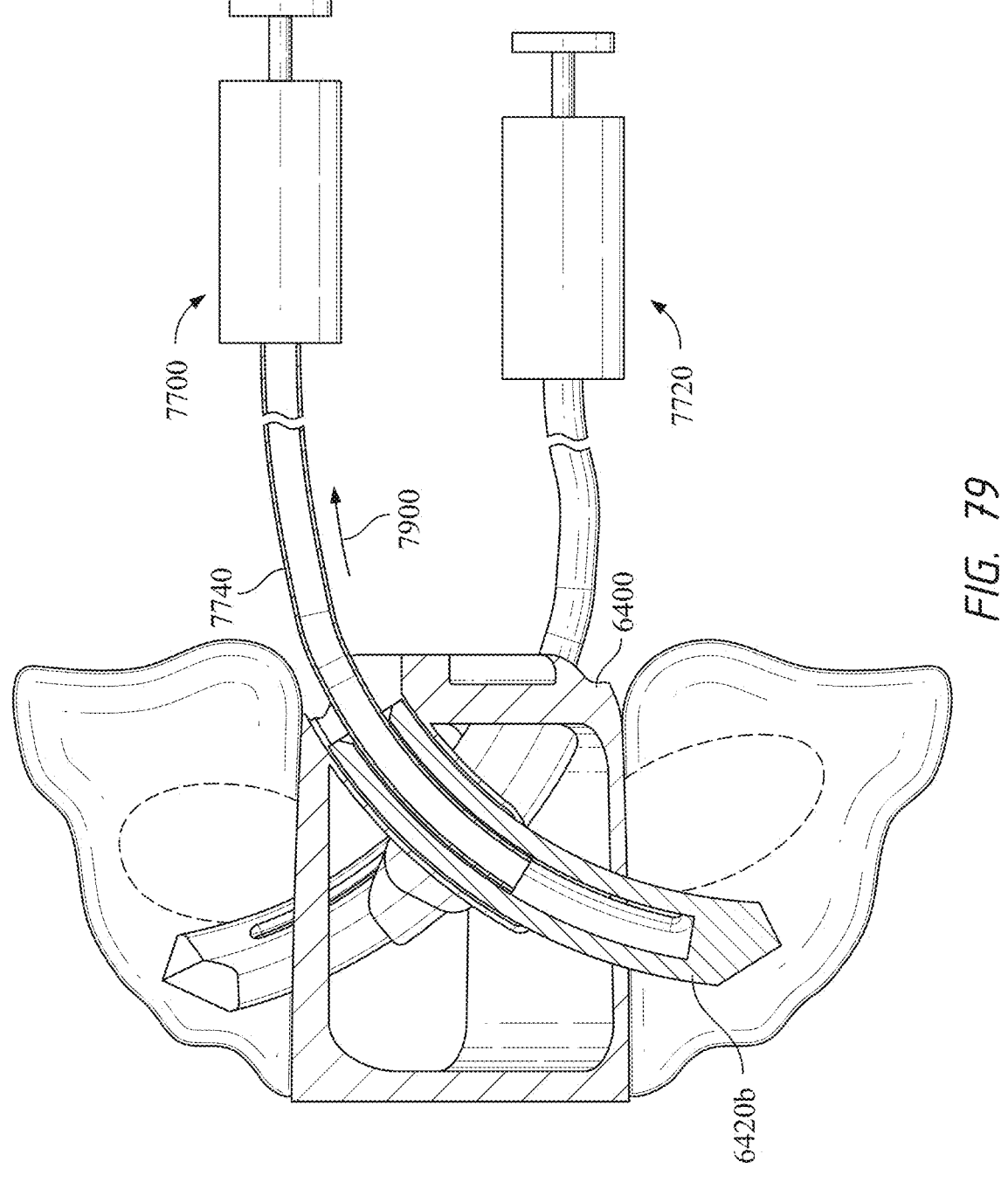
FIG. 79 is a side view of the intervertebral implant assembly and the material delivery devices delivering material into vertebral bodies.

FIG. 79 is a cross-sectional view of the vertebrae with the bone graft material being delivered. Referring to FIGS. 78 and 79, distal ends of the cannulas can be moved in a superior/inferior direction to position the distal ends inside of the vertebrae. During delivery of the bone graft material, the cannula can be continuously or intermittently withdrawn (e.g., pulled proximally), advanced distally, etc. For example, the cannula 7740 of FIG. 79 can be gradually pulled distally, as indicated by arrows 7900, while delivering bone stem material at a constant or variable rate. This allows the bone graft material to fill the inside of the lower anchor 6420b and interior chambers or holding space of the body 6400. This bone cement delivery process can be used with the other implanted members disclosed herein.

The delivery devices 7700, 7720 can be configured to hold and dispense therapeutically effective amounts of the bone cement or other injectable compound to therapeutically reinforce the at least one of the upper vertebra or the lower vertebra. A user can dispense a therapeutically effective amount of the bone cement. A user can determine whether the therapeutically effective amount of bone cement has been delivered based on, for example, the total dispensed volume of material, imaging (e.g., material has been delivered into anatomy confirmed via fluoroscopy or X-rays), or the like.

Figure 80:
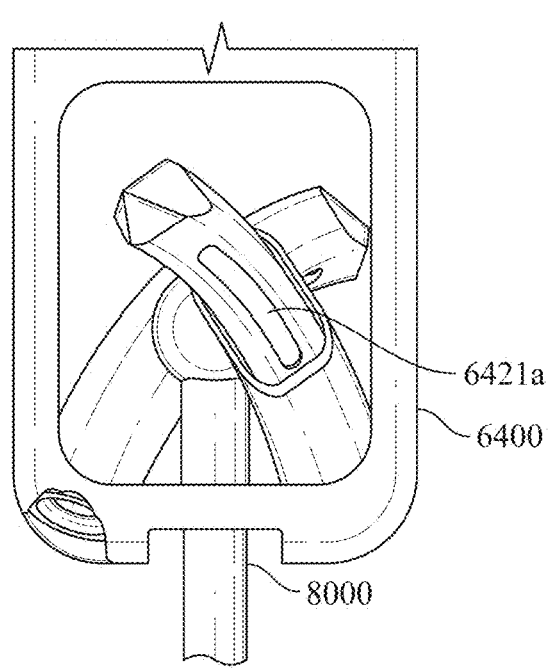
FIG. 80 is a top view of a proximal end of an intervertebral implant assembly and a portion of a material delivery device.

FIG. 80 is a top view showing the anchors extending transversely within the vertebral bodies to help lock the implanted intervertebral body 6400 to the vertebrae. The anchors have elongated openings for outputting material along most of the imbedded portions of the anchors. The intervertebral body 6400 and anchors 6420 can be sequentially or concurrently filled with material. In some procedures, the body 6400 can be independently filled with material. For example, one of the cannulas or another cannula can be inserted into an opening 8000 of the body 6400 filling a central chamber (chamber 6920 at FIG. 69) or other spaces within the body 6400. This can allow cement material to substantially fill the entire proximal region of the body 6400. For example, the bone cement can fill substantially all of the empty space within the proximal regions of the body 6400. In some embodiments, the openings (e.g., opening 6421a shown in FIGS. 80 and 82) are spaced apart from the body 6400 and positioned entirely within tissue.

During a surgical procedure, the cannulas can be repeatedly inserted into the implant assembly to deliver flowable material at different locations along the intervertebral body. That flowable material can flow out of the intervertebral body and/or anchors and into adjacent tissue. Different material delivery protocols can be used based on the procedure. For example, in some embodiments, the interior chamber can initially receive material. Then material can be delivered into and through the anchors. In other embodiments, the anchors are filled with bone graft material and then the interior chamber is subsequently filled with material. In some embodiments, anchors 6420 can have one or more proximal holes, which, when seated, can align with corresponding holes in the anchor guide tube of the spacer or interbody member in order to allow injection into the body 6400 via the anchor 6420.

Figure 81:
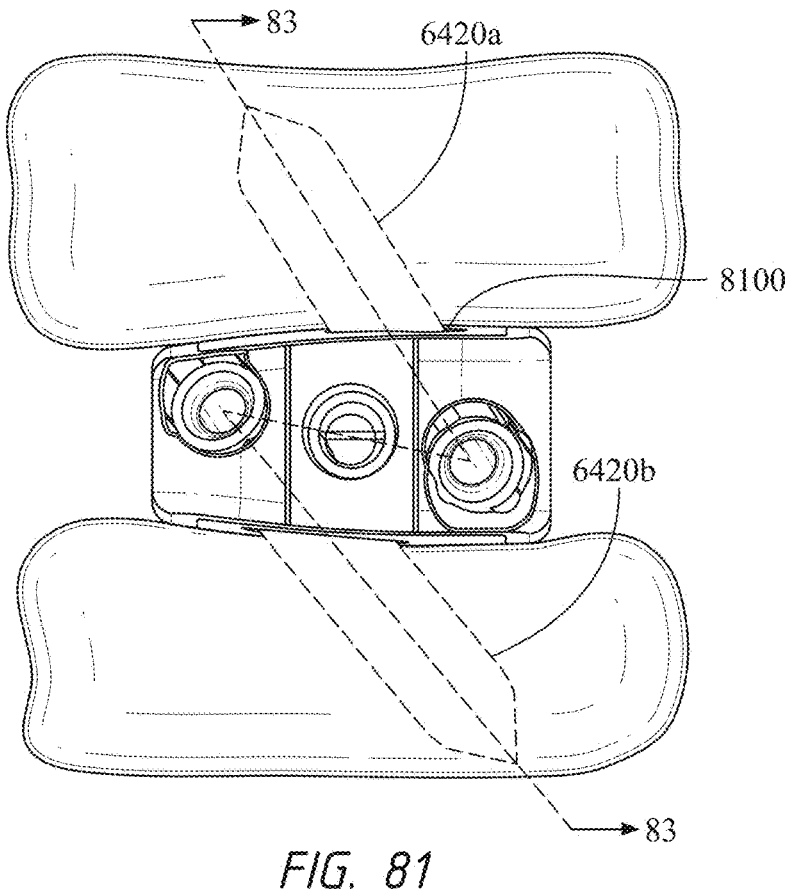
FIG. 81 is a front view of the intervertebral implant assembly positioned between vertebral bodies in accordance with embodiments of the technology.

FIG. 81 is a front view of the intervertebral implant positioned between vertebral bodies in accordance with embodiments of the technology. The location and configuration of the anchors 6420a, 6420b can be selected based on the anatomy. FIG. 81 shows the anchors 6420a, 6420b configured to be generally parallel to one another and to extend angularly into vertebral bodies. For example, a longitudinal axis can be generally parallel (as viewed from front) to a longitudinal axis of a lower anchor 6420*b*. In at least one embodiment, there are no anchor holes that are open to the space between the spacer and the bone to inhibit or prevent material from flowing into the intervertebral space.

Figure 82:
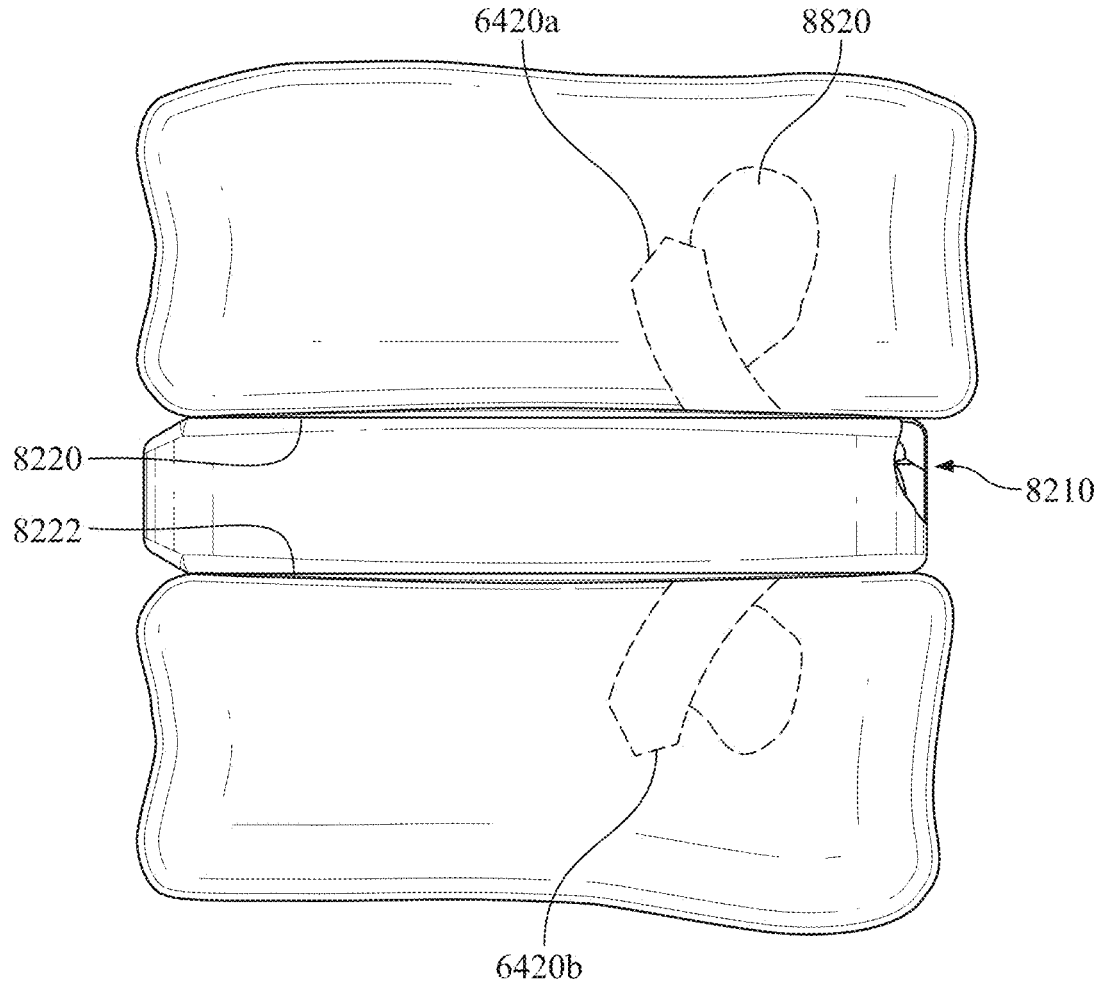
FIG. 82 is a side view of the intervertebral implant assembly positioned between vertebral bodies in accordance with embodiments of the technology.
Figure 83:
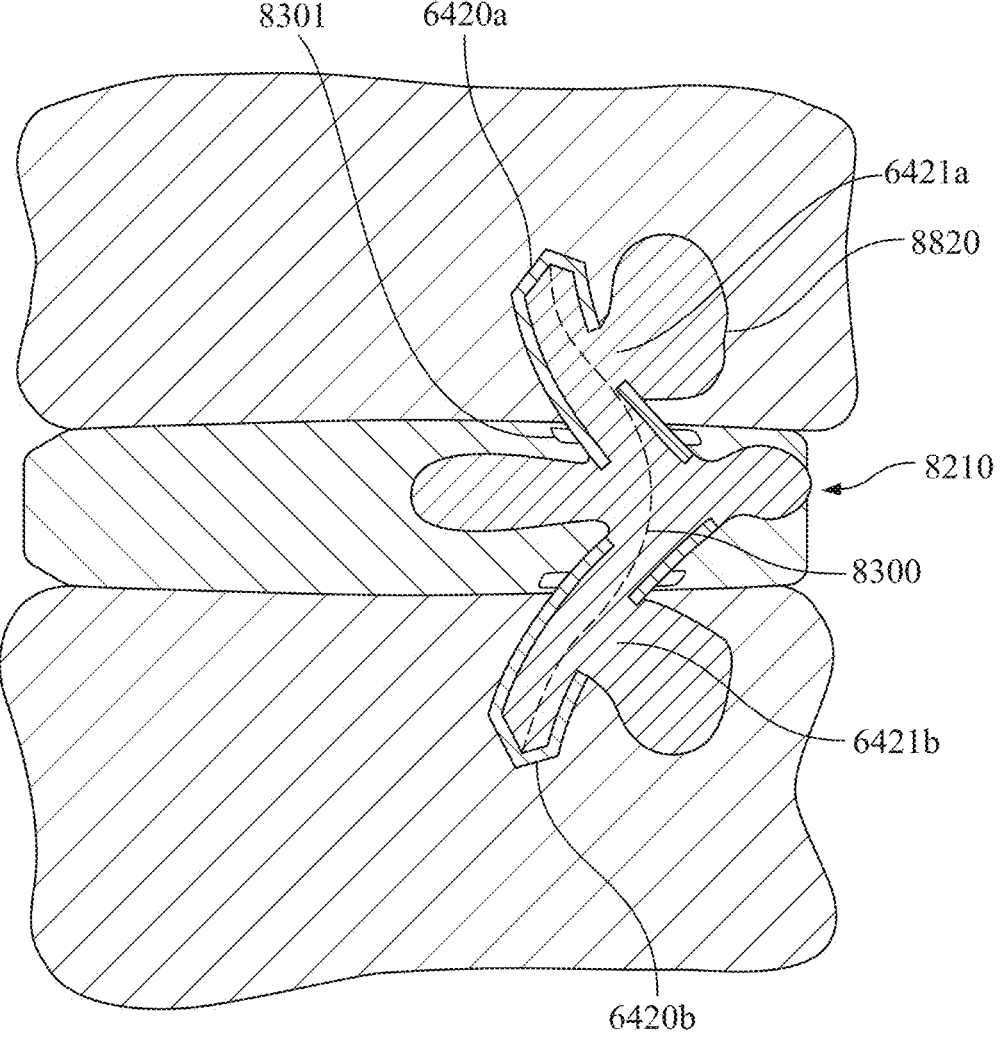
FIG. 83 is a side view of the intervertebral implant assembly positioned between vertebral bodies taken along section line 83-83 of FIG. 81.

FIG. 82 is a side view of the intervertebral implant positioned between vertebral bodies in accordance with embodiments of the technology. The delivered cement 8820 can be spaced apart from intervertebral space 8210, endplate surfaces 8220, 8222, etc. After implantation, the delivered cement 8820 can gradually harden over a period of time, thereby forming a generally continuous cement structure that extends both into adjacent vertebrae and through the implant assembly. In some embodiments, there is a separate hole/slit on the opposite side of the upper anchor 6420*a* that communicates into the spacer. FIG. 83 shows the cement extending along a generally continuous path 8330 between opposing ends of the anchors 6420*a*, 6420*b*. The amount of dispensed cement can be selected based on the procedure being performed, condition of the spine, health of the vertebrae, etc.

Figures 84, 85:
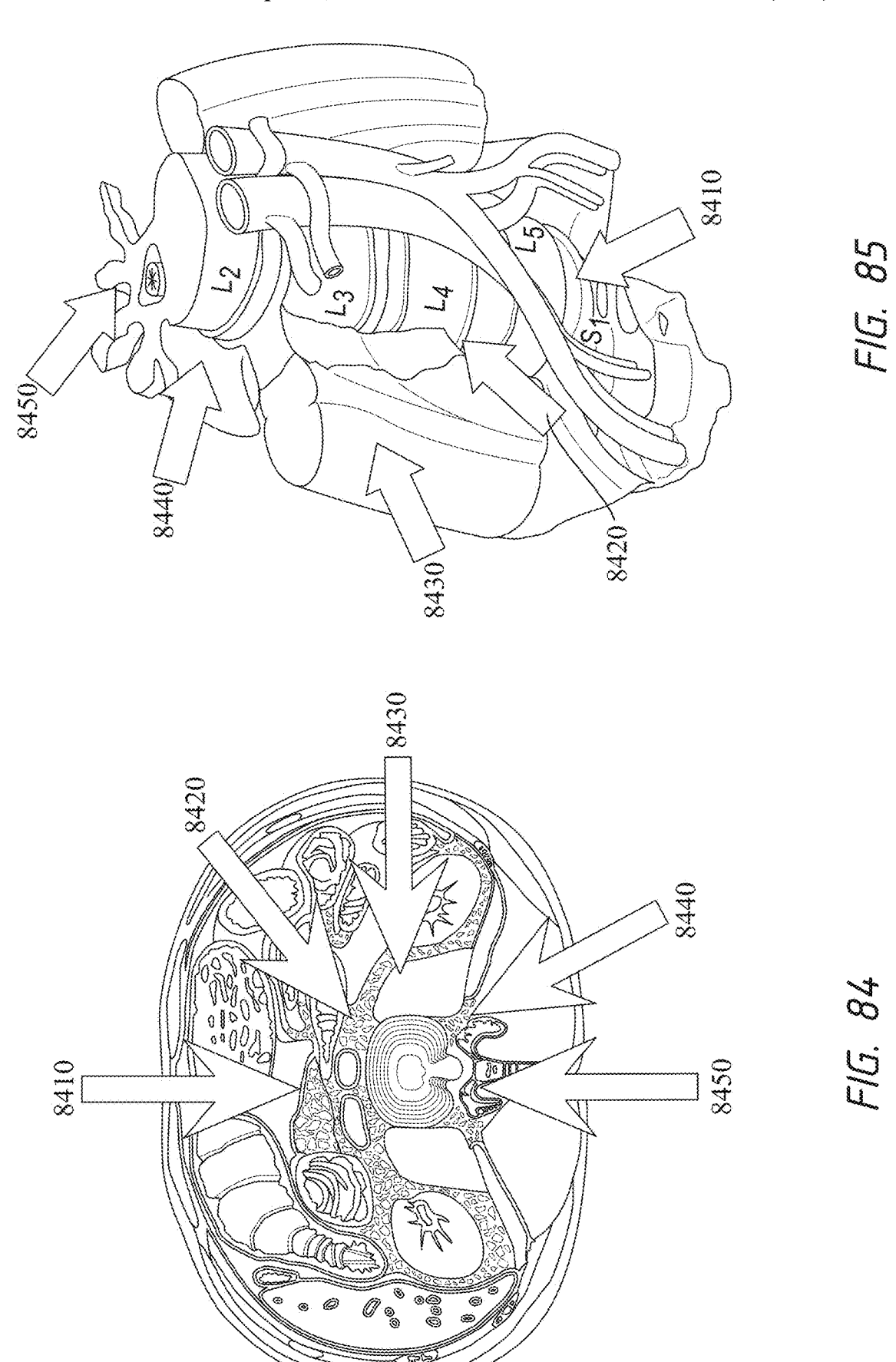
FIG. 84 is a schematic top plan view of a human subject and illustrates example approaches for performing interbody fusion procedures.
FIG. 85 is an isometric view of a lumbar spine of the subject and illustrates example approaches of FIG. 84.

FIG. 83 is a schematic cross-sectional side view of the intervertebral implant positioned between vertebral bodies taken along line 83-83 of FIG. 81. FIG. 84 is a schematic top plan view along a human subject and illustrates example approaches for performing procedures suitable for implants. FIG. 85 is an isometric view of the lumbar spine and illustrates example approaches of FIG. 84. Referring now to FIG. 83, the openings 6421*a*, 6421*b* can be spaced apart from the intervertebral body 6400. The anchors 6420*a*, 6420*b* have opposing openings 8321*a*, 8321*b*, respectively, located inside the body 6400 for delivering cement inside the body 6400. The anchors 6420*a*, 6420*b* can sealingly contact the body 6400 to reduce, limit, or substantially prevent material from flowing into the intervertebral space. For example, the body 6400 and/or anchors 6420*a*, 6420*b* can include one or more integral or separate sealing members (e.g., non-porous annular region, sealing members, O-rings, metal gaskets, etc.) for forming a fluid tight seal, liquid tight seal, or other seal. For example, the sealing members 8301 can form a liquid tight seal with the surface of the anchors 6420*a*, 6420*b*. In some embodiments, the exteriors of the anchors 6420*a*, 6420*b* slidably contact the body 6400 such that flowable material is prevented from flowing across the anchor-body interface. In other embodiments, a gap between the anchors 6420*a*, 6420*b* allows material (e.g., bone graft material) to be delivered into the intervertebral space. In some embodiments, the anchors 6420*a*, 6420*b* have multiple passageways and openings to deliver different materials to different locations.

Referring to FIGS. 84-85, surgical instruments can be delivered via different paths, including an anterior lumbar interbody fusion (ALIF) path 8410, an oblique lumbar interbody fusion (OLIF) path 8420, a lateral or extreme lateral lumbar interbody fusion (LLIF or XLIF) path 8430, a transforaminal lumbar interbody fusion (TLIF) path 8440, and a posterior lumbar interbody fusion (PLIF) path 8450. Intervertebral devices can be adapted to fit a geometry suitable for delivery via delivery paths, for example, ALIF, OLIF, LLIF or XLIF, TLIF, and PLIF paths. For example, the intervertebral devices (e.g., cages, members, assemblies, etc.) discussed in connection with FIGS. 1-83 can be configured for ALIF, OLIF, LLIF or XLIF, TLIF, and PLIF procedures along different sections of the spine, including lumbar spine, cervical spine, etc.

Referring to FIG. 85, surgical instruments can be delivered via different paths, including an ALIF path 8410, an OLIF path 8420, a LLIF or XLIF path 8430, a TLIF path 8440, and a PLIF path 8450. The intervertebral members can be adapted to fit a geometry suitable for delivery via the different paths, for example, ALIF, OLIF, LLIF or XLIF, TLIF, and PLIF. An example LLIF procedure is discussed in connection with FIGS. 74-76. The spinal systems disclosed herein can be configured for single-level or multilevel procedures.

Similar paths can be used to deliver implants to different levels (e.g., cervical level) or regions. For example, an anterior implant assembly (e.g., implant assembly 3600) can be delivered along a path parallel to ALIF path 8410 for implantation at the cervical spine, lumbar spine, or the like. In some procedures, implants can be implanted at different levels using different delivery paths. The configuration of the implant can be selected based on the implantation techniques, implantation site, etc. For example, the implant assembly 3600 (FIGS. 36-38) can be configured to hold an amount of bone reinforcement composition selected based on the amount of bone reinforcement composition delivered into vertebrae. In some embodiments, the implant assembly can be configured to hold at least 20%, 30%, 40%, 50%, 60%, 70%, 80%, 90%, 100%, 110% (by weight or volume) of the bone reinforcement composition delivered into vertebrae, hold by the cannula system, etc.

Examples

The present technology is illustrated, for example, according to various aspects described below. Various examples of aspects of the present technology are described as numbered examples (1, 2, 3, etc.) for convenience. These are provided as examples and do not limit the present technology. It is noted that any of the dependent examples can be combined in any suitable manner, and placed into a respective independent example. The other examples can be presented in a similar manner.

1. A spinal implant system, comprising:
an implant assembly configured to deliver bone cement into an upper vertebra of a subject and a lower vertebra of the subject, the implant assembly including an intervertebral body, and
a hollow upper anchor and a hollow lower anchor configured to be received by the intervertebral body to define a continuous bone cement flow path along which the bone cement flows for rigidly locking the spinal implant system together after the hollow upper anchor is positioned in the upper vertebra and the hollow lower anchor is positioned in the lower vertebra.

2. The spinal implant system of example 1, wherein
the intervertebral body includes a bifurcated fixation hole;
the intervertebral body is configured to be positioned between the upper and lower vertebrae and includes a side wall, wherein the bifurcated fixation hole extends from the side wall and includes an upper opening and a lower opening;
the hollow upper anchor is configured to be received by the upper opening such that the hollow upper anchor extends into the upper vertebra; and
the hollow lower anchor is configured to be received by the lower opening such that the hollow lower anchor extends into the lower vertebra;
the intervertebral body and the hollow upper and lower anchors define the continuous bone cement flow path such that bone cement flows out of the hollow upper anchor into the upper vertebra, flows out of the hollow lower anchor into the lower vertebra, and forms a continuous cement structure extending through the hollow upper anchor, a portion of the intervertebral body between the hollow upper and lower anchors, and the hollow lower anchor.

3. The spinal implant system of example 1 or example 2, wherein the bone cement flow path extends along an upper passageway of the upper anchor, through a central chamber of the intervertebral body, and along a lower passageway of the lower anchor.

4. The spinal implant system of any one of examples 1-3, wherein at least one of the hollow upper anchor or the hollow lower anchor includes an outlet through which the bone cement exits the spinal implant.

5. The spinal implant system of any one of examples 1-4, wherein the hollow upper anchor is configured to extend upwardly past a lower endplate of the upper vertebra when the intervertebral body contacts the lower endplate; and the hollow lower anchor is configured to extend downwardly past an upper endplate of the lower vertebra when the intervertebral body contacts the lower endplate.

6. The spinal implant system of any one of examples 1-5, wherein the hollow upper and lower anchors have longitudinal axes generally parallel to a parasagittal plane of the intervertebral body.

7. The spinal implant system of any one of examples 1-6, wherein one or both of the hollow upper and lower anchors includes through-holes through which the bone cement is capable of flowing to exit the spinal implant system.

8. The spinal implant system of any one of examples 1-7, wherein the hollow upper anchor is a first upper anchor, and the hollow lower anchor is a first lower anchor, the implant system further including:

a second upper anchor configured to extend into the upper vertebra; and a second lower anchor configured to extend into the lower vertebra, wherein a continuous flow passageway extends through the first and second upper anchor, through the first and second lower anchors, and through a portion of an anchor-receiving bifurcated fixation hole of the intervertebral body, thereby rigidly locking the spinal implant system together after implantation in the subject.

9. The spinal implant system of any one of examples 1-8, wherein the intervertebral body is an intervertebral cage including a bone-cement flow-through porous region; and a bone graft receiving region that is configured to hold bone graft material while the bone cement flows through the bone-cement flow-through porous region.

10. The spinal implant system of any one of examples 1-9, further comprising:

a delivery device including a pump and a delivery cannula fluidically connected to the pump, wherein the pump is operable to drive the bone cement through and out of the delivery cannula positioned in the implant assembly.

11. The spinal implant system of example 10, wherein the delivery device is configured to hold and dispense a therapeutically effective amount of the bone cement to therapeutically reinforce the at least one of the upper vertebra or the lower vertebra.

12. The spinal implant system of example 10 or example 11, wherein a distal portion of the delivery cannula is configured to be moved through a passageway of at least one of the hollow upper or lower anchors.

13. The spinal implant system of any one of examples 10-12, wherein the delivery device is configured to expel the bone cement while being moved proximally along the continuous bone cement flow path.

14. The spinal implant system of any one of examples 10-13, wherein the pump is syringe pump configured to dispense a volume of the bone cement from the delivery cannula while withdrawing the delivery cannula to gradually fill the spinal implant system with the volume of bone cement.

15. The spinal implant system of any one of examples 10-14, wherein a distal end of the delivery cannula is configured to be moved in a superior/inferior direction through the spinal implant system to position the distal end inside at least one of the upper vertebra or the lower vertebra.

16. The spinal implant system of any one of examples 1-15, wherein the intervertebral body includes bifurcated fixation hole, an upper opening for facing the upper vertebra, and a lower opening for facing a lower vertebra, wherein the bifurcated fixation hole includes an angled passageway having a generally V-shaped configuration for connecting the upper opening to the lower opening through a central chamber of the intervertebral body.

17. The spinal implant system of any one of examples 1-16, wherein the hollow upper anchor and the hollow lower anchor each include a curved segment configured to follow an arcuate path when inserted into the respective upper vertebra and lower vertebra.

18. The spinal implant system of any one of examples 1-17, wherein the hollow upper anchor and the hollow lower anchor are positioned on opposite sides of a parasagittal plane of the intervertebral body and are vertically aligned to facilitate material flow between their respective hollow passageways.

19. The spinal implant system of any one of examples 1-18, wherein the intervertebral body includes a partition wall extending through a central chamber to separate a bone-cement flow-through porous region from a bone graft receiving region within the intervertebral body.

20. The spinal implant system of any one of examples 1-19, wherein the hollow upper anchor and the hollow lower anchor each include motion inhibiting features including at least one of external threads, ribs, or surface texturing configured to engage with bone tissue and resist anchor migration.

21. The spinal implant system of any one of examples 1-20, wherein the intervertebral body has a first porous region with a first average porosity and a second porous region with a second average porosity different from the first average porosity.

22. The spinal implant system of example 21, wherein a ratio of the first average porosity to the second average porosity is greater than 2.

23. The spinal implant system of example 21 or example 22, wherein the first porous region is an outer region and the second porous region is inside region, and wherein the first average porosity is substantially less than the second average porosity.

24. The spinal implant system of any one of examples 1-23, further comprising:

a delivery device including a pump and a delivery cannula fluidically connected to the pump, wherein the pump is operable to cause the delivery device to eject cement through a hole in the delivery cannula, wherein the delivery cannula is rotatable within a passageway of one of the hollow upper anchor or the hollow lower anchor to direct cement through a specific hole in the one of the anchors.

25. A spinal implant system, comprising:

an implant assembly configured to deliver bone cement into an upper vertebra of a subject and a lower vertebra of the subject, the implant assembly including an intervertebral body including interconnected passageways extending from an upper opening facing the upper vertebra and a lower opening facing the lower vertebra, the interconnected passageways defining a continuous bone cement flow path along which bone cement flows between the upper and lower openings and through the intervertebral body.

26. The spinal implant system of example 25, wherein the interconnected passageways include a bifurcated fixation hole configure to receive a plurality of bone anchors.

27. The spinal implant system of example 25 or example 26, wherein the interconnected passageways includes an upper passageway extending from the upper opening to a sidewall face of the intervertebral body, and a lower passageway extending from the lower opening to the sidewall face of the intervertebral body.

28. The spinal implant system of example 27, wherein at least one of the upper passageway or the lower passageway is curved passageway configured to guide a cannula into a vertebral body.

29. The spinal implant system of example 27 or example 28, wherein at least one of the upper passageway or the lower passageway is configured to receive a delivery cannula configured to deliver the bone cement.

30. The spinal implant system of any one of examples 27-29, wherein the intervertebral body includes a laterally extending passageway connecting the upper passageway and the lower passageway.

31. The spinal implant system of any one of examples 25-30, further comprising a hollow upper anchor and a hollow lower anchor, wherein the interconnected passageways include a bifurcated fixation hole configured to receive the hollow upper anchor and hollow lower anchor.

32. The spinal implant system of example 31, wherein the intervertebral body is configured to be positioned between the upper and lower vertebrae and includes a side wall, wherein the bifurcated fixation hole extends from the side wall and includes an upper opening and a lower opening;

the hollow upper anchor is configured to be received by the upper opening such that the hollow upper anchor extends into the upper vertebra; and the hollow lower anchor is configured to be received by the lower opening such that the hollow lower anchor extends into the lower vertebra;

the intervertebral body and the hollow upper and lower anchors define the continuous bone cement flow path such that bone cement flows out of the hollow upper anchor into the upper vertebra, flows out of the hollow lower anchor into the lower vertebra, and forms a continuous cement structure extending through the hollow upper anchor, a portion of the intervertebral body between the hollow upper and lower anchors, and the hollow lower anchor.

33. The spinal implant system of example 31 or example 32, wherein the bone cement flow path extends along an upper passageway of the upper anchor, through a central chamber of the intervertebral body, and along a lower passageway of the lower anchor.

34. The spinal implant system of any one of examples 31-33, wherein at least one of the hollow upper anchor or the hollow lower anchor includes an outlet through which the bone cement exits the spinal implant system.

35. The spinal implant system of any one of examples 31-34, wherein the hollow upper anchor is configured to extend upwardly past a lower endplate of the upper vertebra when the intervertebral body contacts the lower endplate; and the hollow lower anchor is configured to extend downwardly past an upper endplate of the lower vertebra when the intervertebral body contacts the lower endplate.

36. The spinal implant system of any one of examples 31-35, wherein the hollow upper and lower anchors have longitudinal axes generally parallel to a parasagittal plane of the intervertebral body.

37. The spinal implant system of any one of examples 31-36, wherein one or both of the hollow upper and lower anchors includes through-holes through which the bone cement is capable of flowing to exit the spinal implant system.

38. The spinal implant system of any one of examples 31-37, wherein the hollow upper anchor is a first upper anchor, and the hollow lower anchor is a first lower anchor, the spinal implant system further including:

a second upper anchor configured to extend into the upper vertebra; and a second lower anchor configured to extend into the lower vertebra, wherein a continuous flow passageway extends through the first and second upper anchor, through the first and second lower anchors, and through a portion of an anchor-receiving bifurcated fixation hole of the intervertebral body, thereby rigidly locking the spinal implant system together after implantation in the subject.

39. The spinal implant system of any one of examples 31-38, wherein the intervertebral body is an intervertebral cage including a bone-cement flow-through porous region; and a bone graft receiving region that is configured to hold bone graft material while the bone cement flows through the bone-cement flow-through porous region.

40. The spinal implant system of any one of examples 25-39, further comprising:

a delivery device including a pump and a delivery cannula fluidically connected to the pump, wherein the pump is operable to drive the bone cement through and out of the delivery cannula positioned in the implant assembly.

41. The spinal implant system of example 40, wherein the delivery device is configured to hold and dispense a therapeutically effective amount of the bone cement to therapeutically reinforce the at least one of the upper vertebra or the lower vertebra.

42. The spinal implant system of example 40 or example 41, wherein a distal portion of the delivery cannula is configured to be moved through a passageway of at least one of hollow upper or lower anchors extending through the intervertebral body.

43. The spinal implant system of any one of examples 40-42, wherein the delivery device is configured to expel the bone cement while being moved proximally along the continuous bone cement flow path.

44. The spinal implant system of any one of examples 40-43, wherein the pump is syringe pump configured to dispense a volume of the bone cement from the delivery cannula while withdrawing the delivery cannula to gradually fill the spinal implant system with the volume of bone cement.

45. The spinal implant system of any one of examples 40-44, wherein a distal end of the delivery cannula is configured to be moved in a superior/inferior direction through the spinal implant system to position the distal end inside at least one of the upper vertebra or the lower vertebra.

46. The spinal implant system of any one of examples 25-45, wherein the interconnected passageways includes a bifurcated fixation hole, an upper opening for facing the upper vertebra, and a lower opening for facing a lower vertebra, wherein the bifurcated fixation hole includes an angled passageway having a generally V-shaped configuration for connecting the upper opening to the lower opening through a central chamber of the intervertebral body.

47. The spinal implant system of any one of examples 25-46, further comprising a hollow upper anchor and a hollow lower anchor each include a curved segment configured to follow arcuate paths of the interconnected passageways when inserted into the respective upper vertebra and lower vertebra.

48. The spinal implant system of any one of examples 25-47, further comprising a hollow upper anchor and a hollow lower configured to be positioned on opposite sides of a parasagittal plane of the intervertebral body and are vertically aligned to facilitate material flow between their respective hollow passageways.

49. The spinal implant system of any one of examples 25-48, wherein the intervertebral body includes a partition wall extending through a central chamber to separate a bone-cement flow-through porous region from a bone graft receiving region within the intervertebral body.

50. The spinal implant system of any one of examples 25-49, further comprising a hollow upper anchor and a hollow lower anchor configured to extend through the intervertebral body, wherein at least one of the hollow upper or lower anchors including motion inhibiting features including at least one of external threads, ribs, or surface texturing configured to engage with bone tissue and resist anchor migration.

51. The spinal implant system of any one of examples 25-50, wherein the intervertebral body has a first porous region with a first average porosity and a second porous region with a second average porosity different from the first average porosity.

52. The spinal implant system of example 51, wherein a ratio of the first average porosity to the second average porosity is greater than 2.

53. The spinal implant system of example 51 or example 52, wherein the first porous region is an outer region and the second porous region is inside region, and wherein the first average porosity is substantially less than the second average porosity.

54. The spinal implant system of any one of examples 25-53, further comprising:

a delivery device including a pump and a delivery cannula fluidically connected to the pump, wherein the pump is operable to cause the delivery device to eject cement through a hole in the delivery cannula, wherein the delivery cannula is rotatable within a passageway of one of the hollow upper anchor or the hollow lower anchor to direct cement through a specific hole in the one of the hollow upper anchor or the hollow lower anchor.

55. A method of employing a bone reinforcing material to retain an intervertebral spacer in position between two adjacent vertebrae, the method comprising:

placing the intervertebral spacer in position between two adjacent vertebrae;

inserting a cannula in accordance with one of the following:

(a) through one vertebra of the two adjacent vertebrae and at least penetrating into the intervertebral spacer;

(b) through the intervertebral spacer and at least penetrating one vertebra of the two adjacent vertebra;

dispensing a volume of a bone reinforcement composition through the cannula;

withdrawing the cannula and dispensing the volume of a bone reinforcement composition from the cannula during the withdrawing process into each of the respective one vertebra of the two adjacent vertebrae and the intervertebral spacer;

dispensing a volume of a bone reinforcement composition into at least one of the respective adjacent intervertebral member and vertebrae; and removing the cannula.

56. The method of example 55, further comprising a step of the bone reinforcement composition setting, wherein the set bone reinforcement composition anchors the intervertebral spacer in situ between the two adjacent vertebrae.

57. The method of example 55 or example 56, wherein the bone reinforcement composition is a bone cement.

58. The method of any one of examples 55-57, wherein the bone reinforcement composition is a re-absorbable structural compound.

59. The method of any one of examples 55-58, wherein the bone reinforcement composition is a bone graft material.

60. The method of any one of examples 55-59, wherein the step of withdrawing the cannula and dispensing the volume of a bone reinforcement composition is accomplished in repeating steps of withdrawing the cannula a short distance, stopping the withdrawal, and dispensing the volume of a bone reinforcement composition.

61. The method of any one of examples 55-60, further comprising inserting a cannula guide instrument into position for dispensing the bone reinforcement composition, and passing the cannula through the cannula guide instrument for dispensing the bone reinforcement composition therethrough.

62. The method of example 61, wherein the cannula guide instrument includes a linear tubular element of sufficient strength to penetrate bone.

63. The method of any one of examples 55-62, further comprising viewing a location of the cannula using real time imaging equipment.

64. The method of example 63, wherein the real time imaging equipment includes a fluoroscope.

65. The method of any one of examples 55-64, wherein the intervertebral spacer includes at least one cannula guide directed towards a respective adjacent vertebra of the two adjacent vertebra, and wherein inserting the cannula comprises inserting the cannula through the at least one cannula guide.

66. The method of any one of examples 55-65, wherein the intervertebral spacer has a porous structure with a porosity gradient, the porosity gradient having a higher porosity in a central region of the intervertebral spacer and a lower porosity near outer surfaces of the intervertebral spacer.

67. The method of example 66, wherein the porosity gradient of the intervertebral spacer may facilitate controlled distribution of the bone reinforcement composition, with the higher porosity central region allowing for greater material flow and the lower porosity outer surfaces providing increased structural support.

68. The method of example 66 or example 67, further comprising delivering bone graft material into a first chamber of the intervertebral spacer; and delivering the bone reinforcing material into a second chamber of the intervertebral spacer.

69. The method of example 67, wherein the bone reinforcing material is delivered into the second chamber after the bone graft material has been delivered into the first chamber.

70. The method of example 67 or example 68, wherein the bone graft material occupies most of the first chamber of the implant, and the bone reinforcing material occupies most of the second chamber.

71. A method comprising:

positioning an intervertebral spacer in position between two adjacent vertebrae of a patient;

delivering a cannula through the intervertebral spacer and into at least one of the two adjacent vertebrae; and delivering, via the cannula, a bone reinforcement material into the at least one of the two adjacent vertebrae and into the intervertebral spacer.

72. The method of example 71, further comprising moving proximally the cannula and dispensing a volume of the bone reinforcement material while proximally moving the cannula.

73. The method of example 71 or example 72, further comprising allowing the bone reinforcement material to set to anchor the intervertebral spacer in situ between the two adjacent vertebrae.

74. The method of any one of examples 71-73, wherein the intervertebral spacer has one or more interconnected passageways defining a continuous bone cement flow path along which the bone reinforcement material flows through a porous regions of the intervertebral body.

75. The method of any one of examples 71-74, wherein the bone reinforcement material is a bone cement.

76. The method of any one of examples 71-75, wherein the bone reinforcement material is a re-absorbable structural compound.

77. The method of any one of examples 71-76, wherein the bone reinforcement material is a bone graft material.

78. The method of any one of examples 71-77, further comprising dispensing a volume of a bone reinforcement material is accomplished in repeating steps of withdrawing the cannula a short distance, stopping the withdrawal, and dispensing the volume of a bone reinforcement composition.

79. The method of any one of examples 71-78, further comprising inserting a cannula guide instrument into position for dispensing the bone reinforcement material, and passing the cannula through the cannula guide instrument for dispensing the bone reinforcement material therethrough.

80. The method of example 79, wherein the cannula guide instrument includes a linear tubular element of sufficient strength to penetrate bone.

81. The method of any one of examples 71-80, further comprising viewing a location of the cannula using real time imaging equipment.

82. The method of example 80, wherein the real time imaging equipment includes a fluoroscope.

83. The method of any one of examples 71-82, wherein the intervertebral spacer includes at least one cannula guide directed towards a respective adjacent vertebra of the two adjacent vertebrae, and wherein inserting the cannula comprises inserting the cannula through the at least one cannula guide.

84. The method of any one of examples 71-83, wherein the intervertebral spacer includes a porous structure with a porosity gradient, the porosity gradient having a higher porosity in a central region of the intervertebral spacer and a lower porosity near outer surfaces of the intervertebral spacer.

85. The method of example 84, wherein the porosity gradient of the intervertebral spacer may facilitate controlled distribution of the bone reinforcement material, with the higher porosity central region allowing for greater material flow and the lower porosity outer surfaces providing increased structural support.

86. The method of example 84 or example 85, further comprising:

delivering bone graft material into a first chamber of the intervertebral spacer; and delivering the bone reinforcement material into a second chamber of the implant.

87. The method of example 86, wherein the bone reinforcement material is delivered into the second chamber of the implant after the bone graft material has been delivered into the first chamber of the implant.

88. The method of example 86 or example 87, wherein the bone graft material occupies most of the first chamber of the implant, and the bone reinforcement material occupies most of the second chamber.

89. A method comprising:

positioning an intervertebral spacer in position between a first vertebra and a second vertebra of a patient; and while the intervertebral spacer is positioned between the first vertebra and the second vertebra, delivering a bone reinforcement material to form a continuous cement column extending between inside the first vertebrae, inside the second vertebrae, and inside the intervertebral spacer.

90. The method of example 89, further comprising delivering the bone reinforcement material using a delivery cannula extending through the intervertebral spacer into both the first vertebra and the second vertebra.

91. The method of example 89 or example 90, further comprising:
delivering bone graft material into a first chamber of the intervertebral spacer; and
delivering the bone reinforcement material into a second chamber of the intervertebral spacer.

92. The method of example 91, wherein the bone reinforcement material is delivered into the second chamber of the implant after the bone graft material has been delivered into the first chamber of the implant.

93. The method of example 91 or example 92, wherein the bone graft material occupies most of the first chamber of the implant, and the bone cement material occupies most of the second chamber.

94. The method of any one of examples 89-93 wherein the continuous cement column extends through one or more anchors extending from the intervertebral spacer into the first vertebra and/or the second vertebra.

The embodiments, implants, anchors, features, systems, devices, materials, methods, and techniques described herein may, in some embodiments, be similar to any one or more of the embodiments, features, systems, devices, materials, methods, and techniques described in the following:

U.S. application Ser. No. 18/670,649, filed May 21, 2024, titled "ORTHOPEDIC SPINAL SURGICAL IMPLANT AND METHOD OF USE";

U.S. application Ser. No. 19/080,690, filed Mar. 14, 2025, titled "VERTEBRAL CEMENT INJECTION SYSTEM AND METHOD OF USE";

U.S. Provisional Application No. 63/460,330, filed Apr. 19, 2023;

U.S. Provisional Application No. 63/528,912, filed Jul. 25, 2023;

U.S. Provisional Application No. 63/565,655, filed Mar. 15, 2024, titled "VERTEBRAL CEMENT INJECTION SYSTEM AND METHOD OF USE";

U.S. Provisional Application No. 63/674,778, filed Jul. 23, 2024;

U.S. Provisional Application No. 63/827,769, filed Jun. 20, 2025;

U.S. Provisional Application No. 63/727,639, filed Dec. 3, 2024; and

International App. No. PCT/US25/3045, filed May 21, 2025.

All of the above-identified patents and applications are incorporated by reference in their entireties. In addition, the embodiments, features, systems, devices, materials, methods, and techniques described herein may, in certain embodiments, be applied to or used in connection with any one or more of the embodiments, features, systems, devices, or other matter. For example, features disclosed herein can be incorporated into the embodiments of U.S. application Ser. No. 18/670,649. Although the exemplary application describes an intervertebral application, the concept of employing an aperture through an implant for guidance of a system for injecting a bone reinforcement composition into a region of a bone adjacent to a joint can be implemented for any suitable joint.

The above-described embodiments are merely exemplary illustrations of implementations set forth for a clear understanding of the principles of the invention. Many variations, combinations, modifications or equivalents may be substituted for elements thereof without departing from the scope of the invention. Therefore, it is intended that the invention not be limited to the particular embodiments disclosed as the best mode contemplated for carrying out this invention, but that the invention will include all the embodiments falling within the scope of the appended claims.

What is claimed is:

1. A method of employing a bone reinforcing material to retain an intervertebral spacer in position between two adjacent vertebrae, the method comprising:
placing the intervertebral spacer in position between two adjacent vertebrae;
after placing the intervertebral spacer between the two adjacent vertebrae,
moving a hollow anchor though the intervertebral spacer and into one vertebra of the two adjacent vertebrae;
inserting a cannula through a portion of the hollow anchor positioned within the one vertebra of the two adjacent vertebrae; and
dispensing a volume of a bone reinforcement composition through the cannula;
withdrawing the cannula, which is located in the hollow anchor, and dispensing at least a portion of the volume of the bone reinforcement composition from the cannula into the one vertebra of the two adjacent vertebrae during the withdrawing process; and
removing the cannula from the hollow anchor.

2. The method of claim 1, further comprising a step of the bone reinforcement composition setting, wherein the set bone reinforcement composition anchors the intervertebral spacer in situ between the two adjacent vertebrae.

3. The method of claim 1, wherein the step of withdrawing the cannula and dispensing the volume of the bone reinforcement composition is accomplished in repeating steps of withdrawing the cannula a short distance, stopping the withdrawal, and dispensing the volume of the bone reinforcement composition.

4. The method of claim 1, further comprising
inserting a cannula guide instrument into position for dispensing the bone reinforcement composition, and
passing the cannula through the cannula guide instrument for dispensing the bone reinforcement composition therethrough.

5. The method of claim 4, wherein the cannula guide instrument includes a linear tubular element of sufficient strength to penetrate bone.

6. The method of claim 1, wherein the intervertebral spacer includes at least one cannula guide directed towards a respective adjacent vertebra of the two adjacent vertebrae, and wherein inserting the cannula comprises inserting the cannula through the at least one cannula guide.

7. The method of claim 1, wherein the intervertebral spacer includes a porous structure with a porosity gradient, the porosity gradient having a higher porosity in a central region of the intervertebral spacer and a lower porosity near outer surfaces of the intervertebral spacer.

8. The method of claim 7, wherein the porosity gradient of the intervertebral spacer may facilitate controlled distribution of the bone reinforcement composition, with the higher porosity central region allowing for greater material flow and the lower porosity outer surfaces providing increased structural support.

9. A method of employing a bone reinforcing material to retain an intervertebral spacer in position between two adjacent vertebrae of a patient, the method comprising:
delivering bone graft material into a first chamber of the intervertebral spacer;
placing the intervertebral spacer in position between the two adjacent vertebrae, wherein the intervertebral spacer includes a porous structure with a porosity gradient, the porosity gradient having a higher porosity in a central region of the intervertebral spacer and a lower porosity near outer surfaces of the intervertebral spacer;

inserting a cannula in accordance with one of the following:

(a) through one vertebra of the two adjacent vertebrae and at least penetrating into the intervertebral spacer; or (b) through the intervertebral spacer and at least penetrating one vertebra of the two adjacent vertebrae:

dispensing a volume of a bone reinforcement composition through the cannula, wherein at least a portion of the volume of the bone reinforcement composition is delivered from the cannula being withdrawn such that the bone reinforcing material is delivered into a second chamber of the intervertebral spacer and into each of the respective one vertebra of the two adjacent vertebrae; and removing the cannula from the patient.

10. The method of claim 9, wherein the bone reinforcing material is delivered into the second chamber after the bone graft material has been delivered into the first chamber.

11. The method of claim 9, wherein the bone graft material occupies most of the first chamber of the intervertebral spacer, and the bone reinforcing material occupies most of the second chamber.

12. The method of claim 9, further comprising positioning a cannula guide instrument in the one vertebra of the two adjacent vertebrae; and moving the cannula through the cannula guide instrument to insert the cannula through the one vertebra and/or the intervertebral spacer and at least penetrating one vertebra.

13. The method of claim 9, further comprising inserting a cannula guide instrument into the patient, and passing the cannula through the cannula guide instrument for dispensing the bone reinforcement composition.

14. A method comprising:

positioning an intervertebral spacer in position between a first vertebra and a second vertebra of a patient;

delivering a first anchor through the intervertebral spacer and into the first vertebra;

delivering a second anchor through the intervertebral spacer and into the second vertebra, wherein a bifurcate passageway includes a first passageway extending through the first anchor, and a second passageway extending through the second anchor; and selectively delivering, via at least one cannula, a bone reinforcement material along the first passageway and the second passageway such that the bone reinforcement material is delivered into the first vertebra and the second vertebra and extends through a portion of the intervertebral spacer between the first passageway and the second passageway.

15. The method of claim 14, further comprising moving proximally the at least one cannula and dispensing a volume of the bone reinforcement material while proximally moving the at least one cannula.

16. The method of claim 14, further comprising allowing the bone reinforcement material to set to anchor the intervertebral spacer in situ between the first vertebra and the second vertebra.

17. The method of claim 14, wherein the intervertebral spacer has one or more interconnected passageways defining a continuous bone cement flow path along which the bone reinforcement material flows through a porous regions of the intervertebral spacer.

18. The method of claim 14, wherein the bone reinforcement material is a bone cement.

19. The method of claim 14, wherein the bone reinforcement material is a re-absorbable structural compound.

20. The method of claim 14, wherein the bone reinforcement material is a bone graft material.

21. The method of claim 14, further comprising dispensing a volume of the bone reinforcement material is accomplished in repeating steps of withdrawing the at least one cannula a short distance, stopping the withdrawal, and dispensing the volume of a bone reinforcement composition.

22. The method of claim 14, further comprising inserting a cannula guide instrument into position for dispensing the bone reinforcement material, and passing the at least one cannula through the cannula guide instrument for dispensing the bone reinforcement material therethrough.

23. The method of claim 14, further comprising viewing a location of the at least one cannula using real time imaging equipment.

24. The method of claim 14, wherein the intervertebral spacer includes at least one cannula guide directed towards a respective adjacent vertebra of the first vertebra and the second vertebra, and wherein inserting the at least one cannula comprises inserting the at least one cannula through the at least one cannula guide.

25. The method of claim 14, wherein the intervertebral spacer includes a porous structure with a porosity gradient, the porosity gradient having a higher porosity in a central region of the intervertebral spacer and a lower porosity near outer surfaces of the intervertebral spacer.

26. The method of claim 25, wherein the porosity gradient of the intervertebral spacer may facilitate controlled distribution of the bone reinforcement material, with the higher porosity central region allowing for greater material flow and the lower porosity outer surfaces providing increased structural support.

27. A method comprising:

delivering bone graft material into a first chamber of an intervertebral spacer, wherein the intervertebral spacer includes a porous structure with a porosity gradient, the porosity gradient having a higher porosity in a central region of the intervertebral spacer and a lower porosity near outer surfaces of the intervertebral spacer;

positioning an intervertebral spacer in position between two adjacent vertebrae of a patient;

delivering a cannula through the intervertebral spacer and into at least one of the two adjacent vertebrae;

delivering, via the cannula, a bone reinforcement material into the at least one of the two adjacent vertebrae; and delivering the bone reinforcement material into a second chamber of the intervertebral spacer.

28. The method of claim 27, wherein the bone reinforcement material is delivered into the second chamber of the intervertebral spacer after the bone graft material has been delivered into the first chamber of the intervertebral spacer.

29. The method of claim 27, wherein the bone graft material occupies most of the first chamber of the intervertebral spacer, and the bone reinforcement material occupies most of the second chamber.

30. A method comprising:

positioning an intervertebral spacer in position between a first vertebra and a second vertebra of a patient;

after positioning the intervertebral spacer between the first vertebra and the second vertebra, moving a first hollow anchor through an intervertebral cage of the intervertebral spacer and into the first vertebra, moving a second hollow anchor through the intervertebral cage and into the second vertebra; and delivering a bone reinforcement material to form a continuous cement column extending between inside the first vertebra, inside the second vertebra, inside the first hollow anchor and the second hollow anchor, and inside the intervertebral spacer.

31. The method of claim 30, wherein the continuous cement column extends through the first hollow anchor, the second hollow anchor, and a portion of the intervertebral cage between the first hollow anchor and the second hollow anchor, thereby rigidly locking together the intervertebral spacer, the first vertebra, and the second vertebra.

32. The method of claim 30, further comprising delivering the bone reinforcement material through one or more openings in a sidewall of the first hollow anchor.

33. The method of claim 30, wherein the bone reinforcement material flows through a V-shaped portion of the intervertebral spacer.

34. The method of claim 30, wherein the intervertebral spacer includes porous region through which the bone reinforcement material flows to form the continuous cement column.

35. The method of claim 30, wherein the bone reinforcement material flows through one or more porous regions of the intervertebral spacer to form the continuous cement column.

36. The method of claim 30, further comprising
inserting a cannula guide instrument into position for dispensing the bone reinforcement composition, and
passing the cannula through the cannula guide instrument for dispensing the bone reinforcement composition.

* * * * *